United States Patent
Burton et al.

(10) Patent No.: US 10,716,926 B2
(45) Date of Patent: *Jul. 21, 2020

(54) MICRONEEDLE INJECTION AND INFUSION APPARATUS AND METHOD OF USING SAME

(71) Applicant: Kindeva Drug Delivery L.P., St. Paul, MN (US)

(72) Inventors: Scott A. Burton, Woodbury, MN (US); Chin-Yee Ng, Oakdale, MN (US); Michael J. Frits, Lake Elmo, MN (US); Richard R. Mathias, Brookline, MA (US)

(73) Assignee: Kindeva Drug Delivery L.P., St. Paul, MN (US)

( * ) Notice: Subject to any disclaimer, the term of this patent is extended or adjusted under 35 U.S.C. 154(b) by 249 days.

This patent is subject to a terminal disclaimer.

(21) Appl. No.: 15/838,542

(22) Filed: Dec. 12, 2017

(65) Prior Publication Data

US 2018/0110970 A1  Apr. 26, 2018

Related U.S. Application Data

(63) Continuation of application No. 14/892,249, filed as application No. PCT/US2014/039133 on May 22, 2014, now Pat. No. 9,872,975.

(Continued)

(51) Int. Cl.
*A61M 37/00* (2006.01)
*A61M 5/32* (2006.01)
*A61M 5/142* (2006.01)

(52) U.S. Cl.
CPC .... *A61M 37/0015* (2013.01); *A61M 5/14248* (2013.01); *A61M 5/322* (2013.01);
(Continued)

(58) Field of Classification Search
CPC .. A61M 2037/0023; A61M 2037/0061; A61M 37/0015; A61M 5/322; A61M 2025/0093; A61K 9/0021
See application file for complete search history.

(56) References Cited

U.S. PATENT DOCUMENTS 3,134,380 A  5/1964  Armao
4,472,480 A  9/1984  Olson
(Continued)

FOREIGN PATENT DOCUMENTS

EP  2399643  12/2011
JP  2012-100783  5/2012
(Continued)

OTHER PUBLICATIONS

International Search Report for PCT International Application No. PCT/US2014/039133, dated Sep. 4, 2014, 5 pages.

*Primary Examiner* — Quynh-Nhu H. Vu
(74) *Attorney, Agent, or Firm* — Mueting Raasch Group

(57) ABSTRACT

A microneedle injection and infusion apparatus, and a method of using same. The apparatus can include a housing, a microneedle array holder for holding a microneedle array, and a shuttle that holds a cartridge (e.g., that contains an active agent). The microneedle array holder can be movable between a retracted position and an extended position. The shuttle can be movable between a first position in which the cartridge is not in fluid communication with a fluid path and a second position in which the cartridge is in fluid communication with the fluid path. The apparatus can further include an actuator movable between a first position and a second position. The method can include moving the actuator to its second position to allow the shuttle to move toward its second position, wherein movement of the shuttle toward its second position allows the microneedle array holder to move to its extended position.

24 Claims, 22 Drawing Sheets

Related U.S. Application Data

(60) Provisional application No. 61/829,651, filed on May 31, 2013.

(52) U.S. Cl.
CPC ... *A61M 5/3297* (2013.01); *A61M 2037/0023* (2013.01); *A61M 2037/0061* (2013.01)

(56) References Cited

U.S. PATENT DOCUMENTS

| | | | |
|---|---|---|---|
| 4,584,355 A | 4/1986 | Blizzard | |
| 4,585,836 A | 4/1986 | Homan | |
| 4,591,622 A | 5/1986 | Blizzard | |
| 4,655,767 A | 4/1987 | Woodard | |
| 4,693,776 A | 9/1987 | Krampe | |
| 4,751,087 A | 6/1988 | Wick | |
| 4,834,979 A | 5/1989 | Gale | |
| 5,223,261 A | 6/1993 | Nelson | |
| 5,380,760 A | 1/1995 | Wendel | |
| 5,656,286 A | 8/1997 | Miranda | |
| 5,688,523 A | 11/1997 | Garbe | |
| 5,885,255 A | 3/1999 | Jaeger, Jr. | |
| 6,004,578 A | 12/1999 | Lee | |
| 6,024,976 A | 2/2000 | Miranda | |
| 6,091,975 A | 7/2000 | Daddona | |
| 6,149,935 A | 11/2000 | Chiang | |
| 6,312,612 B1 | 11/2001 | Sherman | |
| 6,365,178 B1 | 4/2002 | Venkateshwaran | |
| 6,379,324 B1 | 4/2002 | Gartstein | |
| 6,558,361 B1 | 5/2003 | Yeshurun | |
| 7,097,631 B2 | 8/2006 | Trautman | |
| 7,648,484 B2 | 1/2010 | Yeshurun | |
| D681,195 S | 4/2013 | Skulley | |
| 9,682,222 B2* | 6/2017 | Burton | A61M 37/0015 |
| 9,872,975 B2* | 1/2018 | Burton | A61M 37/0015 |
| 2002/0087182 A1 | 7/2002 | Trautman | |
| 2003/0054025 A1 | 3/2003 | Cantor | |
| 2004/0049150 A1 | 3/2004 | Dalton | |
| 2005/0261631 A1 | 11/2005 | Clarke | |
| 2010/0121271 A1 | 5/2010 | Perriere | |
| 2011/0172601 A1 | 7/2011 | Beebe | |
| 2011/0213335 A1 | 9/2011 | Burton | |
| 2011/0276027 A1 | 11/2011 | Trautman | |
| 2012/0109066 A1 | 5/2012 | Chase | |
| 2012/0123387 A1* | 5/2012 | Gonzalez | A61M 37/0015 604/506 |
| 2012/0143119 A1 | 6/2012 | Deasey | |
| 2014/0128818 A1 | 5/2014 | Ogura | |
| 2014/0243786 A1 | 8/2014 | Gilbert | |

FOREIGN PATENT DOCUMENTS

| | | |
|---|---|---|
| WO | WO 1999-30759 | 6/1999 |
| WO | WO 2002-05889 | 1/2002 |
| WO | WO 2002-30300 | 4/2002 |
| WO | WO 2004-009172 | 1/2004 |
| WO | WO 2005-018705 | 3/2005 |
| WO | WO 2010-059605 | 5/2005 |
| WO | WO 2006-062974 | 6/2006 |
| WO | WO 2007-002521 | 1/2007 |
| WO | WO 2007-002522 | 1/2007 |
| WO | WO 2007-036676 | 4/2007 |
| WO | WO 2007-075806 | 7/2007 |
| WO | WO 2007-112309 | 10/2007 |
| WO | WO 2008-101892 | 8/2008 |
| WO | WO 2008-157592 | 12/2008 |
| WO | WO 2009-031144 | 3/2009 |
| WO | WO 2010-010974 | 1/2010 |
| WO | WO 2010-117602 | 10/2010 |
| WO | WO 2010-126174 | 11/2010 |
| WO | WO 2011-014514 | 2/2011 |
| WO | WO 2011-075569 | 6/2011 |
| WO | WO 2012-074576 | 6/2012 |
| WO | WO 2012-088154 | 6/2012 |
| WO | WO 2012-089627 | 7/2012 |
| WO | WO 2012-098503 | 7/2012 |
| WO | WO 2012-122162 | 9/2012 |
| WO | WO 2013-015136 | 1/2013 |
| WO | WO 2013-036602 | 3/2013 |
| WO | WO 2014/110016 | 7/2014 |
| WO | WO 2014-193727 | 12/2014 |
| WO | WO 2014-193729 | 12/2014 |

* cited by examiner

MICRONEEDLE INJECTION AND INFUSION APPARATUS AND METHOD OF USING SAME

CROSS REFERENCE TO RELATED APPLICATIONS

This application is a continuation of U.S. patent application Ser. No. 14/892,249, filed Nov. 19, 2015, which is a national stage filing under 35 U.S.C. 371 of PCT/US2014/039133, filed May 22, 2014, which claims the benefit of U.S. Provisional Patent Application No. 61/829,651, filed May 31, 2013, the disclosure of which are incorporated by reference in their entirety herein.

FIELD

The present disclosure generally relates to microneedle injection and infusion devices for delivering an active agent to skin via microneedles.

BACKGROUND

Active agents (or drugs) are conventionally administered either orally or by injection. Unfortunately, many agents can be ineffective or have radically reduced efficacy when orally administered since they either are not absorbed or are adversely affected before entering the bloodstream and thus do not possess the desired activity. Further, orally administered agents may not take effect as quickly as injected agents. On the other hand, the direct injection of the agent into the bloodstream, while assuring no modification of the agent during administration, is a difficult, inconvenient, painful and uncomfortable procedure which sometimes results in poor patient compliance.

Transdermal delivery can provide a method of administering active agents that would otherwise need to be delivered via hypodermic injection or intravenous infusion. In addition, transdermal delivery, when compared to oral delivery, avoids the harsh environment of the digestive tract, bypasses gastrointestinal drug metabolism, reduces first-pass effects, and avoids the possible deactivation by digestive and liver enzymes.

In some cases, however, the number of molecules that can be effectively delivered using transdermal delivery can be limited by the barrier properties of skin. The main barrier to the transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which make up the majority of epidermal cells, that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Microneedle or micro-pin arrays, also sometimes referred to as microstructured transdermal systems (MTSs), provide intradermal delivery of active agents, which otherwise would not penetrate the stratum corneum. The sharp microneedle tip is designed to be able to penetrate the stratum corneum layer of the skin, but short enough not to puncture nerve endings, thus reducing or eliminating pain upon insertion. However, the penetration of microneedles to precise levels within the skin tissue and with good reproducibility is often a challenging task. Therefore, unlike the application of traditional patch-based delivery systems, some existing MTSs require the assistance of external energy to ensure efficient and reproducible penetration of microneedles into biological tissue at desired depths. This assistance can be achieved by utilizing an apparatus device, which can either be used after positioning the microneedle array on the skin surface, or the apparatus device can be integrated with an array of microneedles and, upon activation, can deliver the microneedle array into the skin. The microneedles help to create microchannels in the skin, which in some embodiments, can facilitate delivering an active ingredient. In some constructions, active component(s) may be coated on the microneedle array and delivered directly through the skin when the stratum corneum is punctured by the microneedles. One advantage of MTS systems over other skin treatment methods is a reduced-pain mode of delivery.

SUMMARY

Some embodiments of the present disclosure provide a microneedle injection and infusion apparatus that can include a housing having a base and a cavity that extends through the base to define an opening in the base, wherein the base of the housing is configured to be positioned toward a skin surface. The apparatus can further include a microneedle array holder configured to hold a microneedle array and located in the housing, the microneedle array holder movable with respect to the opening in the base of the housing between (i) a retracted position in which the microneedle array is recessed within the housing such that the microneedle array does not contact the skin surface when the apparatus is positioned on the skin surface and the microneedle array is coupled to the microneedle array holder, and (ii) an extended position in which at least a portion of the microneedle array is positioned to contact the skin surface via the opening when the apparatus is positioned on the skin surface and the microneedle array is coupled to the microneedle array holder. The apparatus can further include a shuttle configured to hold and carry a cartridge. The cartridge can define a reservoir configured to contain an active agent. The shuttle can be movable between a first position in which the reservoir of the cartridge is not in fluid communication with a fluid path and a second position in which the reservoir is in fluid communication with the fluid path. The apparatus can further include an actuator movable between a first position and a second position, wherein movement of the actuator to the second position releases the shuttle from its first position and allows the shuttle to move toward its second position, and wherein movement of the shuttle toward its second position releases the microneedle array holder from the retracted position and allows the microneedle array holder to move to the extended position.

Some embodiments of the present disclosure provide a method of using a microneedle injection apparatus. The method can include providing a microneedle injection apparatus. The apparatus can include a housing having a base and a cavity that extends through the base to define an opening in the base, wherein the base of the housing is configured to be positioned toward a skin surface. The apparatus can further include a microneedle array holder configured to hold a microneedle array and located in the housing, the microneedle array holder movable with respect to the opening in the base of the housing between (i) a retracted position in which the microneedle array is recessed within the housing such that the microneedle array does not contact the skin surface when the apparatus is positioned on the skin surface and the microneedle array is coupled to the microneedle array holder, and (ii) an extended position in which at least a portion of the microneedle array is positioned to contact the skin surface via the opening when the apparatus is positioned on the skin surface and the microneedle array is coupled to the microneedle array holder. The apparatus can further include a shuttle configured to hold and carry a cartridge. The cartridge can define a reservoir configured to contain an active agent. The shuttle can be movable between a first position in which the reservoir is not in fluid communication with a fluid path and a second position in which the reservoir is in fluid communication with the fluid path. The apparatus can further include an actuator movable between a first position and a second position. The method can further include moving the actuator to its second position to allow the shuttle to move toward its second position, wherein movement of the shuttle toward its second position allows the microneedle array holder to move to its extended position.

Other features and aspects of the present disclosure will become apparent by consideration of the detailed description and accompanying drawings.

DETAILED DESCRIPTION

Figure 1:
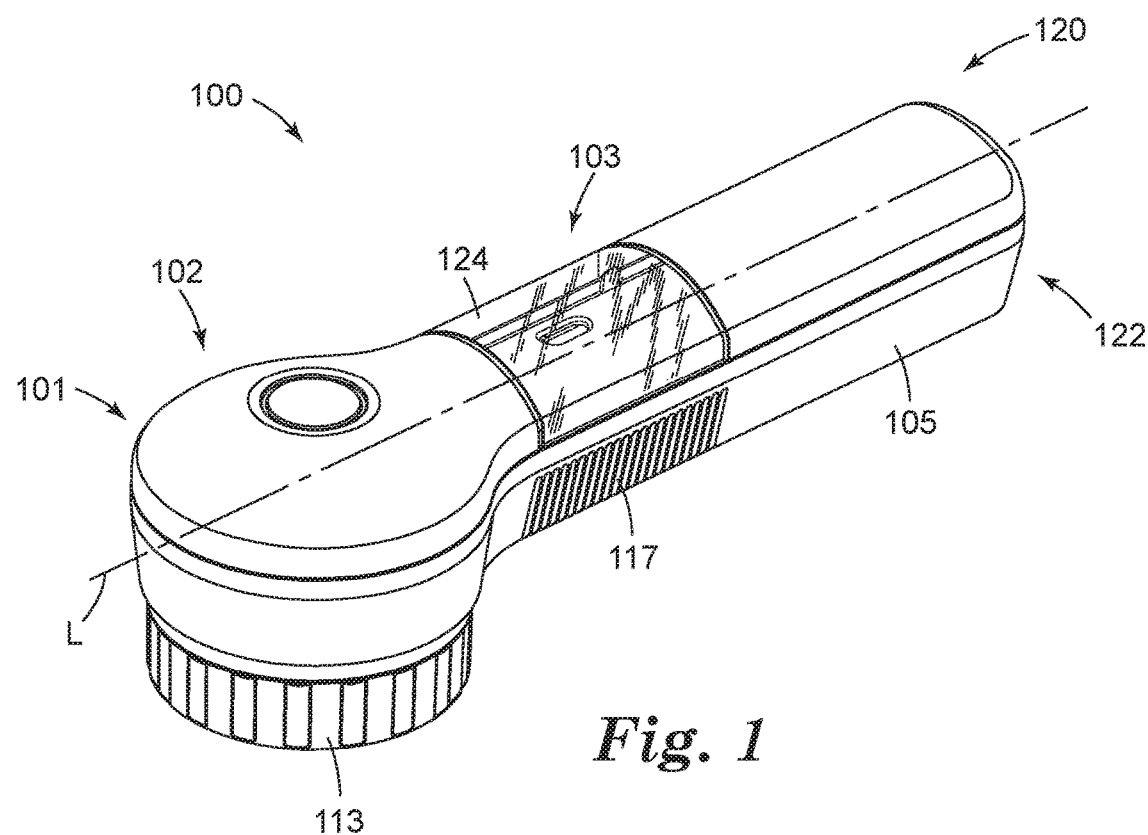
FIG. 1 is a front assembled top perspective view of a microneedle injection and infusion apparatus according to one embodiment of the present disclosure, the apparatus including a cover, and injection assembly, and an infusion assembly.
Figure 2:
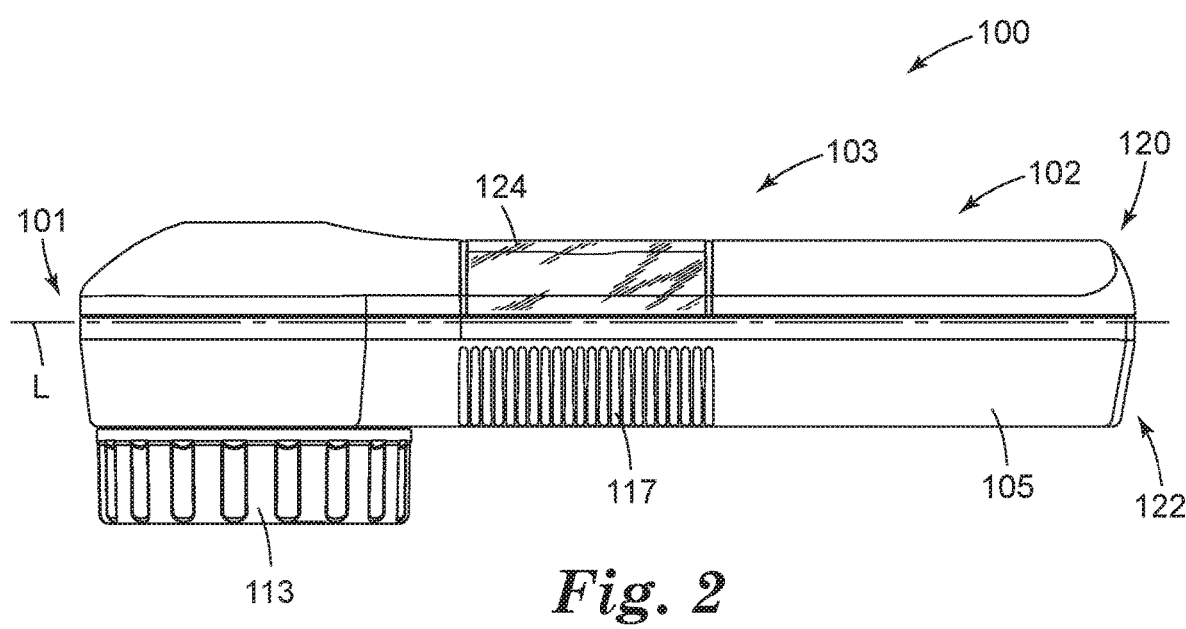
FIG. 2 is a side view of the apparatus of FIG. 1.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "supported," and "coupled," and variations thereof, are used broadly and encompass both direct and indirect mountings, supports, and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to microneedle injection and infusion apparatuses and methods of using same. Apparatuses of the present disclosure can include an array of microneedles that can be applied to skin (or a biological membrane) to treat the skin (i.e., create small holes or perforations or micropores in the skin) and can also deliver an active agent to the skin. Apparatuses of the present disclosure can be configured to be activated by a single actuation to automatically and reliably penetrate (or inject) a patient's skin with a microneedle array (e.g., a hollow microneedle array) and then automatically release and dispense thereto a stored fluid (e.g., an active agent) from a reservoir (e.g., a ready-to-use drug cartridge) in a controlled manner from an on-board infusion device into the skin via the microneedles. That is, one user-actuated action can initiate both injection and infusion without requiring the user to perform any additional steps after the single initial actuation.

The phrase "hollow microneedle" refers to a specific microscopic structure that includes a lumen formed therein. The hollow microneedles of the present disclosure are designed for piercing the stratum corneum to facilitate the delivery of active agents through the skin, e.g., via each lumen. By way of example, microneedles can include needle or needle-like structures, as well as other structures capable of piercing the stratum corneum and delivering the active agent. Additional details about microneedles that can be employed with the apparatuses of the present disclosure are described in greater detail below.

Apparatuses of the present disclosure can be configured to appropriately time and stage a sequence of events following actuation, such that, e.g., the microneedles are in place, penetrating the skin, before the active agent begins to be dispensed or released from the on-board infusion device. For example, in some embodiments, apparatuses of the present disclosure can include an injection assembly or device that includes a microneedle array holder, and an infusion assembly or device that includes a cartridge that defines a reservoir configured to contain an active agent. An actuator can be actuated to cause the injection device to inject microneedles into the skin and to initiate infusion of the active agent from the injection device through the injection device into the skin. In some embodiments, at least a portion of the infusion device can hold the injection device in a retracted position until the actuator causes the infusion device to move and release the injection device. By way of example only, and as described in greater detail below, the actuator can be moved from a first position to a second position, which releases a shuttle of the infusion device that holds and carries the cartridge, which in turn releases at least a portion of the injection device (e.g., the microneedle array holder). In some embodiments, the shuttle can continue moving after the injection device penetrates the skin to move the cartridge to an infusing position where the reservoir of the cartridge is in fluid communication with a fluid path (e.g., including hollow microneedles penetrating the skin). The active agent can then be forced out of the reservoir of the cartridge into the fluid path to deliver the active agent to the skin.

In discussing the apparatuses of the present disclosure, the term "downward," and variations thereof, is sometimes used to describe the direction in which microneedles are pressed into skin, and "upward" to describe the opposite direction. However, those of skill in the art will understand that the apparatuses can be used where the microneedles are pressed into skin at an angle to the direction of the earth's gravity, or even in a direction contrary to that of the earth's gravity, and these terms are only used for simplicity and clarity to describe relative directions.

FIGS. 1-25 illustrate a microneedle injection and infusion apparatus 100 according to one embodiment of the present disclosure. As shown, the apparatus 100 can include an injection assembly (or device) 101 and an infusion assembly (or device) 103, which can be an on-board infusion device.

The phrase "on-board infusion device" generally refers to an assembly or device capable of delivering an active agent to the microneedles of the injection assembly 101 for delivery to a patient's skin that forms a portion of, or is coupled to, and is operable with the injection assembly 101.

In some embodiments, the apparatus 100 can be referred to as a "controlled fluid release apparatus." In addition, the injection assembly 101 can also be referred to as an "applicator" or a "microneedle applicator;" and the infusion assembly 103 can also be referred to as a "fluid storage and delivery system or assembly."

The apparatus 100 can further include a housing 102; an actuator 104; a microneedle array holder 106 configured to hold and carry a microneedle array 107 comprising a plurality of hollow microneedles 108; a cartridge 110 defining a reservoir 111 configured to contain an active agent; and a cover 113. As shown in FIGS. 1, 2, 4 and 5, in some embodiments, the housing 102 can include a ridged or texturized surface or portion 117 to facilitate manually grasping and/or manipulating the apparatus 100.

In some embodiments, the cartridge 110 can be installed by manufacturers, assemblers, or users. In addition, the cartridge 110 and the microneedle array 107 can be replaced, thereby permitting reuse of the apparatus 100. Replaceable cartridges may provide an advantage of being able to be cleaned, sterilized, filled, and refilled as compared to microneedle devices having fixed or dedicated cartridges that are integrally formed therewith.

Figure 3:
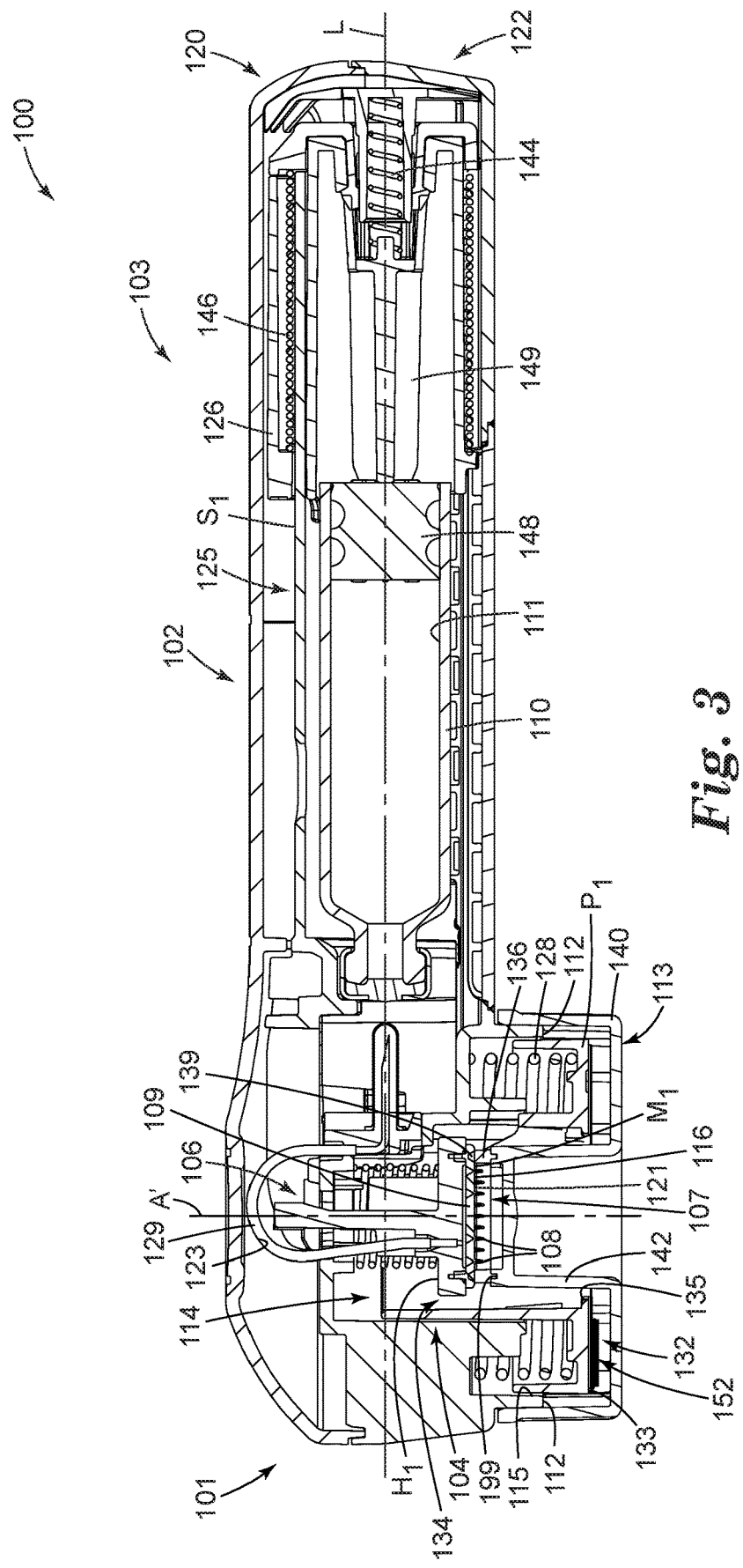
FIG. 3 is a side cross-sectional view of the apparatus of FIGS. 1 and 2.

As shown in FIG. 3, the injection assembly 101 can include the microneedle array holder 106 and a microneedle array 107 (i.e., when coupled to the microneedle array holder 106), and the infusion assembly 103 can include the cartridge 110. In some embodiments, the apparatus 100 can further include a fluid path 123 that is in fluid communication with or includes the microneedle array 107 (e.g., any surfaces or manifolds thereof, as well as the hollow microneedles 108), when the microneedle array 107 is coupled to the microneedle array holder 106. As a result, the fluid path 123 can deliver an active agent to and through the hollow microneedles 108. Such a fluid path 123 can provide fluid communication between the injection assembly 101 and the infusion assembly 103 and therefore, in some embodiments, can be described as forming a portion of either assembly, or as a connection between the assemblies.

In some embodiments, at least a portion of the fluid path 123 can be formed by a conduit or channel positioned to fluidly connect the cartridge 110 and the microneedles 108. In some embodiments, that conduit or channel can be provided by flexible tubing 129 (see FIGS. 3, 4 and 6). In some embodiments, one end of such tubing can be coupled to the microneedle array 107 and can travel with the microneedle array 107 (and microneedle array holder 106). Such flexible tubing 129 can allow a piercing element 175 that is in fluid communication with the fluid path 123 and is configured to pierce or puncture the cartridge 110 to remain in a fixed location within the housing 102. As such, the piercing element 175 need not travel with the microneedle array 107 and holder 106. Such tubing 129 can be formed of a variety of materials, including, but not limited to, polymeric materials, such as polypropylene, polyethylene, silicone, other suitable polymeric materials, or a combination thereof. However, in some embodiments, the piercing element 175 can be fixedly coupled to the holder 106, the apparatus 100 need not include the flexible tubing 129, and the piercing element 175 can be movable in the housing 102 with the microneedle array 107 and the holder 106.

The infusion assembly 103 can further include a shuttle 125 configured to hold and carry the cartridge 110 into fluid communication with the fluid path 123. The actuator 104 can be operable to actuate injection, movement of the shuttle 125 (and, accordingly, the cartridge 110), and infusion of the active agent into the fluid path 123 and out the hollow microneedles 108.

In some embodiments, the microneedles 108 can be configured to treat skin (i.e., create small holes or perforations or micropores in the skin) and deliver an active agent via skin, particularly, mammalian skin, and particularly, transdermally. Various microneedles that can be employed in apparatuses and methods of the present disclosure are described in greater detail below. Each hollow microneedle 108 includes a lumen 127 (see FIGS. 14 and 15). While a "plurality of microneedles" 108 is described in the present disclosure, it should be understood that not all of the microneedles 108 in a given array 107 are required to penetrate the skin (or to be coated with an active agent in embodiments in which the microneedles 108 include a coating) in a given use.

The term "transdermally," and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across or through at least a portion of skin (but not necessarily all of the layers of skin), rather than merely being topically applied to an outer layer of the skin.

In some embodiments, the housing 102 can be self-contained and compactly constructed to provide a relatively low profile and small footprint for, among other factors, ease of use and patient comfort. The term "footprint" generally refers to the surface area occupied by an item (e.g., the apparatus 100), e.g., on a skin surface. The footprint of a given item can be thought of as the area taken up by an outline of the outermost dimensions of the item. In some embodiments, "low profile" can refer to an apparatus 100 that is generally wide in relation to its height. That is, a "low profile" device can be one that has a dimension that extends along the skin surface that is greater than a dimension which extends generally normal to (and away from) the skin surface. Said another way, "low profile" can refer to a device having a skin-parallel dimension that is greater than its skin-normal dimension.

As shown, the apparatus 100, and the housing 102, can be elongated along a longitudinal axis L (see, e.g., FIGS. 1 and 2) and can be configured to be oriented substantially parallel with respect to a skin surface when in use. Such a configuration can provide a low profile for the apparatus 100. A low profile can reduce the likelihood of the microneedles 108 becoming dislodged during penetration and/or infusion and can facilitate hands-free wear. While designing the apparatus 100 such that the longitudinal axis L will be oriented generally parallel to a patient's skin surface during use can provide a low-profile and compact design, other orientations can be employed.

Figure 18:
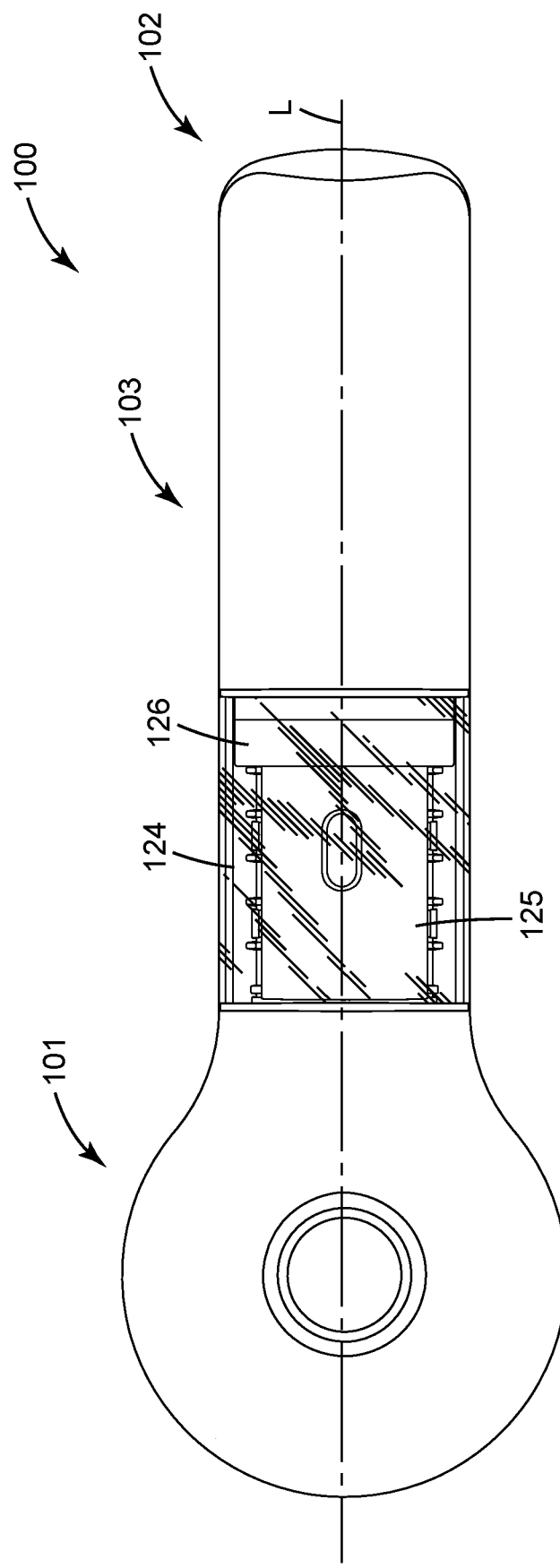
FIG. 18 is a top plan view of the apparatus of FIGS. 1-17, the apparatus shown in the sixth condition.
Figure 23:
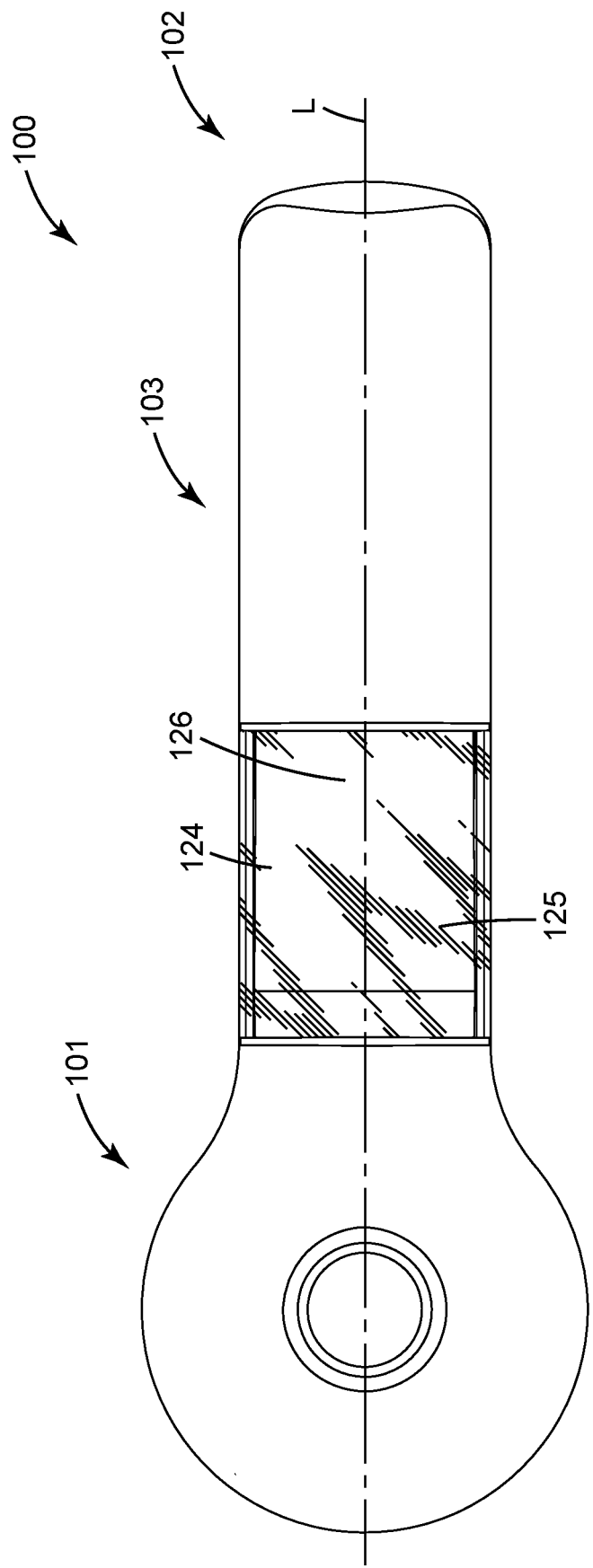
FIG. 23 is a top plan view of the apparatus of FIGS. 1-20, the apparatus shown in the seventh condition.

In some embodiments, the housing 102 can be formed of more than one portion. In some embodiments, the housing 102 can include a first (or upper) portion 120 adapted to be coupled (e.g., removably or permanently) to a second (or lower) portion 122, such that the first portion 120 can function as a cover for the second portion 122. At least a portion of the housing 102 (e.g., the first portion 120) can include one or more light-transmissive windows 124, which in some embodiments, can allow a user to observe the progress of at least a portion of the infusion process. For example, as shown in FIGS. 18 and 23 and described in greater detail below, in some embodiments, the infusion assembly 103 can include one or more indicators 126 for indicating the progress of infusion, and such indicators 126 can be visible via the window 124. The window(s) 124 need not be entirely transparent but at least partially transmissive to wavelengths in the visible spectrum (i.e., about 400 nm to about 700 nm) to allow for visual detection of the indicator(s) 126 via the window(s) 124.

The second portion 122 of the housing 102 can be configured to hold and retain the injection assembly 101 and the infusion assembly 103. Each of the first portion 120 and the second portion 122 of the housing can include one or more retaining walls 105. The first portion 120 and the second portion 122 of the housing 102 can be configured to be coupled together by a variety of coupling means, including, but not limited to, press-fit engagement (also sometimes referred to as "friction-fit engagement" or "interference-fit engagement"), snap-fit engagement, magnets, hook-and-loop fasteners, adhesives, cohesives, clamps, stitches, staples, screws, nails, rivets, brads, crimps, detents, welding (e.g., sonic (e.g., ultrasonic) welding), any thermal bonding technique (e.g., heat and/or pressure applied to one or both of the components to be coupled), other suitable coupling means, or combinations thereof. By way of example only, in the embodiment of FIGS. 1-25, the first portion 120 and the second portion 122 are configured to be ultrasonically welded together. In addition, the housing 102 is shown as being split along its length into the first portion 120 and the second portion 122; however, other configurations are possible that also facilitate assembly and/or use of the apparatus 100.

Figure 6:
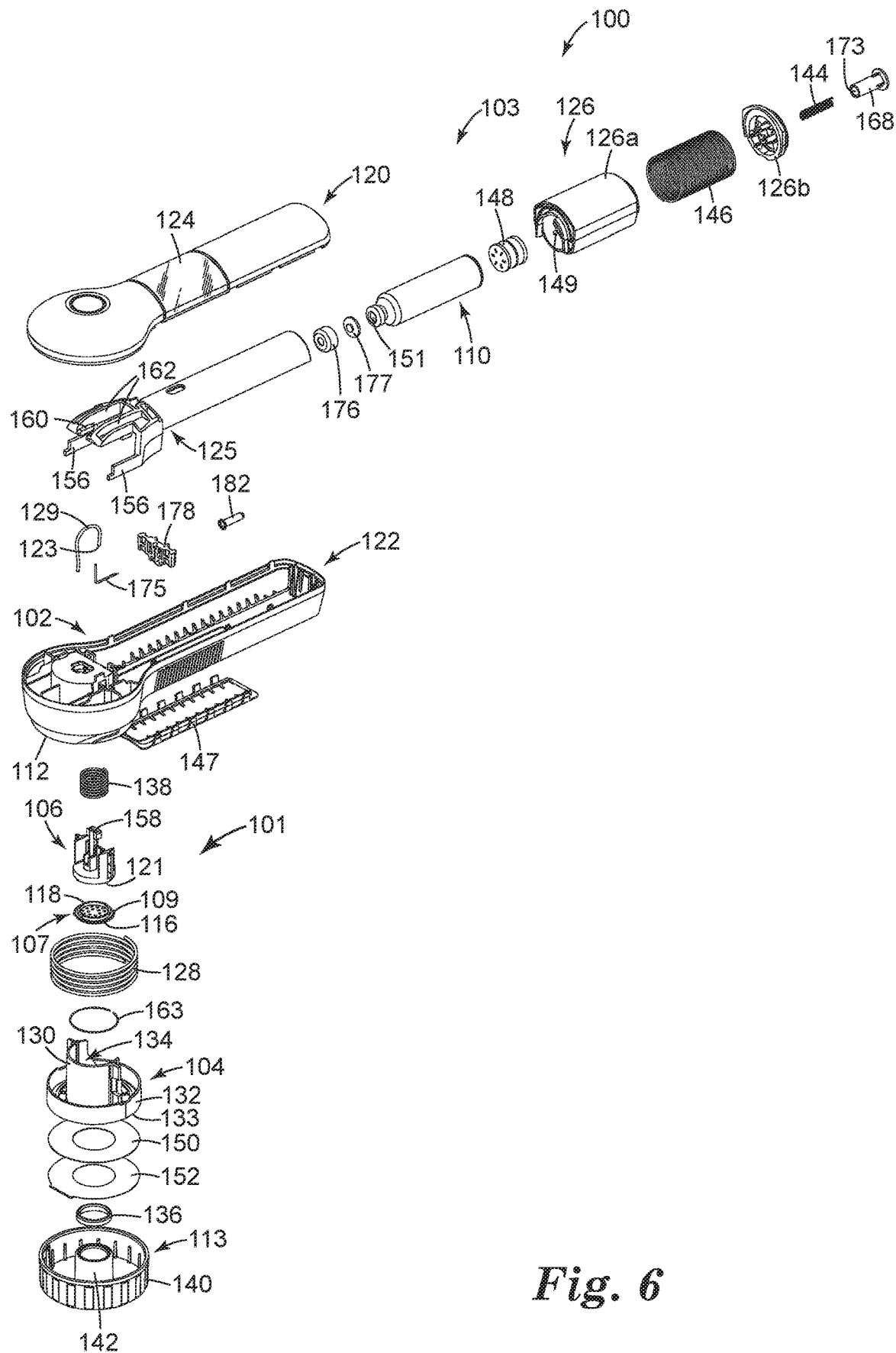
FIG. 6 is a front, top, exploded perspective view of the apparatus of FIGS. 1-5.
Figure 7:
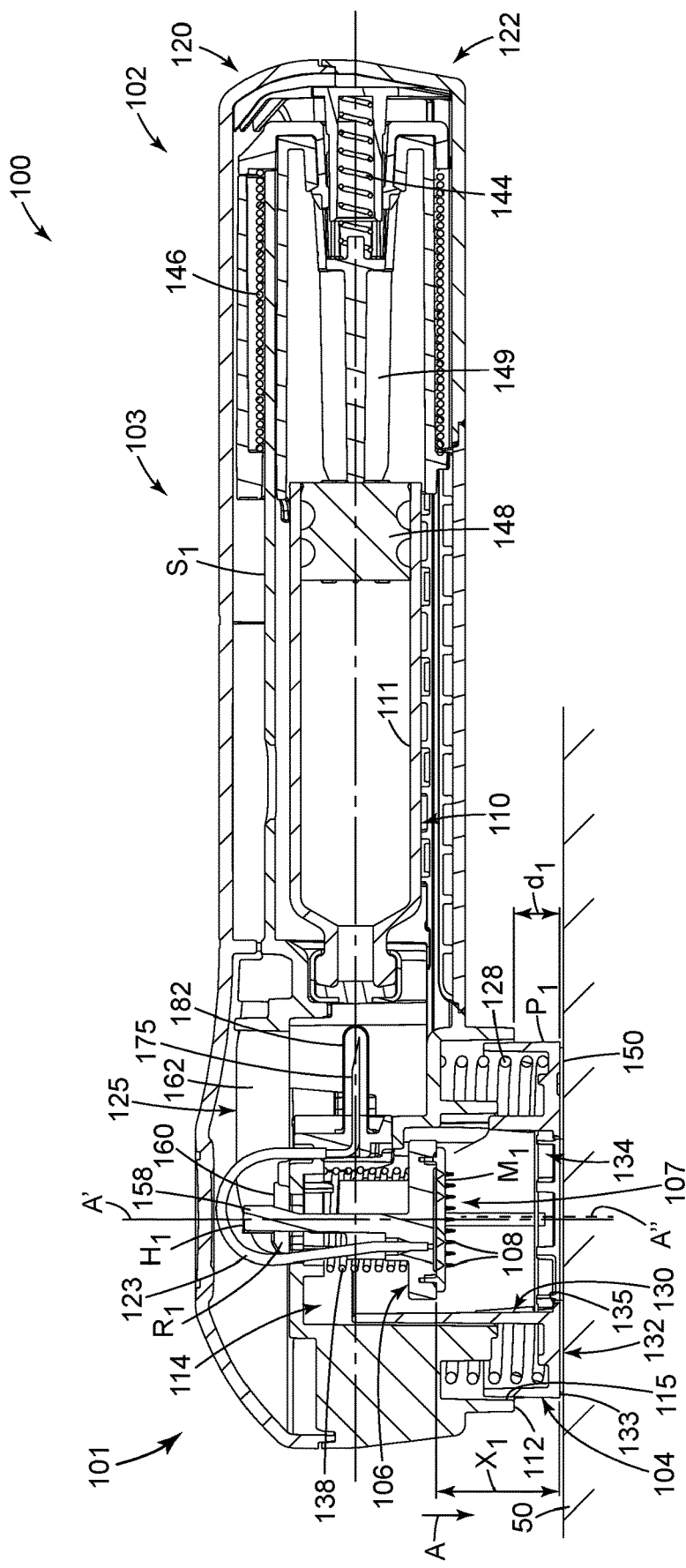
FIG. 7 is a side cross-sectional view of the apparatus of FIGS. 1-6, the apparatus shown in a first condition with the cover removed.

In some embodiments, the housing 102 (e.g., the second portion 122 of the housing 102) can include a base 112 (see, e.g., FIGS. 3-5) configured to be positioned toward a skin surface 50 (see, e.g., FIG. 7). The base 112 may be configured to touch the skin surface 50 during injection and/or infusion and may include a skin-contact adhesive. However, the base 112 of the embodiment illustrated in FIGS. 1-25 does not include an adhesive and is a non-adhesive surface. The base 112 of the housing 102 can extend along the entire length of the housing 102, but the base 112 of the housing 102 referenced herein is particularly referring to the base 112, or portion thereof, that is located adjacent the injection assembly 101 and the actuator 104 that projects outwardly with respect to the base 112, as described in greater detail below. Particularly, the base 112 of the housing 102 referenced herein is generally provided by or defined by a protrusion 119 that protrudes (e.g., downwardly) relative to the remainder of the housing 102 (see FIGS. 4 and 5).

In the accompanying figures, it appears that a rear or tail end of the apparatus 100 (e.g., adjacent the infusion assembly 103 and opposite where the injection assembly 101 is located) is raised off of the skin surface 50. While this may be the case, it is certainly possible that the tail end of the apparatus 100 would also rest against the skin surface 50 in use. For example, the rear end of the apparatus 100 can be angled down toward the skin 50 to facilitate resting the rear end on the skin 50. In addition, in some embodiments, the base 112 of the housing 102 in that region (or extending along the length of the apparatus 100) can further include a skin-contact adhesive and can be adhered to the skin. In addition, the protrusion 119 is shown by way of example only; however, it should be understood that the apparatus 100 can be configured not to include such a protrusion 119, and in some embodiments, the entire base 112 of the housing 102 can be flush with the skin 50 or be configured to be adhered to the skin, e.g., after actuation.

The housing 102 can further include or define a cavity (or chamber, or pocket, or recess, etc.) 114. As shown, the base 112 can define an opening 115 that opens into the cavity 114. Said another way, the cavity 114 can extend through the base 112 to define the opening 115. The housing 102, and particularly, the cavity 114 (or a portion thereof) can be configured to house at least a portion of the microneedle array holder 106 and the microneedle array 107 (e.g., when coupled to the holder 106), i.e., prior to application of the microneedles 108 to the skin 50.

The microneedle array holder 106 can be configured to be at least partially located in the cavity 114 of the housing 102 and can be configured to hold a microneedle array 107 within the cavity 114 of the housing 102. The microneedle array holder 106 can also be movable with respect to the housing 102 (i.e., with respect to the opening 115 in the housing 102) to deliver the microneedles 108 to a substrate of interest (e.g., skin). As shown in FIG. 6, the microneedle array holder 106 can include a first (or bottom) side (or base) 121 that can be configured to be positioned toward a skin surface, i.e., skin-facing, and which can be configured to receive the microneedle array 107. By way of example only, a microneedle array 107 can be coupled (e.g., removably coupled) to the microneedle array holder 106 by a variety of coupling means, including but not limited to, press-fit engagement (also sometimes referred to as "friction-fit engagement" or "interference-fit engagement"), snap-fit engagement, magnets, hook-and-loop fasteners, adhesives, cohesives, clamps, stitches, staples, screws, nails, rivets, brads, crimps, detents, welding (e.g., sonic (e.g., ultrasonic) welding), any thermal bonding technique (e.g., heat and/or pressure applied to one or both of the components to be coupled), other suitable coupling means, or combinations thereof.

The "microneedle array" 107 can include the microneedles 108 and any supporting structure or substrate used to support the microneedles 108 and/or to couple the microneedle array 107 to other structures or components of the apparatus 100, such as the microneedle array holder 106. For example, in some embodiments, the "microneedle array" 107 can include a substrate (or "carrier," or "base") 109 from which the microneedles 108 protrude, as well as additional layers or carriers. In the embodiment illustrated in FIGS. 1-25, the microneedles 108 are integrally formed with the substrate 109. However, it should be understood that additional layers can be employed in the microneedle array 107, and other suitable configurations are possible. For example, in some embodiments, the microneedles 108 can be formed directly into the substrate 109 which can then be coupled (e.g., mechanically and fluidly) to a base or additional layer.

In some embodiments, the apparatus 100 does not include the microneedle array 107, but rather, the apparatus 100 can be configured to hold the microneedle array 107 and to deliver the microneedle array 107 to the skin according to specified parameters, e.g., at a predetermined impact velocity and/or force. Such specified parameters, for example, can be used to ensure delivery of the microneedles 108 to a predetermined depth of penetration.

The microneedle array 107 (e.g., the substrate 109) can include a first side 116 comprising the microneedles 108 and a second side 118 opposite the first side 116. The first side 116 can include a first major surface (e.g., defined by the substrate 109 in the illustrated embodiment) from which the microneedles 108 protrude. The first side 116 can be oriented toward the base 112 of the housing 102 (i.e., positioned to face the skin surface 50). That is, a microneedle array 107 can be coupled to the microneedle array holder 106 such that the second side 118 faces the microneedle array holder 106, and the first side 116 is oriented toward the base 112 of the housing 102, i.e., positioned to face the skin surface 50, or be "skin-facing."

The housing 102, the actuator 104, the microneedle array holder 106 and/or the microneedle array 107 (e.g., the substrate 109), the cover 113, and the shuttle 125 can be formed of a variety of materials, including but not limited to, thermoset plastics (e.g., acetal resin available under the trade designation DELRIN® DuPont Corporation, Wilmington, Del.; other suitable thermoset plastics, or combinations thereof), thermoplastics (e.g., polyethylene, polypropylene, other suitable thermoplastics, or combinations thereof), or metals (e.g., stainless steel, aluminum, other suitable metals, or combinations thereof), or combinations thereof.

The actuator 104 can include an inner portion 130 configured to be received in (or extend into) the cavity 114 of the housing 102 and to interact and/or engage with the injection assembly 101 and the infusion assembly 103. The actuator 104 can further include an outer portion 132 coupled to the inner portion 130 and configured to extend out of the cavity 114 of the housing 102 and through the opening 115 of the housing 102, such that the outer portion 132 can protrude outwardly of the housing 102 and at least partially reside on the exterior of the housing 102 to allow a user to manually manipulate and control the actuator 104. For example, as shown, in some embodiments, the outer portion 132 can include or function as a button or other manually engageable portion or element. The outer portion 132 is illustrated by way of example as being a push-button. By way of further example, the inner portion 130 and the outer portion 132 of the actuator 104 of FIGS. 1-25 are integrally formed.

The actuator 104 can be movable with respect to the housing 102 (e.g., with respect to the opening 115 in the base 112 of the housing 102) and the microneedle array holder 106 between a first position $P_1$ (see FIGS. 3-5, 7 and 8) and a second position $P_2$ (see FIGS. 9-13, 16-17 and 22) to cause the microneedle array holder 106 to move, respectively, between (i) a first, retracted position $H_1$ (see, e.g., FIGS. 3, 4 and 7-12), in which the microneedle array 107 (when coupled to the microneedle array holder 106) is recessed within the housing 102 (and/or the actuator 104, as described below), such that the microneedle array 107 does not contact the skin 50 when the apparatus 100 is positioned on the skin 50; and (ii) a second, extended (or "impact" or "treatment") position $H_2$ (see, e.g., FIGS. 15-17 and 22), in which at least a portion of the microneedle array 107 (when coupled to the microneedle array holder 106) is positioned to contact the skin 50 (e.g., via the opening 115) when the apparatus is positioned on the skin 50.

Figure 13:
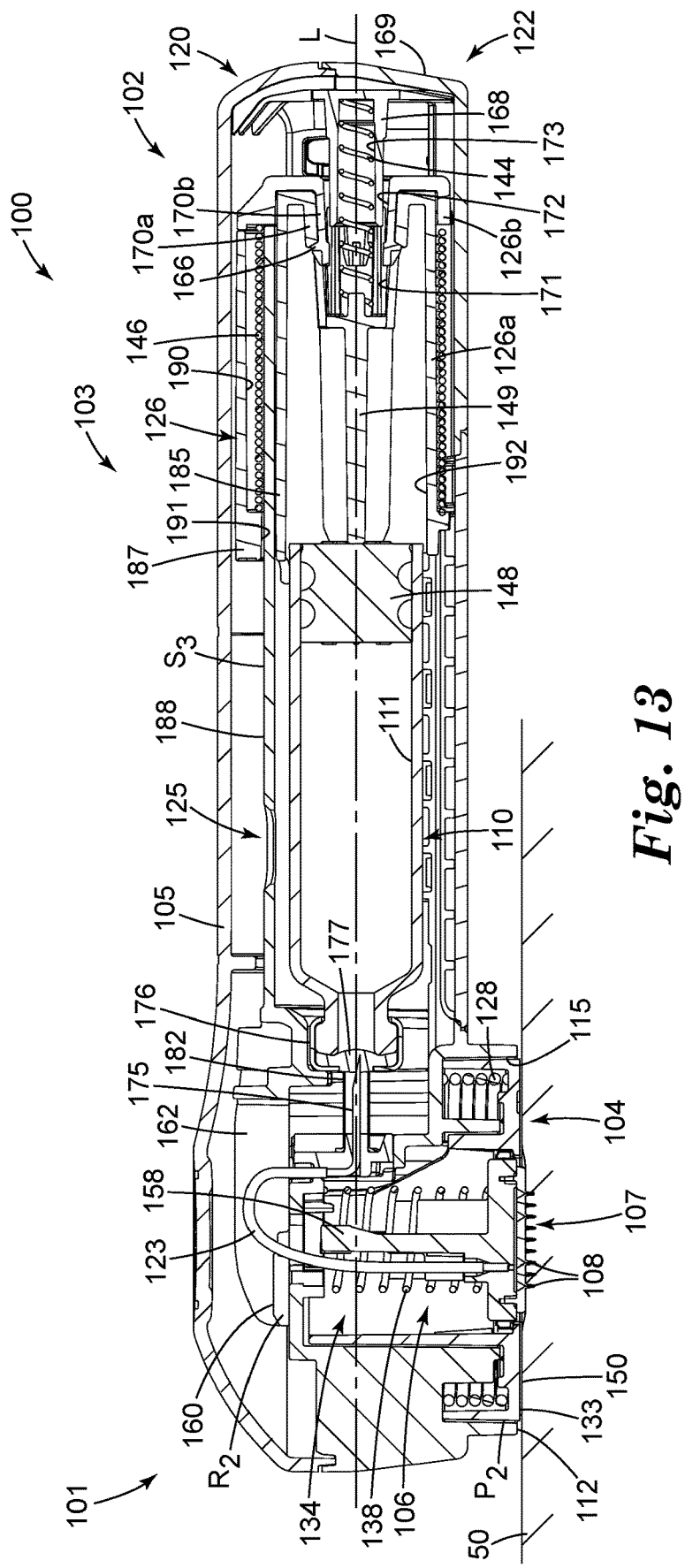
FIG. 13 is a side cross-sectional view of the apparatus of FIGS. 1-12, the apparatus shown in a fourth condition.
Figure 14:
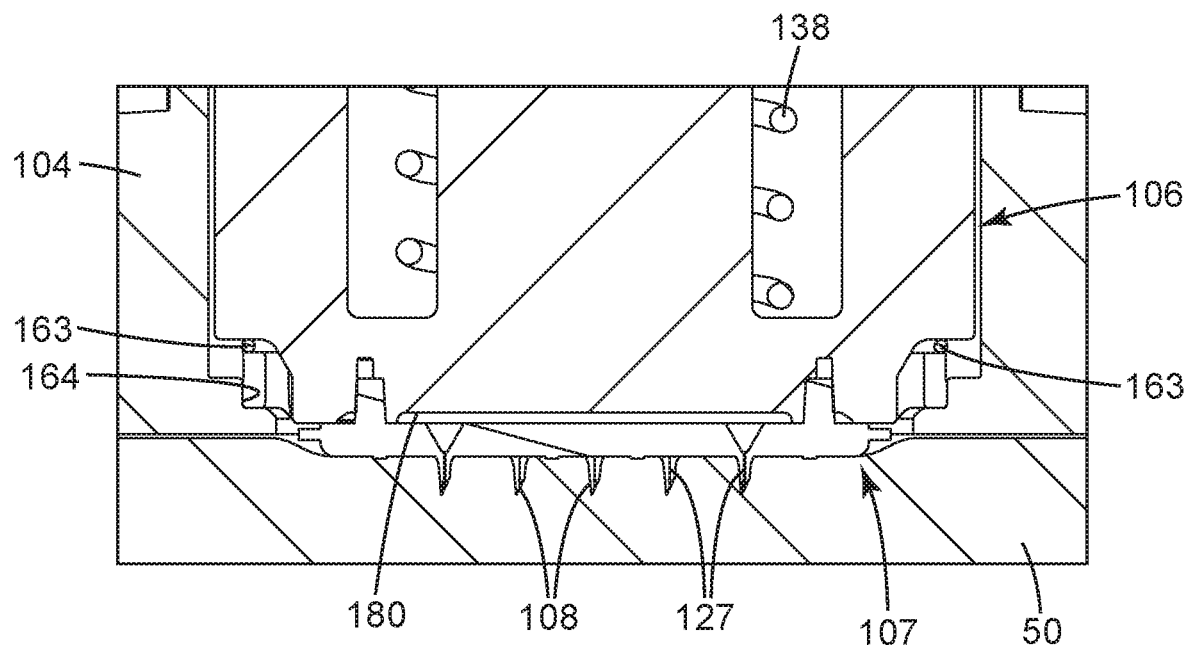
FIG. 14 is a close-up front cross-sectional view of the apparatus of FIGS. 1-13, the apparatus shown in the fourth condition.
Figure 15:
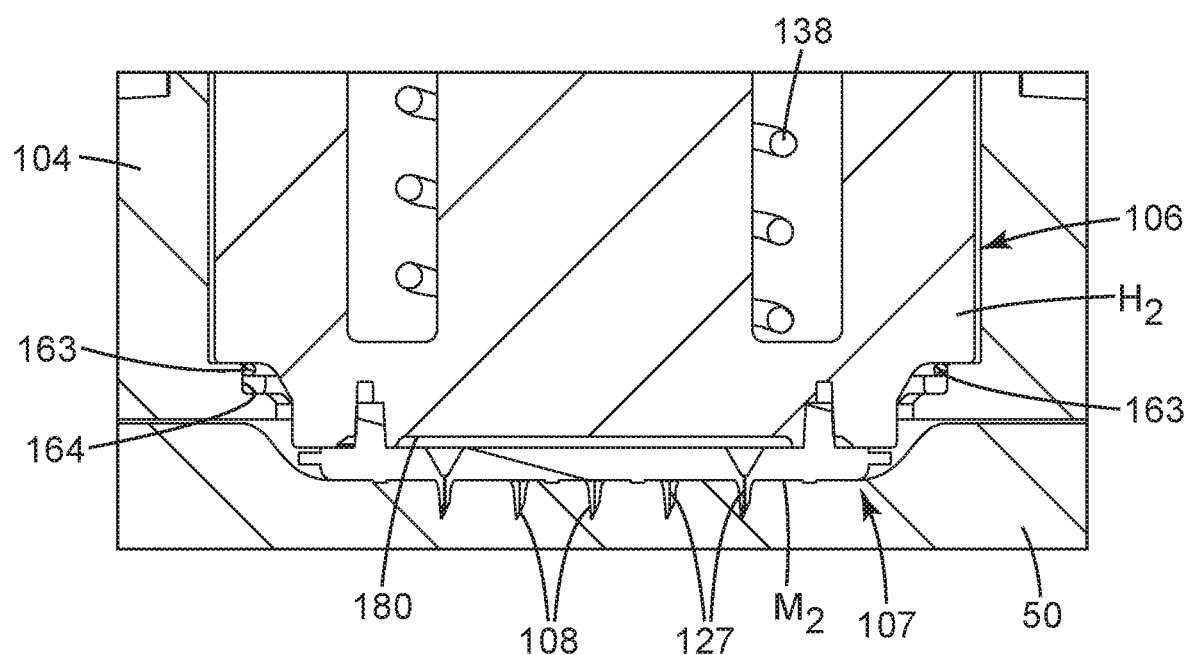
FIG. 15 is a close-up front cross-sectional view of the apparatus of FIGS. 1-14, the apparatus shown in a fifth condition.

In some embodiments, movement of the holder 106 from the retracted position $H_1$ to the extended position $H_2$ can be dampened by one or more dampeners or shock-absorbing elements or materials, which is illustrated in FIGS. 13-15 and described below with respect to a dampener 163, as shown in FIGS. 6, 14 and 15.

As shown, in some embodiments, the actuator 104 can be movable from its first position $P_1$ to its second position $P_2$ against the bias of a biasing element 128. As such, the actuator 104 can be biased in its first position $P_1$ (e.g., downwardly) and can require a user to overcome the bias of the biasing element 128 to actuate the apparatus 100. That is, the biasing force presented by the biasing element 128 represents the force a user would need to overcome in order to actuate the apparatus 100. This biasing force can be controlled so as not to be too high or too low. If the biasing force is too low, the apparatus 100 may be too sensitive and the apparatus 100 may be prematurely actuated, e.g., when a user merely intends to adhere the apparatus 100 to the skin 50. However, if the biasing force is too high, the apparatus 100 may not be able to be actuated by pressing it on soft skin. In some embodiments, the biasing force (e.g., provided by the biasing element 128), and therefore, also the actuation force of the apparatus 100 can be at least 5 N, in some embodiments, at least 6 N, and in some embodiments, is 8 N. In some embodiments, the biasing force (and hence, the actuation force) can be no greater than 15 N, in some embodiments, no greater than 12 N, and in some embodiments, no greater than 10 N.

As shown, the microneedle array holder 106 can be movable between the retracted position $H_1$ and the extended position $H_2$ independently of any portion of the infusion assembly 103, such as the cartridge 110 and the shuttle 125, which can minimize the amount of structure that needs to be moved to impact the skin 50 with the microneedles 108. That is, the injection assembly 103, and portions thereof, is generally not movable with the microneedle array holder 106 between the retracted $H_1$ and the extended position $H_2$. As a result, the injection assembly 101 can be decoupled from and operate separately of the infusion assembly 103, even though both the injection assembly 101 and the infusion assembly 103 can form a portion of the overall apparatus 100, allowing each assembly to be dedicated to their respective functions.

In some embodiments, the infusion assembly 103 (e.g., the shuttle 125 and the cartridge 110) can be configured not to move independently of the housing 102 any appreciable amount in a direction oriented normal or substantially normal with respect to the skin surface 50. That is, in some embodiments, the infusion assembly 103 can be configured not to move independently of the housing 102 toward or away from the skin surface 50 by any appreciable amount. As in the illustrated embodiment, in some embodiments, the infusion assembly 103 may move toward the skin surface 50 with the housing 102 as the apparatus 100 is actuated (e.g., when an inverted actuator 104 is employed), without the infusion assembly 103 moving separately from the housing 102 in this direction. In some embodiments, the infusion assembly 103 can be located in a portion (e.g., an elongated portion, such as a handle or extension) of the apparatus 100 that can be pressed toward the skin surface 50 along with the remainder of the apparatus 100 when the apparatus 100 is pressed toward the skin surface 50 to actuate the actuator 104. Even in such embodiments, the infusion assembly 103 can be configured not to move relative to the housing 102 in a direction toward or away from the skin surface 50.

The first, retracted position $H_1$ and the second, extended position $H_2$ can be spaced a distance from one another along an actuation axis A' (see FIGS. 3, 7 and 16), such that the microneedle array holder 106 is movable along the actuation axis A', e.g., relative to the housing 102 and the actuator 104 (e.g., after the actuator 104 has been moved to its second position $P_2$), between the first, retracted position $H_1$ and the second, extended position $H_2$.

The actuation axis A' can generally be oriented substantially normal with respect to the skin surface 50 (and the first side 121 of the holder 106, as well as the first side 116 of the microneedle array 107 when coupled to the holder 106), but this need not be the case. Rather, in some embodiments, the actuation axis A' can be arcuate or define otherwise nonlinear path(s), etc. The actuation axis A' simply refers to movement between the first, retracted position $H_1$ and the second, extended position $H_2$.

The actuator 104 can further include a base 133 that is configured to be positioned toward the skin surface 50, and a cavity (or chamber, or recess, or pocket, or bore) 134 that extends through the base 133 of the actuator 104 to form an opening 135 (see, e.g., FIG. 7) in the base 133 of the actuator 104. The base 133 can be at least partially defined by the outer portion 132 of the actuator 104, and the cavity 134 can be at least partially defined by the inner portion 130 that is dimensioned to be received in the cavity 114 of the housing 102.

Figure 9:
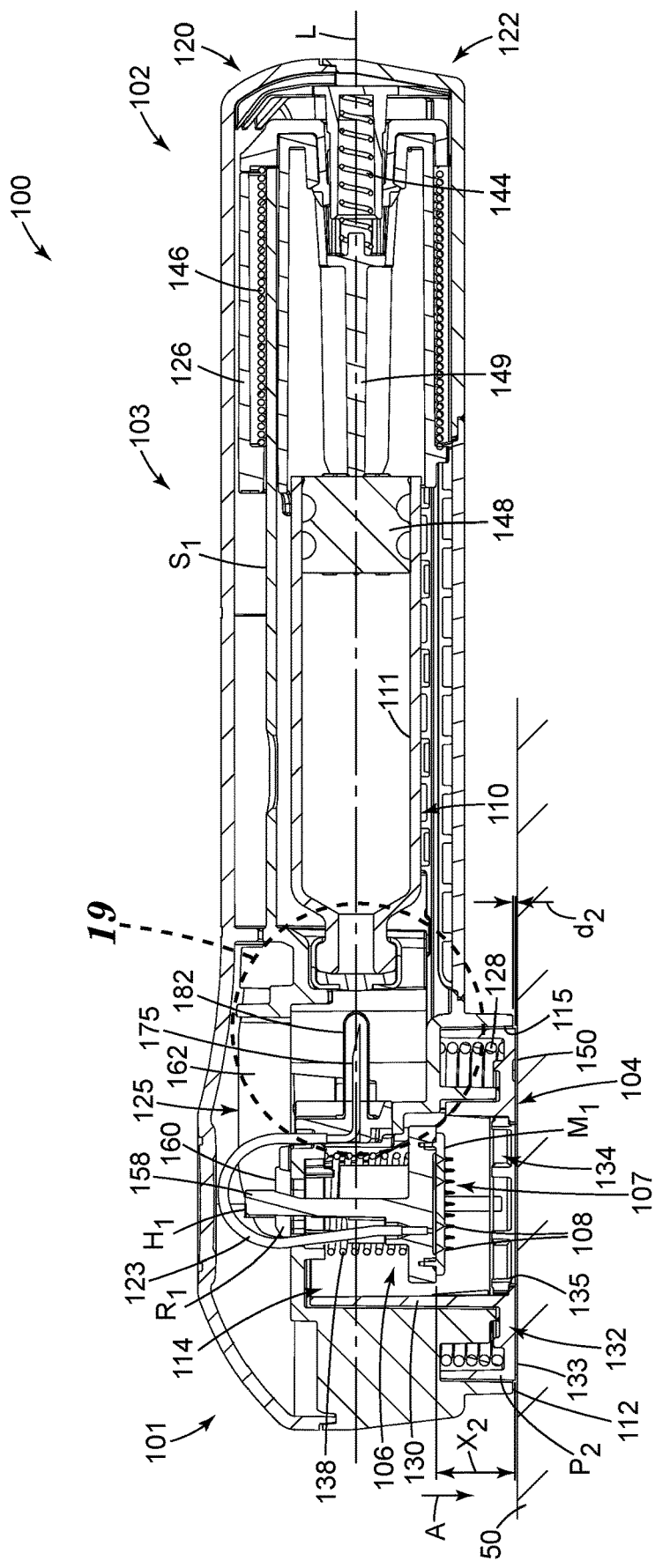
FIG. 9 is a side cross-sectional view of the apparatus of FIGS. 1-8, the apparatus shown in a second condition.

As can be seen by comparing FIGS. 7 and 9, in some embodiments, the actuator 104 (e.g., the base 133 thereof) can be movable with respect to the base 112 of the housing 102, such that when the actuator 104 is in the first position $P_1$, an outermost surface (e.g., the base 133) of the actuator 104 can extend beyond the base 112 of the housing 102 by a first distance $d_1$ (e.g., see FIG. 7); and when the actuator 104 is in the second position $P_2$, the outermost surface of the actuator 104 either no longer extends beyond the base 112 of the housing 102 (e.g., is flush with, or recessed relative to, the base 112), or the outermost surface of the actuator 104 extends beyond the base 112 of the housing 102 by a second distance $d_2$ (e.g., see FIG. 9) that is less than the first distance $d_1$. That is, in some embodiments, the actuator 104 can be movable between the first position $P_1$ and the second position $P_2$ with respect to the base 112 of the housing 102, into and out of the opening 115 formed in the base 112 of the housing 102. Said another way, in some embodiments, when the actuator 104 is in the first position $P_1$, at least a portion of the actuator 104 can protrude from or through the opening 115 in the base 112 of the housing 102 and can define a first surface (e.g., the base 133) configured to be coupled to the skin surface 50. Such a first surface can include a skin-contact adhesive 150, as described below.

The configuration of the actuator 104 is shown by way of example only as being located on a skin-facing surface of the apparatus 100, i.e., adjacent the base 112 of the housing 102. Said another way, the outer (engageable) portion 132 of the actuator 104 is shown as being located on and protruding from a lower portion (i.e., the second portion 122) of the housing 102. That is, the actuator 104 is an example of an 'inverted actuator,' as compared to conventional systems, where the actuator 104 is located on an underside of the apparatus 100. Such a configuration allows for facile operation of the apparatus 100 and particularly allows for the actuator 104 to be moved from the first position $P_1$ to the second position $P_2$ in response to the apparatus 100 being pressed toward the skin surface 50 by pressing on a nonskin-facing, or upper, portion of the apparatus 100. Such a non-skin-facing, or upper, portion of the apparatus 100 (e.g., of the housing 102) need not be located directly opposite the actuator 104. That is, the non-skin-facing, or upper, portion can be located in an off-axis position with respect to a central longitudinal or actuation axis of the actuator 104. Such an 'inverted actuator' is further described in PCT Publication No. WO 2014/193729, which is incorporated herein by reference.

The term "off-axis" generally refers to a position, direction, or axis of movement, that is not aligned with the central longitudinal or actuation axis of the actuator 104. For example, the actuator 104 can move from the first position $P_1$ to the second position $P_2$ in a first direction, along an actuation axis A" (see FIG. 7), which, in the embodiment illustrated in FIGS. 1-25, is also its central longitudinal axis. Such actuation or movement of the actuator 104 can be caused by a force exerted along a second direction that is not directly opposite the second direction or that is not aligned with the actuation axis A" of the actuator 104. Rather, such movement of the actuator 104 can be caused by a force that is oriented at an oblique angle with respect to the actuation axis A" of the actuator 104. In some embodiments, the second direction or axis can intersect the first direction or the actuation axis A" of the actuator 104 (e.g., at an oblique angle), or the second direction or axis can be parallel with respect to the central longitudinal axis of the actuator 104 without being directly in line with the actuation axis A".

By allowing for off-axis actuation of the apparatus 100, the apparatus 100 can offer more reliable actuation, enhanced user comfort and enhanced ergonomics, for example, if the apparatus 100 can be actuated without requiring that a user engage or manipulate a specific location or element on the apparatus 100. For example, at least a portion (e.g., the first (upper) portion 120 of the housing 102) can be configured to be pressed toward the skin 50 using any portion of a hand, such as a user's palm or fist, as opposed to requiring the precise dexterity of finger manipulation. Such a configuration can provide an advantage, for example, for arthritic and/or elderly patients. In addition, off-axis actuation allows for actuation of the apparatus 100 in a variety of ways, as opposed to only a single option, that are clearly understood by a user, e.g., by an intuitive design or configuration.

While the 'inverted actuator' 104 of the illustrated embodiment is shown as also providing the opening 135 through which the microneedle array 107 will be deployed to impact and penetrate a skin surface, in some embodiments, an inverted actuator can still be employed, i.e., on an underside or skin-facing side of the apparatus 100 and housing 102, without the actuator 104 also defining a cavity 134 or opening 135 through which the microneedle array 107 and microneedle array holder 106 move (as is the case in the illustrated embodiment, as described below). That is, in some embodiments, the actuator 104 can still be inverted but not positioned directly adjacent the opening through which the microneedles 108 extend when the microneedle array holder 106 is in its extended position $H_2$. Particular advantages, however, can result from employing an actuator 104 such as that illustrated where the microneedle array holder 106 is movable within the cavity 134 of the actuator 104 as well, such as a compact design.

In some embodiments, as shown in the illustrated embodiment, the actuator 104 can be configured so as to be located only in a portion of the apparatus 100, which can localize the actuation of the apparatus 100 to a precise area, even without requiring precise user manipulation to actuate the apparatus 100. For example, as shown, in some embodiments, the overall apparatus 100 can have or define a first footprint having a first area, and the actuator 104 can have a second footprint having a second area, and the second area can be less than the first area. In some embodiments, the second area can be less than half (i.e., less than 50%) of the first area. In some embodiments, the second area can be less than a quarter (i.e., less than 25%) of the first area.

As shown in FIGS. 1-6 and 24-25, the cover 113 can be configured to cover the opening 115 in the base 112 of the housing 102. As shown in FIGS. 3-6 and described in greater detail below with respect to FIGS. 24 and 25, in some embodiments, the cover 113 can be a 'dual cover' that includes a first portion 140 configured to cover at least a portion of the base 112 of the housing 102 adjacent the opening 115, and a second portion 142 configured to be at least partially received in the cavity 114 of the housing 102 and further configured to cover the plurality of microneedles 108 on the microneedle array 107. In embodiments such as the illustrated embodiment that employ an 'inverted actuator' 104, the cover 113 can further be configured to cover the opening 135 to the cavity 134 of the actuator 104 (see, e.g., FIG. 3). The cover 113 (e.g., the second portion 142 thereof) can be configured to maintain the sterility of the microneedles 108 and the fluid path 123. In embodiments in which the microneedle array 107 will be deployed via the opening 135 in the actuator 104, the cover 113 (e.g., the first portion 140 thereof) can also be configured to cover and protect the actuator 104 prior to use, and can be used to inhibit or prevent accidental premature actuation of the actuator 104. In embodiments in which the microneedle array 107 will deployed via the opening 115 in the housing 102 but not necessarily the opening 135 in the actuator 104, the cover 113 (e.g., the first portion 140 thereof) can be configured to cover and protect at least the portion of the base 112 of the housing 102 that is configured to be coupled to a skin surface. The cover 113 is further described in PCT Publication No. WO 2014/193727, which is incorporated herein by reference.

Figure 4:
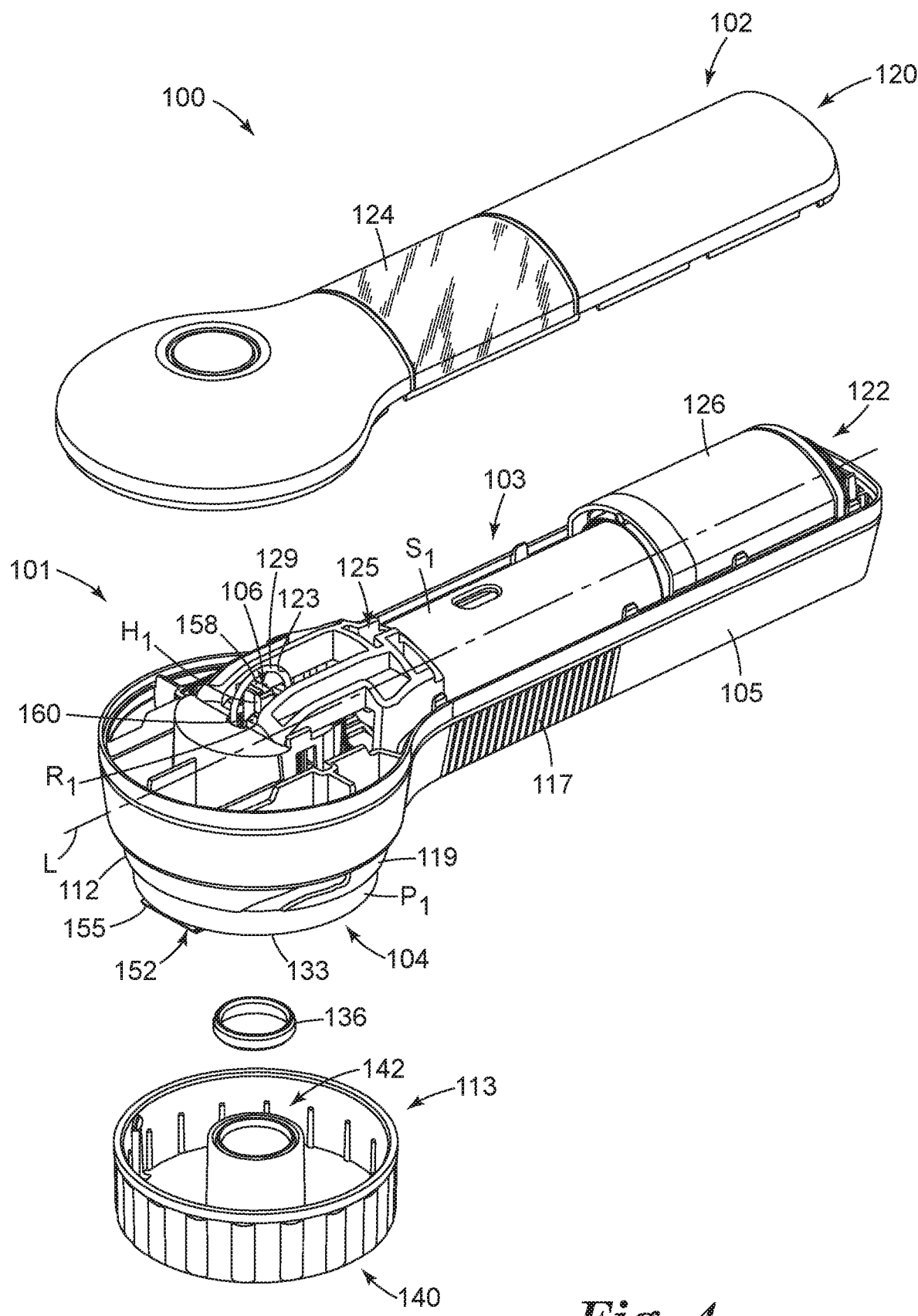
FIG. 4 is a front, top, partially exploded perspective view of the apparatus of FIGS. 1-3.
Figure 5:
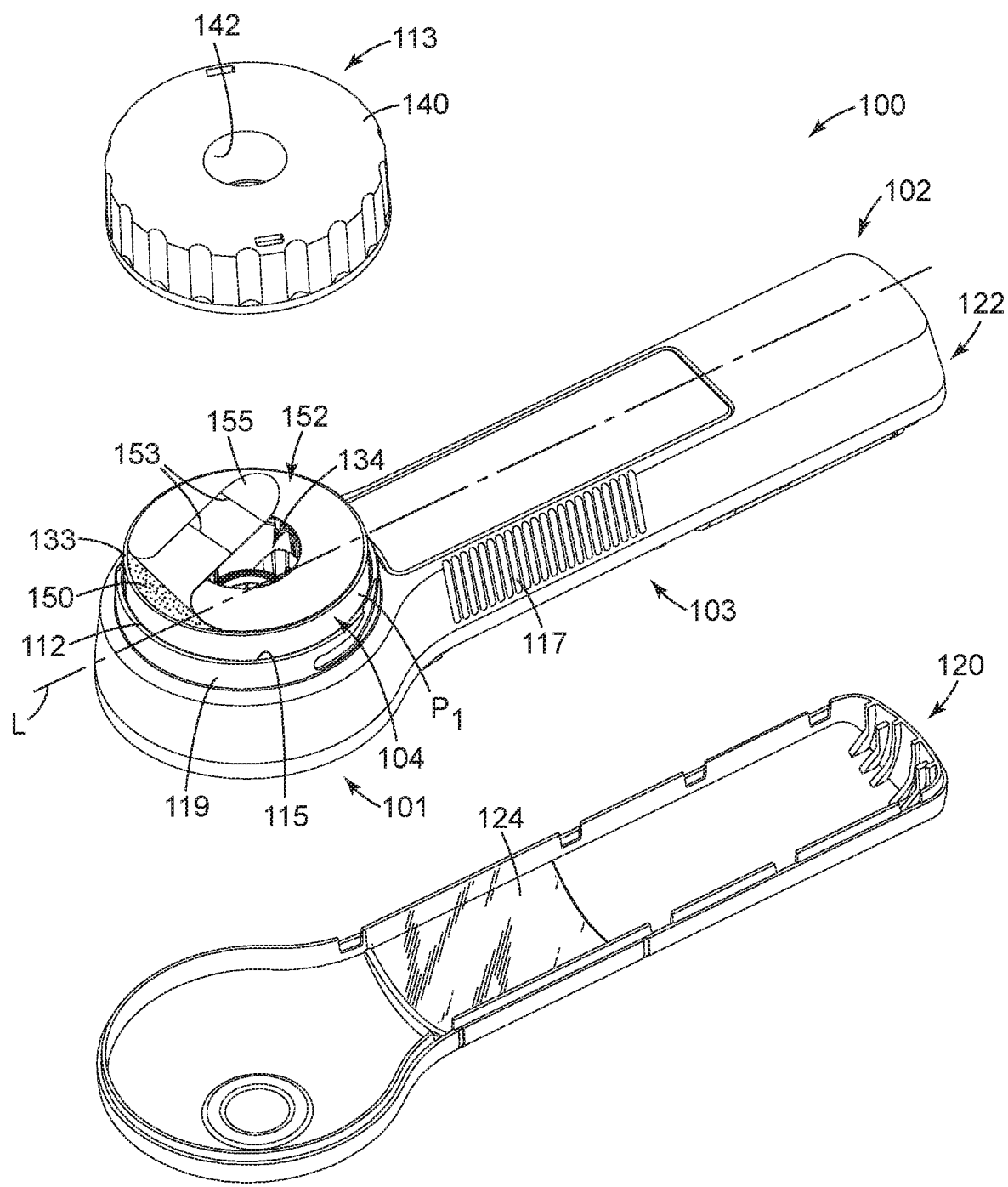
FIG. 5 is a front, bottom, partially exploded perspective view of the apparatus of FIGS. 1-4.

As shown in FIG. 5, in some embodiments, the base 133 of the actuator 104 can include the skin-contact adhesive 150 (described in greater detail below), and the apparatus 100 can further include an optional release liner 152 (described in greater detail below), which can protect the skin-contact adhesive 150 prior to use and during assembly, storage and shipment of the apparatus 100. The release liner 152 can be removed prior to applying the apparatus 100 to skin. The release liner 152 can be configured to release, or can be configured to present release characteristics to, the skin-contact adhesive 150, so that the apparatus 100 can be coupled to the release liner 152 during storage and shipment, and can be easily separated from the release liner 152 during application of the apparatus 100. By way of example only, the release liner 152 can include a tab 155 (see FIGS. 4 and 5) positioned to facilitate removing the release liner 152 from the skin-contact adhesive 150 when desired. As shown, the tab 155 can include one or more folds 153 to allow the tab 155 to be shortened during storage but lengthened when desired to facilitate removal of the release liner 152.

In use, the release liner 152 can be removed (if employed) from the skin-contact adhesive 150, and the adhesive base 133 of the actuator 104 can be coupled to the skin 50. Actuation of the actuator 104 can occur immediately following coupling of the base 133 of the actuator 104 to the skin 150 or even substantially simultaneously with coupling the base 133 to the skin 150. The base 133 of the actuator 104 (or the base 112 of the housing 102, if the skin-facing actuator 104 is not employed) can remain coupled to the skin 50 throughout injection and infusion. As a result, in some embodiments, the apparatus 100 can be configured to be "worn" by a patient during infusion/injection of fluid into the skin 50. In such embodiments, the apparatus 100 may be directly applied to a patient's skin 50 to accommodate ambulatory movement while keeping the microneedles 108 at an appropriate penetration depth(s). That is, even in embodiments in which the housing 102 itself does not include the skin-contact adhesive 150, the housing 102 (i.e., the apparatus 100 as a whole, including the actuator 104, the housing 102, and the elements of the infusion assembly 103) can be configured to remain coupled to the skin surface 50 after the microneedle array 107 has punctured the skin 50 and during infusion. For example, in such embodiments, the housing 102 can be configured to be adhered to the skin 50 via the skin-contact adhesive 150 on the actuator 104.

In embodiments in which the actuator 104 is not located on an underside or on a skin-facing portion of the apparatus 100 (or housing 102), the base 112 of the housing 102 can include the skin-contact adhesive 150 and optional release liner 152. In addition, any description herein regarding positioning the base 133 of the actuator 104 on the skin surface 50 can instead be interpreted to be referring to positioning the base 112 of the housing 102 on the skin surface 50. Similarly, any description regarding movement of the microneedle array holder 106 within the cavity 134 of the actuator 104 may still apply if the actuator 104 is not located on a skin-facing portion of the apparatus 100, depending on the relative configuration of these components. Furthermore, in embodiments in which the actuator 104 is inverted as shown in the illustrated embodiment, the base 133 of the actuator 104 can be configured to contact (and adhere to, via the skin-contact adhesive 150) the skin 50 when the apparatus 100 is positioned on the skin surface 50. In embodiments in which the actuator 104 is not inverted, the base 112 of the housing 102 can be configured to contact (and adhere to) the skin 50 when the apparatus 100 is positioned on the skin surface 50.

In some embodiments, as shown, the microneedle array holder 106 can be located in and movable in the cavity 134 of the actuator 104 between the retracted position $H_1$ and the extended position $H_2$. As such, in some embodiments, the actuator 104 can be configured to at least partially surround the microneedle array 107 when the microneedle array 107 is coupled to the holder 106, at least when the holder 106 is in the extended position $H_2$. In some embodiments, the actuator 104 can be configured such that at least a portion of the actuator 104 (e.g., the outer portion 132) surrounds the microneedle array 107 (and/or the microneedle array holder 106) on all sides, or encircles the microneedle array 107 (and/or the microneedle array holder 106), at least when the microneedle array holder 106 is in the extended position $H_2$.

As shown in FIGS. 7 and 9, in embodiments in which the actuator 104 is inverted and located adjacent the same opening 115 through which the microneedle array 107 will contact the skin 50, and when the actuator 104 is in the first position $P_1$ and the microneedle array holder 106 is in the retracted position $H_1$, the base 133 of the actuator 104 can be positioned a first distance $x_1$ from the first side (or base) 121 of the microneedle array holder 106 (and/or the first side (or base) 116 of the microneedle array 107)—see FIG. 7. When the actuator 104 is in the second position $P_2$ the base 133 of the actuator 104 can be positioned a second distance $x_2$ from the first side (or base) 121 of the microneedle array holder 106 (and/or the first side (or base) 116 of the microneedle array 107)—see FIG. 9—and the second distance $x_2$ can be less than the first distance $x_1$. As a result, the distance between the base 133 of the actuator 104 and the first side 121 of the microneedle array holder 106 (or the first side 116 of the microneedle array 107) can decrease when the actuator 104 is moved from the first position $P_1$ to the second position $P_2$.

By way of example only, in the embodiment illustrated in FIGS. 1-25, at least a portion of the cavity 114 in the housing 102 can have the shape of a cylindrical bore, at least a portion of the actuator 104 can include an annular cross-sectional shape (e.g., when the cross-section is taken substantially parallel with respect to the base 133), and the inner portion 130 of the actuator 104 can be substantially tubular in shape and be dimensioned to be received in the cylindrical bore-shaped cavity 114 of the housing 102. In addition, the cavity 134 defined at least partially by the inner portion 130 of the actuator 104 can have the shape of a cylindrical bore. By way of example only, the central longitudinal axes of the bore-shaped cavities 114 and 134 defined by the housing 102 and the actuator 104, respectively, can be substantially aligned, and the actuation axis A' (see FIGS. 3, 7 and 16) of microneedle array holder 106 can also be substantially aligned with the central longitudinal axes of the cavities 114 and 134.

In some embodiments, the actuation axis A' and the central longitudinal axes of the cavities 114 and 134 may not all be exactly aligned but can be substantially parallel with respect to one another. In some embodiments, the actuation axis A' of the holder 106 can be oriented substantially parallel with respect to the actuation axis A" of the actuator 104, as shown in the illustrated embodiment. Furthermore, in some embodiments, as shown, the actuation A' of the holder 106 can be substantially aligned (i.e., in line with) with the actuation axis A" of the actuator 104.

When the microneedle array holder 106 is in the first, retracted position $H_1$, the holder 106 can be recessed within the housing 102 and the actuator 104, such that the holder 106 (and the microneedle array 107, when coupled to the holder 106) does not extend beyond the base 112 of the housing 102 or the base 133 of the actuator 104. The microneedle array 107 can be movable with the holder 106 along the entire distance between the holder's retracted and extended positions $H_1$ and $H_2$. That is, when the microneedle array holder 106 is in the first, retracted position $H_1$ and a microneedle array 107 is coupled to the holder 106, the microneedle array 107 can also be in a first, retracted position $M_1$ (see, e.g., FIGS. 3, 7, 9 and 11), e.g., in which the microneedle array 107 is recessed within the housing 102 and the actuator 104 such that the microneedle array 107 does not contact (or is not positioned to contact) the skin surface 50 when the base 133 of the actuator 104 (or the base 112 of the housing 102 in embodiments in which the actuator 104 is located in a different location than adjacent the base 112 of the housing 102) is positioned on the skin surface 50. The microneedle array 107 can be housed within the cavity 114 of the housing 102 and the cavity 134 of the actuator 104, and can be recessed with respect to the base 112 of the housing 102 and the base 133 of the actuator 104 in its retracted position $M_1$.

Furthermore, when the microneedle array holder 106 is in the second, extended position $H_2$ and a microneedle array 107 is coupled to the holder 106, the microneedle array 107 can also be in a second, extended position $M_2$ (see, e.g., FIGS. 15-17 and 22), e.g., in which at least a portion of the microneedle array 107 is positioned to contact the skin surface 50 when the base 133 of the actuator 104 is positioned on the skin surface 50.

When the microneedle array holder 106 and the microneedle array 107 are in their respective second positions $H_2$ and $M_2$, at least a portion of the microneedle array 107 (and, potentially, a portion of the microneedle array holder 106) can extend beyond the base 133 of actuator 104 (or the base 112 of the housing 102 if an inverted actuator 104 is not employed). However, this need not be the case, and in some embodiments, it can be preferred for this not to be the case. Rather, in some embodiments, the microneedles 108 can be positioned close enough to the base 133 of the actuator 104 (while still being recessed within the housing 102 and the actuator 104 and without extending beyond the base 133 of the actuator 104), such that when the base 133 is pressed onto the skin surface 50, the skin 50 is caused to deform or dome up through the opening 135 of the actuator 104 and into the cavity 134 to a position where the skin 50 is contacted by the microneedles 108.

Portions of the housing 102 defining the cavity 114 and/or portions (e.g., the inner portion 130) of the actuator 104 defining the cavity 134 can retain and/or guide the microneedle array holder 106 for displacement along a path generally perpendicular to the base 133 of the actuator 104 (and/or the base 112 of the housing 102), as indicated by arrow A in FIG. 7. The actuation axis A' of the microneedle array holder 106 can be generally normal or perpendicular to that of the longitudinal axis L of the apparatus 100. While in one exemplary embodiment, the motion of holder 106 may be at substantially 90 degrees with respect to the base 133 (and/or the base 112), it will be appreciated that the generally normal path may deviate from 90 degrees to assume orientations that can penetrate deep enough to deliver an intended dosage.

The microneedle array holder 106 (and a microneedle array 107 coupled thereto) can be movable from the retracted position $H_1$ (and $M_1$) to the extended position $H_2$ (and $M_2$) by a first stored energy device 138 that is actuatable to release its potential energy for applying force to the microneedle array holder 106 in a direction generally normal to the base 133 (and/or the base 112), for example, downwardly, toward the skin surface 50. In some embodiments, such actuated force allows for movement of the holder 106 in a controlled manner, thereby ensuring application of the necessary forces for hollow microneedles 108 to penetrate the skin of a patient. As a result, the apparatus 100 can reliably and consistently deliver the microneedle array 107 to the skin at a desired impact velocity, e.g., to achieve the desired depth(s) of penetration.

In some embodiments, the first stored energy device 138 can be actuatable to apply force to the holder 106 to achieve a velocity of the microneedle array 107 before impact (i.e., before the microneedle array 107 held by the holder 106 impacts a patient's skin) ranging from between about 2 and about 20 m/s. More typically, the microneedle array 107 can strike a patient's skin at a velocity before impact ranging from between about 4 and about 12 m/s, in some embodiments, at a velocity before impact of at least 5 m/s, and in some embodiments, at a velocity before impact of about 6 m/s.

In some embodiments, the first stored energy device 138 can include a biasing element (e.g., a spring), and is shown as a coil spring by way of example only in the illustrated embodiment. However, stored energy devices of the present disclosure can include at least one stored energy device from a group consisting of: biasing elements (e.g., springs), propellants, chemicals, motors, electrical devices, and combinations thereof.

The microneedle array holder 106 is biased downwardly in the apparatus 100, toward its extended position $H_1$. As a result, the microneedle array 107, when coupled to the holder 106 is also biased toward its extended position $M_1$. The microneedle array holder 106 is primed, or held under load or against the bias (e.g., when a biasing element is employed as the stored energy device 138) when in the retracted position $H_1$, such that when the microneedle array holder 106 is released from being held, the stored energy device 138 will provide the forces to move the microneedle array holder 106 to its extended position $H_2$, and particularly, at a desired velocity.

In some embodiments, a portion of the actuator 104 can hold the microneedle array holder 106 in its retracted position $H_1$ until the actuator 104 has been moved to its second position $P_2$, at which point the actuator 104 no longer holds the microneedle array holder 106, and the microneedle array holder 106 is free to be driven by the stored energy device 138.

However, in some embodiments, as shown in the illustrated embodiment, an intermediate component, i.e., between the actuator 104 and the holder 106, can be actuated to move (or be released) by moving the actuator 104 to its second position $P_2$, and when that intermediate component is actuated or allowed to move, it moves to a position in which it no longer retains the holder 106 in its retracted position $H_1$, and the microneedle array holder 106 is free to be driven by the stored energy device 138. As a result, in some embodiments, the microneedle array holder 106 is held within the housing 102 in its retracted position $H_1$ by an element, component or structure of the apparatus 100 other than the actuator 104.

In the illustrated embodiment, that intermediate component is an element of the infusion assembly 103, namely, the shuttle 125. The shuttle 125 can be movable (e.g., substantially along the longitudinal axis L of the apparatus 100) between:

(i) a first, non-infusing, position $S_1$ (see, e.g., FIGS. 3, 4 and 7-10) in which the reservoir 111 of the cartridge 110 is not in fluid communication with the fluid path 123 (i.e., in which the cartridge 110 is fluidly isolated), and (ii) a second, infusing, position $S_2$ (see, e.g., FIGS. 17 and 22) in which the reservoir 111 of the cartridge 110 is in fluid communication with the fluid path 123.

As a result, in some embodiments, movement of the actuator 104 to its second position $P_2$ (i.e., "actuation" of the actuator 104) can actuate both (i) movement of the shuttle 125 (i.e., the cartridge 110) to its second position $S_2$ and movement of the microneedle array holder 106 to the extended position $H_2$.

Because the shuttle 125 of the illustrated embodiment is configured to hold and carry the cartridge 110, the first and second position $S_1$ and $S_2$ of the shuttle 125 also define positions of the cartridge 110. As a result, the positions of the shuttle described herein can also refer to positions of the cartridge 110.

The shuttle 125 can be primed or held under a load in its first position $S_1$ and can be biased toward its second position $S_2$, such that when the shuttle 125 is released by the actuator 104, the shuttle is free to move and begins moving toward its second position $S_2$. Employing the separate shuttle 125 that carries the cartridge 110 and operates intermediately between the actuator 104 and the microneedle array holder 106 can provide a sequence of events that ensures a sufficient delay between impact (i.e., movement of the microneedle array holder 106 to its extended position $H_2$)

and infusion (e.g., at least when the shuttle 125 is moved to its second position $S_2$ where fluid communication is established between the reservoir 111 and the fluid path 123). That is, the microneedle array holder 106 can be moved to its extended position $H_2$ before the shuttle 125 has completed its movement to its second position $S_2$. In some embodiments, as is the case in the illustrated embodiment, the shuttle 125 can begin moving to its second position $S_2$ before the microneedle array holder 106 may reach its extended position $H_2$, but the apparatus 100 can be configured such that the shuttle 125 will not have fully reached its second position $S_2$ (i.e., the point of establishing fluid communication between the cartridge 110 and the fluid path 123) before the microneedle array 107 has punctured the skin 50.

Said another way, even though the actuator 104 actuates movement of both the shuttle 125 and the microneedle array holder 106, the microneedle array holder 106 can be in its extended position $H_2$ when the shuttle 125 reaches its second position $S_2$, such that there is a lag or delay between when the microneedle array 107 is inserted into the skin 50 and when the reservoir 111 is placed in fluid communication with the microneedle array 107. If this were not the case, active agent could begin leaking out of the microneedles 108 prior to the microneedles 108 penetrating the skin 50. In some embodiments, this lag can accommodate a period of time in which the microneedle array 107 may undergo some undulating motion as it impacts the skin 50, which can be about 8 to about 10 milliseconds. Generally, it can be advantageous to provide fluid communication between the fluid path 123 and the cartridge 110 after the microneedle array 107 (and holder 106) has reached a steady state condition and is no longer bouncing on the skin surface 50.

The shuttle 125 can be configured to movable between its first position $S_1$ and its second position $S_2$ in a direction or along an axis that is oriented at a non-zero angle with respect to the actuation axis A' of the holder 106 and/or the actuation axis A" of the actuator 104. That is, in some embodiments, he microneedle array holder 106 can be movable between the retracted position $H_1$ and the extended position $H_2$ along a first axis (i.e., its actuation axis A'), the actuator 104 can be movable between the first position $P_1$ and the second position $P_2$ along a second axis, and the shuttle 125 can be movable between the first position $S_1$ and the second position $S_2$ along a third axis, and the third axis can be oriented at a non-zero angle with respect to one or both of the first axis and the second axis. Particularly, in embodiments employing a low profile configuration in which the shuttle 125 can be configured to move in a direction substantially parallel to the skin surface 50, which can also be generally along the longitudinal axis L in some embodiments, and the third axis can be oriented substantially perpendicularly with respect to one or both of the first axis and the second axis.

Figure 11:
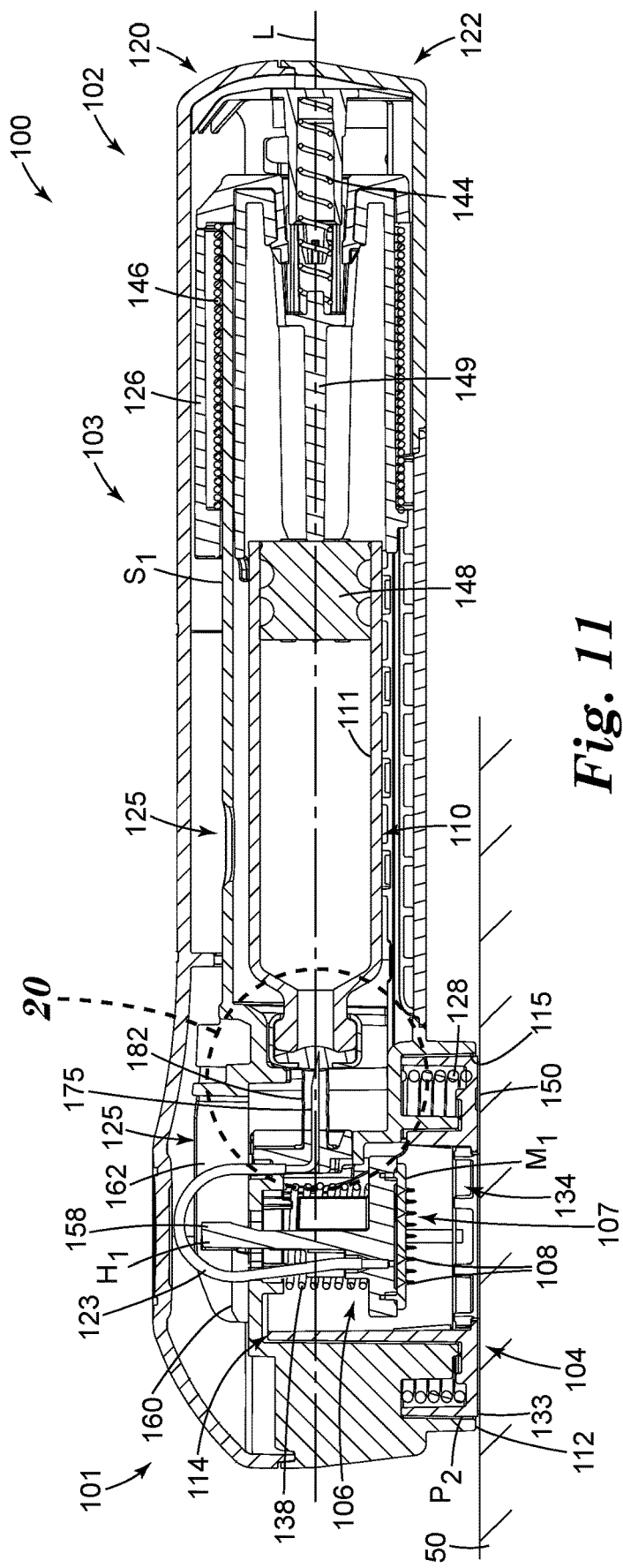
FIG. 11 is a side cross-sectional view of the apparatus of FIGS. 1-10, the apparatus shown in a third condition.
Figure 12:
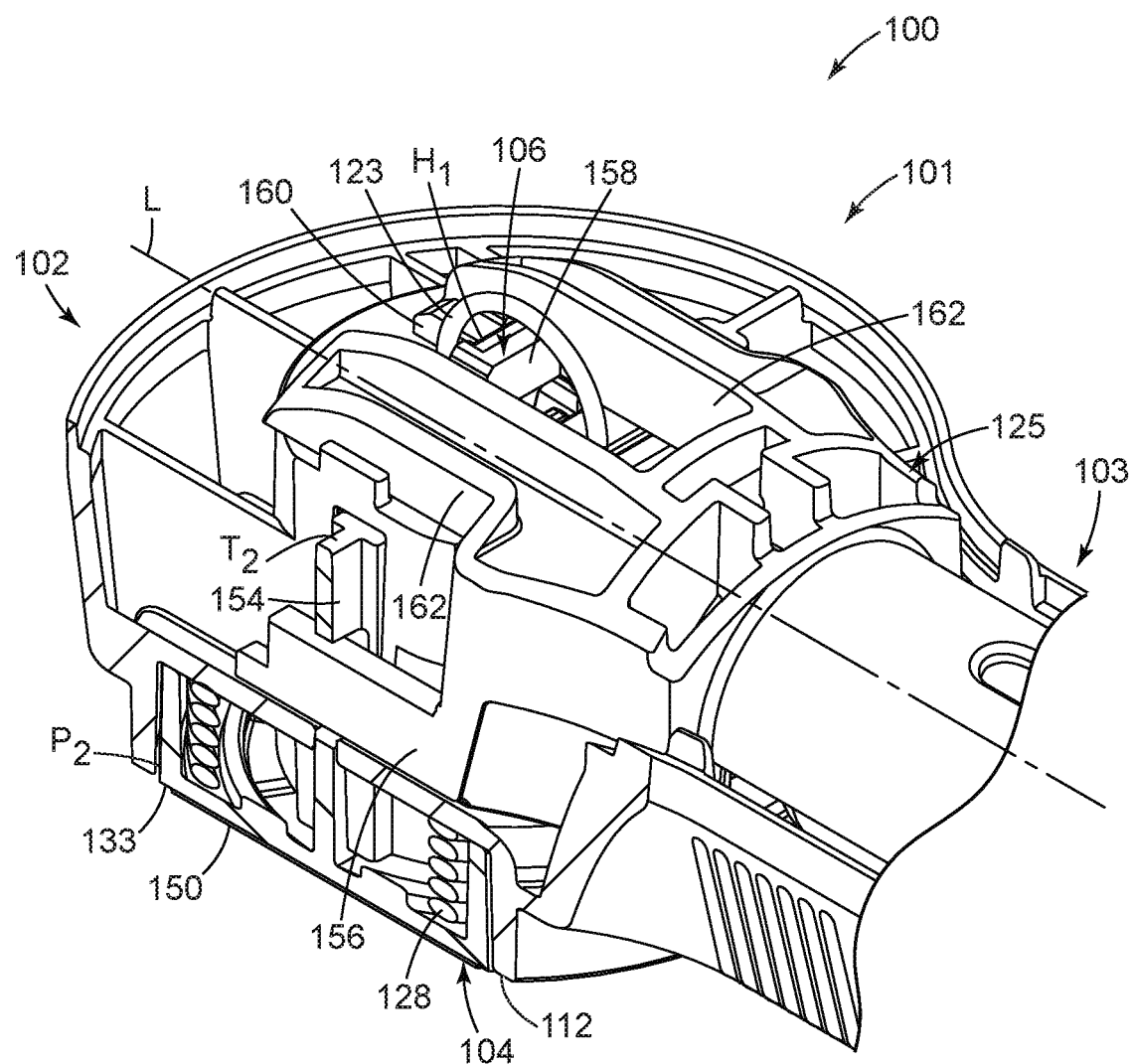
FIG. 12 is a close-up, rear, top, partial perspective view of the apparatus of FIGS. 1-11, the apparatus shown in the third condition.

The shuttle 125 can be configured to interact with the microneedle array holder 106 to retain the holder 106 in its retracted position $H_1$ until the shuttle 125 reaches an intermediate position (i.e., a third position $S_3$—see, e.g., FIG. 13) in between the first position $S_1$ and the second position $S_2$ in which the microneedle array holder 106 is released from being held in its retracted position $H_1$ by the shuttle 125. FIGS. 11 and 12 show the shuttle 125 after it has begun to move from its first position $S_1$, but before it has reached the third position $S_3$ in which the holder 106 is released.

Movement of the shuttle 125 between its first and second positions $S_1$ and $S_2$ can be accomplished or driven by one or more stored energy devices. In the illustrated embodiment, two stored energy devices are used to fully move the shuttle 125 from the first position $S_1$ to the second position $S_2$. By way of example, in the illustrated embodiment, a second stored energy device 144 (see FIGS. 3, 6, 7, 9, 11, 13, 16, 17 and 22) can initiate movement of the shuttle 125, e.g., to move the shuttle 125 from the first position $S_1$ to the third position $S_3$, where the microneedle array holder 106 can be released from its retracted position $H_1$. By way of further example, in the illustrated embodiment, a third stored energy device 146 (see FIGS. 3, 6, 7, 9 and 11, 13, 16, 17 and 22) can complete movement of the shuttle 125 to its second position $S_2$ wherein the reservoir 111 of the cartridge 110 is in fluid communication with the fluid path 123, and can further initiate and complete infusion of an active agent from the reservoir 111 of the cartridge 110, into the fluid path 123, and out the hollow microneedles 108.

The cartridge 110 can include a piston 148 that is movable in the reservoir 111 of the cartridge 110 to force the active agent out of the cartridge 110, into the fluid path 123, and out the hollow microneedles 108. The piston 148 can be in a sliding and sealing relationship with respect to interior walls of the cartridge 110. This can provide adequate sealing for a fluid stored in an interior variable volume chamber formed between the piston 148 and an openable end 151 of the cartridge 110. The piston 148 can be moved or pressed in the cartridge 110 by a plunger 149 that can be coupled to, and movable with, the shuttle 125 and the cartridge 110, until the shuttle 125 reaches its second position $S_2$, after which the plunger 149 can be movable with respect to the housing 102, the shuttle 125, the cartridge 110, etc. to drive the piston 148 to dispense the active agent. That is, in some embodiments, the infusion assembly 103 can be configured such that the piston 148 (and the plunger 149) is not movable in the reservoir 111 with respect to the shuttle 125 until the shuttle is in its second position $S_2$. Said another way, in some embodiments, the infusion assembly 103 can be configured such that the piston 148 is inhibited or prevented from movement to its second position until the shuttle 125 is in its second position $S_2$.

The piston 148 and the plunger 149 can be movable together between (i) a first (non-dispensing or non-delivery) position in which the active agent is not being forced out of the reservoir 111 and into the fluid path 123 (i.e., in which the active agent is contained within the reservoir 111); and (ii) a second, dispensed, position in which the active agent is being forced out of the reservoir 111 and into the fluid path 123.

Given the volume variability of the reservoir 111 of the cartridge 110, the cartridge 110 can be configured to accommodate any intended dosage volume. Such a cartridge 110 may be of the type wherein pre-filled drugs are ready-to-be used. The cartridge 110 may be of the kind that satisfies standards, including international standards, such as the International Organization for Standards (ISO). In addition, a glass cylinder can be employed as the cartridge 110, which can be relatively easy to clean and sterilize.

The present disclosure also contemplates the use of valve mechanisms for opening the openable end 151 of the cartridge 110 for allowing transferring of an active agent to the fluid path 123. For example, a valve member retained by the cartridge 110 may be opened from a fluid blocking or closed condition by having it cooperate with structure (not shown), such as a cannula, as the two are brought into operative engagement. Suitable valve mechanisms include, but are not limited to, those disclosed in International Publication No. WO2005/018705 to Cindrich et al.

Referring back to the piston 148, it is adapted to travel along a length of reservoir 111 (e.g., which can be oriented substantially along the longitudinal axis L) until the active agent is completely (or nearly completely) forced or expressed therefrom. Typically, the piston 148 may be made of materials that seal against the body of cartridge 110, but are also inert with respect to the active agent. For example, purified elastomeric materials such as halobutyl rubber and silicone rubber materials may be typically used for such pistons, but other materials such as non-elastomeric materials are also contemplated. In addition, the piston 148 can be made of diverse materials including laminated constructions. While the illustrated embodiment uses one kind of piston, others can be utilized, including those contoured to substantially match the interior shape of the openable end 151.

Other means to reduce void space in the cartridge are contemplated. For example, small spherical objects can be included in the reservoir 111. When the piston 148 moves forward and pushes the active agent out of the cartridge 110, the small spherical objects can also be pushed forward into the neck of the cartridge 110 and around the piercing element 175. The spherical objects are preferably larger than the fluid path 123 in the piercing element 175 so as to avoid plugging the fluid path 123. Instead, the spherical objects can pack around the piercing element 175 and displace active agent in the cartridge neck space. The spherical objects can be made of metal, plastic, glass, ceramic, or other material that is compatible with the active agent in the reservoir 111.

The cartridge 110 has longitudinal axis that can be generally oriented along the longitudinal axis L of the apparatus 100 and/or that can be oriented generally parallel to the skin 50 in use. In other embodiments, the cartridge 110 can be disposed at non-zero angles relative to the skin 50. In embodiments wherein a low profile for the apparatus 100 (or at least the infusion assembly 103 thereof) is desired, the longitudinal axis of the cartridge 110 can be generally parallel to the major plane (e.g., of the first side 116) of the microneedle array 107 (when coupled to the microneedle array holder 106). The cartridge 110 can be a glass drug cartridge (e.g., that is transparent). Such a glass drug cartridge may be of a commercially available type, such as from Schott North America, Elmsford, N.J., USA, and West Pharmaceutical Services, Inc. of Lionsville, Pa., USA. Other kinds of cartridges having similar properties are well within the scope of the disclosure.

When made of glass, the cartridge 110 may also be advantageous in regard to enhancing the versatility of the delivery systems of the present disclosure. One potential advantage is that the cartridge 110 can conform to the sizes and shapes already familiar in the pharmaceutical field that can be, e.g., readily fillable using commercial equipment. In addition, because the cartridge 110 may be packaged separately from the apparatus 100, users may be able to use custom reservoirs and easily install them in the apparatus 100 at the point of use. As shown in FIG. 6, in some embodiments, a door or cover 147 can be employed to allow direct access to the location of the infusion assembly 103 in which the cartridge 110 can be positioned. Moreover, by being able to use known drug cartridges, patients are able to use a wide variety of drugs and dosages dispensed in a manner particularly tailored to them and not be dependent on a manufacturer of the dispensers having fixed cartridges.

A typical glass drug cartridge that may be employed with the apparatuses of the present disclosure may have dimensions that range from 2 cm to about 8 cm in terms of their length, and may have inner diameters that range from 4 mm to 12 mm. More typically, the lengths may range from 4 cm to 6 cm, and the inner diameters from 6 mm to 10 mm. The present disclosure contemplates other dimensions depending on, for example, the volume of the active agent to be delivered. While a transparent glass drug cartridge may be used, other materials may also be used. The materials and construction of the cartridge 110 are generally compatible with the desired active agent to be dispensed and able to withstand the pressures generated during use.

In some embodiments, the volume of the active agent to be delivered or infused can be at least 0.1 mL, in some embodiments, at least 0.2 mL, and in some embodiments, at least 0.5 mL. In some embodiments, the volume can be no greater than 20 mL, in some embodiments, no greater than 10 mL, in some embodiments, no greater than 5 mL, and in some embodiments, no greater than 3 mL. In some embodiments, the volume can range from 0.1 mL to 20 mL, in some embodiments, from 0.1 mL to 10 mL, and in some embodiments, from 0.1 to 5 mL. In some embodiments, the volume can range from 0.5 mL to 3 mL.

By way of example only, in the illustrated embodiment, the same third stored energy device 146 that completes the movement of the shuttle 125 to its second position $S_2$ can also initiate and complete the infusion process, i.e., to initiate and complete movement of the plunger 149 and the piston 148, accordingly, to dispense the active agent.

In some embodiments, the second and third stored energy devices 144 and 146 can each include a spring or biasing element, and each is shown as a coil spring by way of example only in the illustrated embodiment. However, any of the above stored energy devices can be employed for each of the second and third stored energy devices 144 and 146. In embodiments in which a biasing element is employed, the shuttle 125 can be primed or held under load, e.g., against the bias of the biasing elements 144 and 146 when the shuttle is in the first position $S_1$.

That is, the shuttle 125 can be biased in or toward its second position $S_2$. For example, the shuttle 125 can be biased by one or both of the second stored energy device 144 and the third stored energy device 146, e.g., if one or both of the second and third stored energy devices 144 and 146 includes a biasing element. The shuttle 125 can be maintained in its first position $S_1$ until the actuator 104 has been moved to its second position $P_2$. By way of example, in the illustrated embodiment, the actuator 104 includes a portion that maintains the shuttle 125 in its first position $S_1$ until the actuator 104 has been moved to its second position $P_2$.

Figure 8:
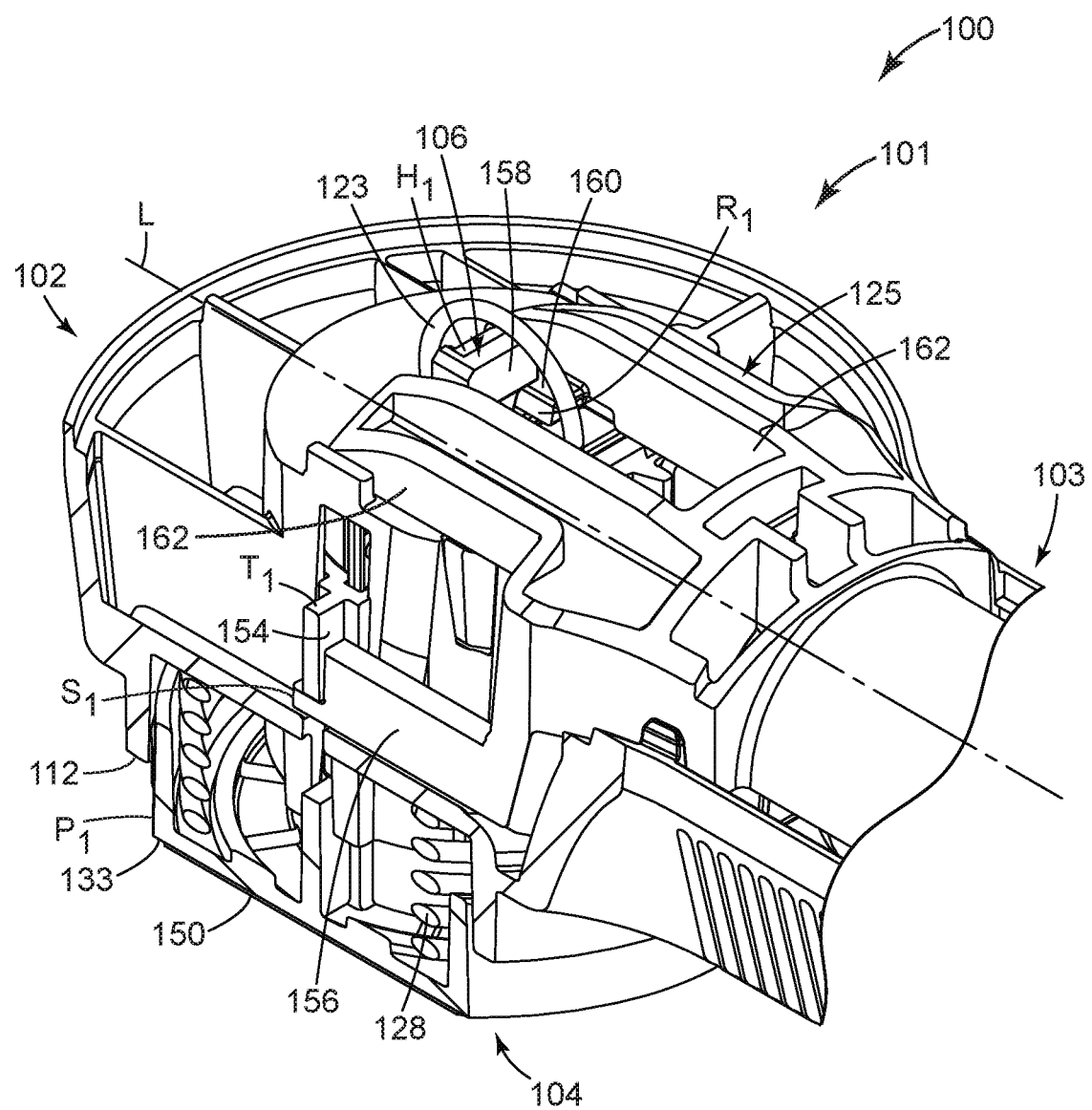
FIG. 8 is a close-up, rear, top, partial perspective view of the apparatus of FIGS. 1-7, the apparatus shown in the first condition with the cover removed.
Figure 10:
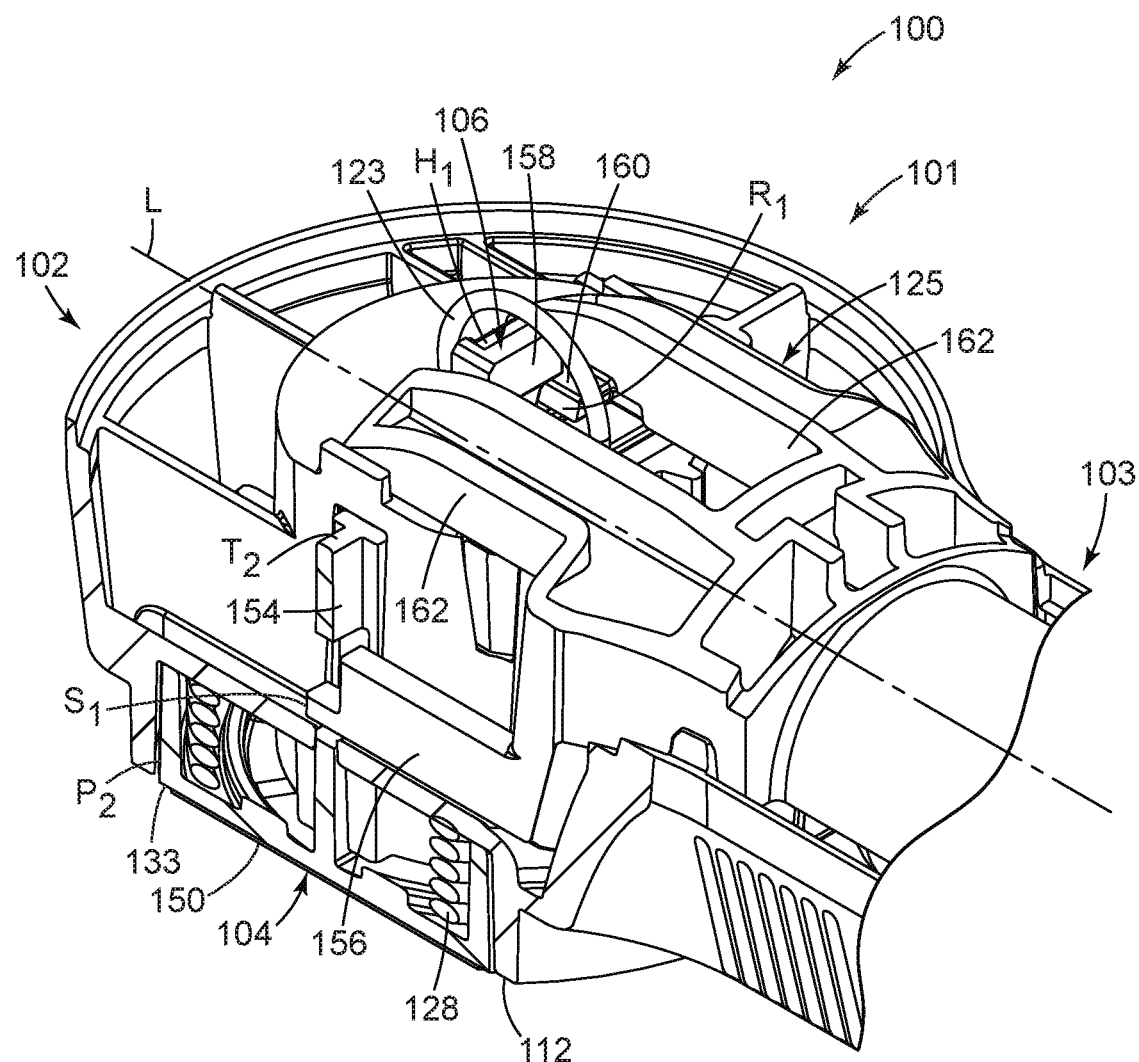
FIG. 10 is a close-up, rear, top, partial perspective view of the apparatus of FIGS. 1-9, the apparatus shown in the second condition.

Specifically, in some embodiments, as shown in FIGS. 8, 10 and 12, the actuator 104 can include one or more shuttle stops (or catches, or detents) 154 that can be movable with the actuator 104 when the actuator is moved between its first and second positions $P_1$ and $P_2$. The apparatus 100 is generally symmetrical about the longitudinal axis L. As such, the illustrated embodiment employs two shuttle stops 154—one on each side of the apparatus 100; however, only one is shown in FIGS. 8, 10 and 12. It should be understood, however, that in some embodiments, the apparatus 100 can include only one shuttle stop 154. In embodiments in which more than one shuttle stop 154 is employed, it should be understood that the description herein can equally apply to additional stops.

The shuttle stop 154 is configured to abut and/or engage at least a portion of the shuttle 125. As a result, the shuttle stop 154 can be coupled to or formed by at least a portion of the actuator 104, and can be movable, with the actuator 104, between:

(i) a first position $T_1$ with respect to the housing 102, the shuttle 125 and the microneedle array holder 106 (see FIG. 8) in which the shuttle stop 154 is positioned to engage at least a portion of the shuttle 125 to hold the shuttle 125 in its first position $S_1$, and (ii) a second position $T_2$ with respect to the housing 102, the shuttle 125 and the microneedle array holder 106 (see FIGS. 10 and 12) in which the shuttle stop 154 is no longer positioned to engage at least a portion of the shuttle 125 to hold the shuttle 125 in its first position $S_1$, such that when the shuttle stop 154 is in the second position $T_2$, the shuttle 125 is free to move to its second position $S_2$, e.g., by the second and third stored energy devices 144 and 146.

In FIGS. 7 and 8, the actuator 104, the shuttle 125, the microneedle array holder 106, and the piston 148 (and the plunger 149) are all in their respective first positions. In these respective first positions, the shuttle 125, the microneedle array holder 106, and the piston 148 (and the plunger 149) can be primed or held under a load, ready to be fired, i.e., driven by the stored energy devices 138, 144 and/or 146.

In FIGS. 9 and 10, the actuator 104 is in its second position $P_2$ and the shuttle stop 154 is in its second position $T_2$, but the shuttle 125 has not yet begun to move toward its second position $S_2$. In FIGS. 11 and 12, the actuator 104 is in its second position $P_2$ and the shuttle stop 154 is in its second position $T_2$, and the shuttle 125 has begun to move toward its second position $S_2$, but the microneedle array holder 106 has not yet been released from its retracted position $H_1$.

As shown in FIGS. 8, 10 and 12, the shuttle 125 can include one or more extensions, prongs or projections 156 that are each configured to engage and interact with a shuttle stop 154. The extensions 156 are shown by way of example as lateral extensions that extend along the lateral sides of the apparatus 100 and are elongated generally along the longitudinal axis L. Each extension 156 includes a first portion (or surface, e.g., a side or front surface in the illustrated embodiment) that can be notched or include a flange configured to engage the shuttle stop 154 of the actuator 104 until the actuator 104 has been moved out of engagement with the shuttle 125, e.g., until the actuator 104 has been moved to the second position $P_2$, thereby moving the shuttle stop 154 to its second position $T_2$.

Each extension 156 can further include a second portion (or surface, e.g., an upper surface in the illustrated embodiment) that can be configured to engage with the shuttle stop 154 after the actuator 104 has been moved to its second position $P_2$ so as to maintain the actuator 104 in the second position $P_2$ after it has been moved to its second position $P_2$. As a result, as the actuator 104 is moved to its second position $P_2$, the shuttle 125 gets released; and the shuttle 125 can be configured such that as the shuttle 125 moves toward its second position $S_2$, the shuttle 125 catches the actuator 104 and holds the actuator 104 in its second position $P_2$.

Such a configuration can inhibit the actuator 104 from being forced back toward its first position $P_1$ after actuation, e.g., which could potentially dislodge the microneedles 108 from the skin 50 during use. Accordingly, each shuttle stop 154 can include a first portion (or surface, e.g., a side or rear surface in the illustrated embodiment) configured to inhibit movement of the shuttle 125 from its first position $S_1$ and a second portion (or surface, e.g., a lower surface in the illustrated embodiment) configured to inhibit movement of the actuator 104 from its second position $P_2$ once the actuator 104 has been moved to its second position $P_2$. However, this arrangement and interaction between the shuttle 125 and the actuator 104 is shown by way of example only. In some embodiments, the shuttle stop 154 on the actuator 104 can be configured to engage a different element when in its second position $P_2$ to maintain the actuator 104 in its second position $P_2$ after it has been moved to its second position $P_2$.

As shown, e.g., in FIGS. 4, 6 and 7-13, in some embodiments, the microneedle array holder 106 can include one or more extensions or prongs 158 configured to engage one or more holder stops 160 on the shuttle 125. Similar to the shuttle stop 154 on the actuator 104, the holder stop 160 is movable with the shuttle 125, between:

(iii) a first position $R_1$ with respect to the housing 102, the actuator 104, and the microneedle array holder 106 (see FIGS. 7-10) in which the holder stop 160 is positioned to engage at least a portion of the microneedle array holder 106 (i.e., the extension 158) to hold the microneedle array holder 106 in its retracted position $H_1$, and (iv) a second position $R_2$ with respect to the housing 102, the actuator 104, and the microneedle array holder 106 (see FIG. 13) in which the holder stop 160 is no longer positioned to engage at least a portion of the microneedle array holder 106 to hold the microneedle array holder 106 in its retracted position $H_1$, such that when the holder stop 160 is in the second position $R_2$, the microneedle array holder 106 is free to move toward its extended position $H_2$, e.g., by the first stored energy device 138.

FIGS. 11 and 12 illustrate the shuttle 125 before it has quite reached its intermediate third position $S_3$ in which the microneedle array holder 106 is released and able to move toward its extended position $H_2$, which is shown in FIG. 13. As mentioned above and is described in greater detail below with respect to FIGS. 14 and 15, FIG. 13 illustrates an optional dampened position of the holder 106, before the holder 106 has fully reached its extended position $H_2$, which is shown in FIGS. 15-17 and 22.

The holder stop(s) 160 on the shuttle 125 can be coupled to or formed by a portion of the shuttle 125. By way of example only, the extension 158 on the holder 106 is shown as being a vertical extension or projection. The extension 158 can be notched or include a flange (e.g., such that the extension 158 includes a lower surface) that is configured to abut the holder stop 160 (e.g., an upper surface thereof). The holder stop 160 can extend a predetermined distance along the longitudinal axis L of the apparatus 100, such that when the holder stop 160 has moved to its second position $R_2$, the extension 158 on the holder 106 has cleared the holder stop 160, is no longer in engagement with the holder stop 160, and the holder 106 is free to be driven by the first stored energy device 138 to its extended position $H_2$. By further way of example, the holder stop 160 can be formed or defined by one or more extensions, prongs or projections 162. Specifically, in the illustrated embodiment, the shuttle 125 includes two extensions 162 that extend generally along the longitudinal axis L of the apparatus 100 and include a lower ledge or flange that includes an upper surface that defines the holder stop 160. In the illustrated embodiment, the holder stop 160 is specifically formed by two of such ledges that the extension 158 of the holder 106 rests on, or is forced against, when the holder 106 is held under load in its retracted position $H_1$. That is, the extension 158 and the holder stop 160 slide relative to one another as the shuttle 125 is moved in the housing 102 generally along the longitudinal axis L of the apparatus 100 toward its second position $S_2$, until the holder stop 160 reaches its second position $R_2$ (i.e., until the shuttle 125 reaches its third position $S_3$, located intermediately between its first position $S_1$ and its second position $S_2$).

As shown in FIGS. 6 and 14-15, in some embodiments, the apparatus 100 can include one or more dampeners 163 positioned between the microneedle array holder 106 and the actuator 104 (or the housing 102 in embodiments in which the holder 106 is not moving to its extended position $H_2$ adjacent the inverted actuator 104). The dampeners 163 can be configured to at least partially deform in response to the inertia of the microneedle array holder 106 as the holder 106 is driven by the first stored energy device 138 to its extended position $H_2$, thereby dampening or slowing the holder 106 as it comes to a stop in its extended position $H_2$. In the illustrated embodiment, the dampener 163 includes a wire formed into an incomplete circle (see FIG. 6) positioned in a recess within the cavity 134 of the actuator 104 and located between the base 133 of the actuator 104 and an underside of the holder 106 (see FIG. 14). FIG. 15 illustrates the holder 106 at the end of its travel (i.e., with the holder 106 fully in its extended position $H_2$ and the microneedle array 107 fully in its extended position $M_2$), with its guide rails resting on the ends of guides formed within the actuator 104. The dampener 163 in FIG. 15 has been deformed and forced into a lower recess 164 by the holder 106. In the illustrated embodiment, the recess 164 into which the dampener 163 is forced is defined by the actuator 104; however, in embodiments in which the holder 106 does not travel in the actuator 104, such a recess could be provided by the housing 102 or another element of the apparatus 100. The illustrated dampener 163 and relative configuration between the holder 106 and the actuator 104 are shown by way of example only; however, any energy or shock absorbing element or material can be employed and other configurations are possible and within the spirit and scope of the present disclosure.

Figure 16:
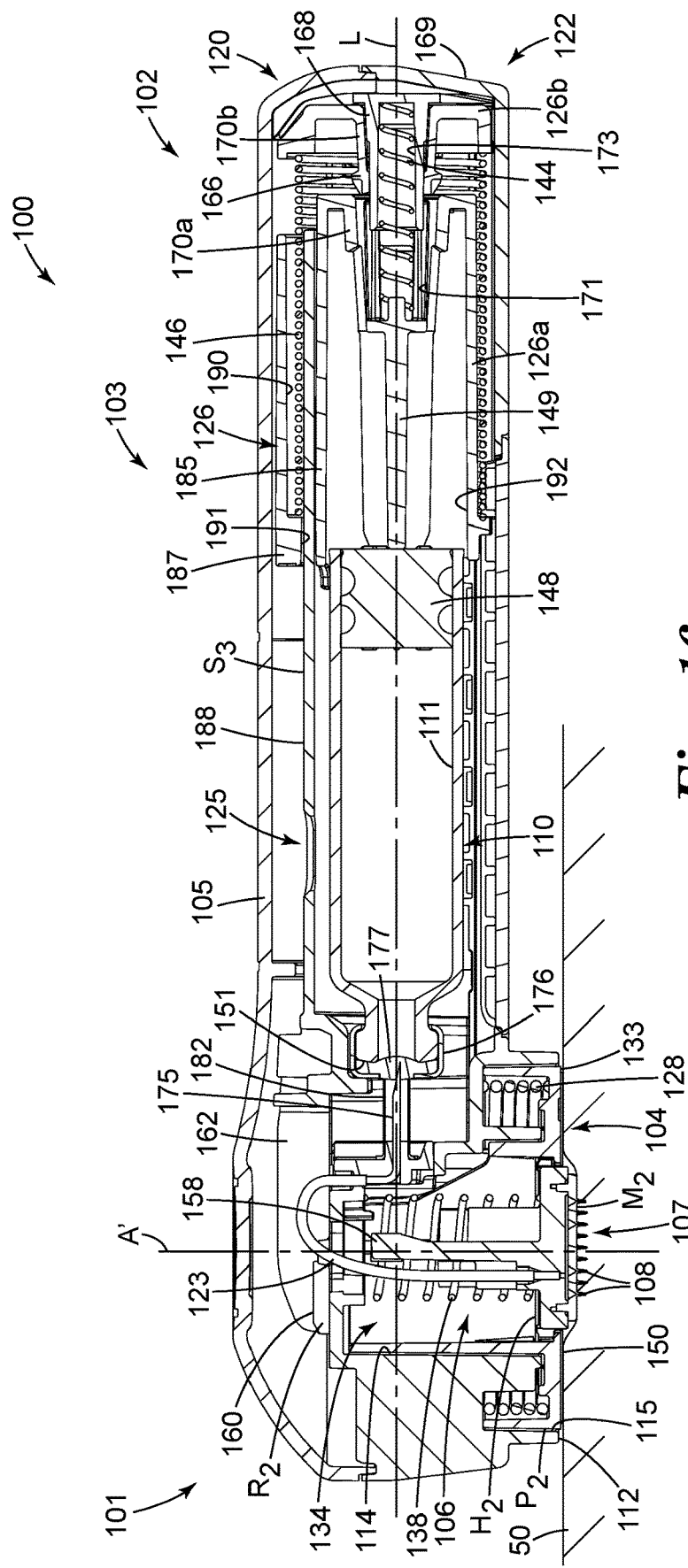
FIG. 16 is a side cross-sectional view of the apparatus of FIGS. 1-15, the apparatus shown in the fifth condition.
Figure 17:
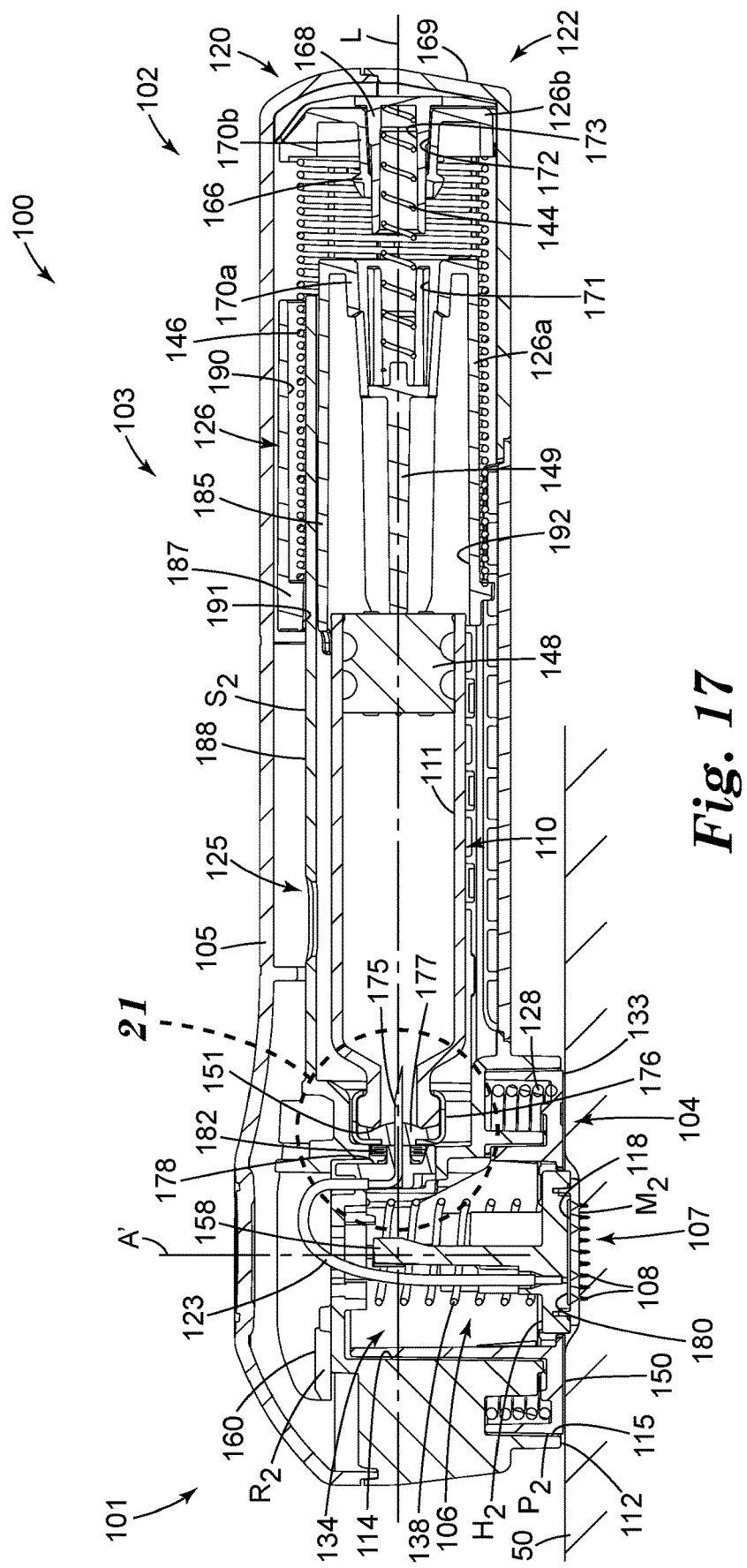
FIG. 17 is a side cross-sectional view of the apparatus of FIGS. 1-16, the apparatus shown in a sixth condition.
Figure 22:
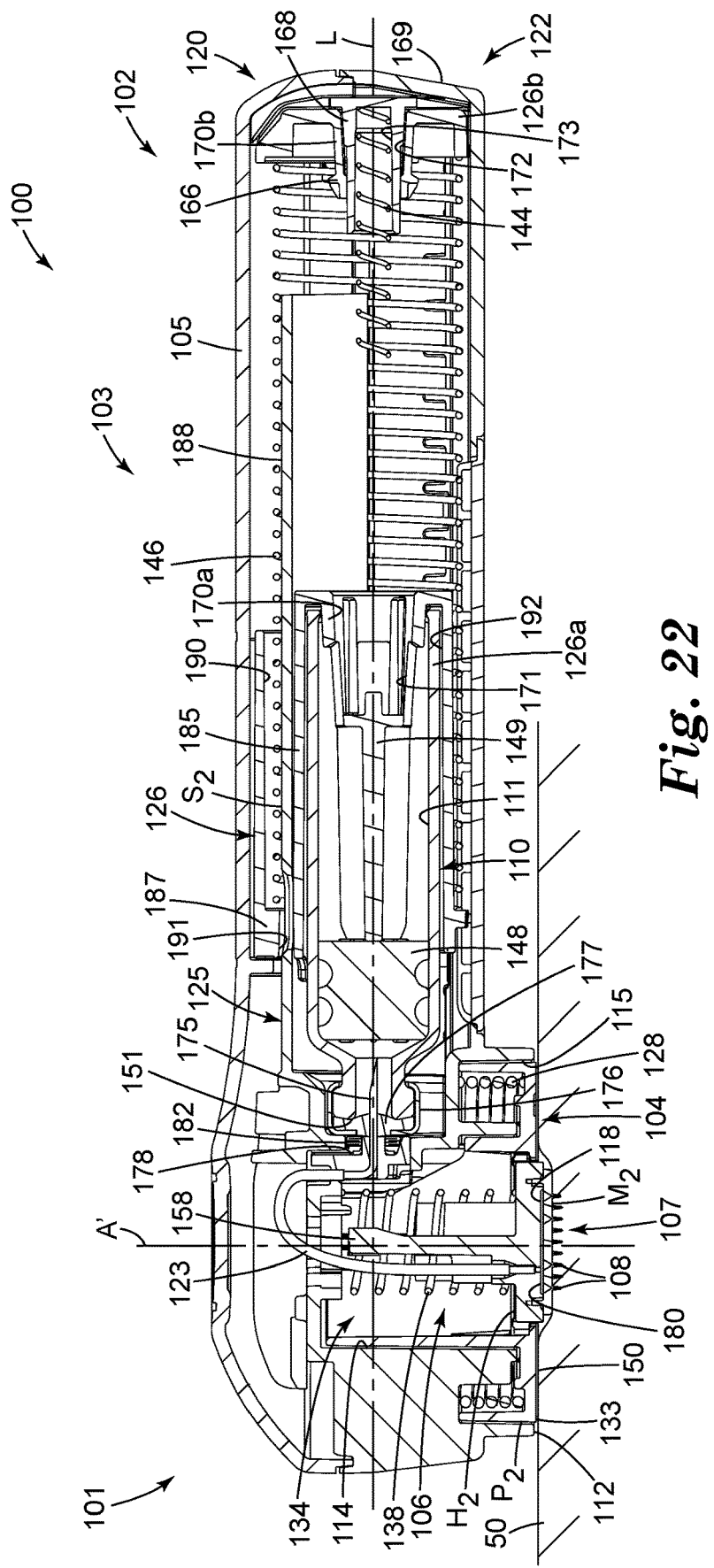
FIG. 22 is a side cross-sectional view of the apparatus of FIGS. 1-21, the apparatus shown in a seventh condition.

While the microneedle array 107 impacts the skin 50, the shuttle 125 continues to travel along the longitudinal axis L toward its second position $S_2$ (as shown in FIGS. 17 and 22). In the illustrated embodiment, as shown in FIGS. 13, 16, 17 and 22, the indicator 126 can include a first portion (or "main body") 126a and a second portion (or "tail") 126b that are configured to be removably coupled together, e.g., by one or more latches or detents 166.

The second stored energy device 144 (e.g., a spring) can be located within one or more retaining walls or tubes 168 (see, e.g., FIG. 13), which are provided by, or fixedly coupled to, the housing 102. By way of example, the retaining wall 168 is generally tubular, generally centrally located in the housing 102 with respect to the shuttle 125 and the indicator 126, and oriented generally along the longitudinal axis L. The retaining wall 168 can define a recess (or bore or chamber) 173, e.g., which can receive at least a portion of the second stored energy device 144. In addition, the first indicator portion 126a and the second indicator portion 126b of the illustrated embodiment each include inner (e.g., concentric and forwardly-projecting) walls (or prongs or projections) 170a and 170b, respectively, that are removably coupled together (e.g., at their respective front ends) via the latch 166 and together define a generally tubular recess 172 (see FIG. 13) configured to receive the retaining wall 168. By way of example, in the illustrated embodiment, the inner wall 170b of the second indicator portion 126b is formed by a series of (circumferentially-spaced) prongs configured to be arranged about the inner circumference defined by the inner wall 170a of the first indicator portion 126a when the first and second indicator portions 126a and 126b are coupled together via the latch 166. Accordingly, the inner wall 170a of the first indicator portion 126a can include a series of notches or openings configured to receive at least a portion of the inner wall 170b, i.e., the portion(s) of the one or more prongs forming the one or more latches 166.

As the shuttle 125, along with the indicator 126, is initially moved from its first position $S_1$ by the second stored energy device 144, the inner walls 170a and 170b, removably coupled by the latch 166, slide or ride along the retaining wall 168 (and the retaining wall 168 is received within the recess 172 defined by the inner walls 170a and 170b). At this stage, the retaining wall 168 inhibits the inner walls 170a and 170b from flexing or deflecting inwardly, thereby maintaining the latch 166 in a closed or latched configuration and maintaining the inner walls 170a and 170b coupled together.

The retaining wall 168 only extends (e.g., along the longitudinal axis L of the apparatus 100) a relatively short distance forward from a rear wall 169 of the housing 102. Thus, as the shuttle 125 and the indicator 126 continue to travel in the housing 102, the inner walls 170a and 170b of the first indicator portion 126a and the second indicator portion 126b move beyond the retaining wall 168 to a location where the inner walls 170a and 170b can flex relative to one another. Particularly, in the illustrated embodiment, at this point, the inner wall 170b of the second indicator portion 126b is free to flex inwardly, i.e., relative to the inner wall 170a of the first indicator portion 126a. The third stored energy device 146 can now provide (or assist in providing) the energy necessary to overcome the latch or detent 166 to allow the first and second indicator portions 126a and 126b to become separated, as shown in FIG. 16. The third stored energy device 146 is positioned to engage at least a portion of the second indicator portion 126b to cause the second indicator portion 126b to move in a direction opposite the shuttle 125 and the first indicator portion 126a, e.g., rearwardly in the housing 102 toward the rear wall 169, with the inner wall 170b riding along and receiving the retaining wall 168.

In some embodiments, at least a portion of the indicator 126 can be in an abutting relationship with the shuttle 125. For example, as shown in FIG. 13, prior to the shuttle 125 reaching its second position $S_2$, the second indicator portion 126b can be in abutting relationship with a rear end of the first indicator portion 126a and a rear end of the shuttle 125, i.e., until the first indicator portion 126a and the second indicator portion 126b are separated.

After the first indicator portion 126a and the second indicator portion 126b are separated, the second stored energy device 144 and the third stored energy device 146 are both positioned to continue to move the shuttle 125 and the first indicator portion 126a in the housing 102 toward the second shuttle position $S_2$. The second stored energy device 144 is positioned to continue pushing the plunger 149, while the third stored energy device 146 is positioned to move the first indicator portion 126a, which is coupled to the plunger 149 (e.g., via the inner wall 170a). The plunger 149 is positioned to contact and push the piston 148 to pressurize the reservoir 111 of the cartridge 110, and a front end (i.e., the openable end 151) of the cartridge 110 is positioned to contact an inner surface of the shuttle 125 to continue to drive the shuttle 125 to its second position $S_2$ (as shown in FIGS. 17 and 22). In some embodiments, the fluid within the cartridge 110 is not pressurized until this step, i.e., until the apparatus 100 is actuated and the resulting series of events includes pressurizing the cartridge 110. For example, in the illustrated embodiment, the second stored energy device 144 is responsible for launching the shuttle 125 (and the cartridge 110) toward its second position $S_2$, and the third stored energy device 146, which is configured to provide greater forces than the second stored energy device 144, completes the movement of the shuttle 125, pressurizes and energizes the cartridge 110, and moves the piston 148 in the reservoir 111 of the cartridge 110.

The second indicator portion 126b that is configured to be removably coupled to the first indicator portion 126a is described as being a portion of the indicator 126 by way of example only. This element can instead be described as a portion of the shuttle 125, or as a separate element altogether that is configured to be removably coupled to at least one of the indicator 126 and the shuttle 125.

By way of example only, the plunger 149 of the illustrated embodiment is coupled to or provided by (e.g., integrally formed with) the indicator 126, such that the indicator 126 includes (i) an inner portion 185 (i.e., positioned to comprise or be coupled to the plunger 149), at least a portion of which is responsible for engaging and moving the piston 148 in the cartridge 110; and (ii) an outer portion 187 configured to ride along an outer surface or wall 188 of the shuttle 125 to be visible through the window 124 to display the progress of the infusion of the active agent (see FIGS. 13, 16, 17 and 22). Specifically, in the illustrated embodiment, the outer portion 187 of the indicator 126 is dimensioned to be received between a retaining wall 105 of the housing 102 and the outer surface or wall 188 of the shuttle 125. That is, the outer portion 187 of the indicator 126 can be dimensioned to receive at least a portion of the shuttle 125, such that after the shuttle 125 has been moved to its second position $S_2$, the indicator 126 can be movable with respect to the shuttle 125.

Furthermore, in the illustrated embodiment, the plunger 149 includes or defines an internal recess or chamber 171, and the second stored energy device 144, e.g., in the case where a spring is employed as the second stored energy device 144, can be dimensioned to be at least partially received in the recess 173 defined by the retaining wall 168 and extend at least partially into the internal chamber 171 to drive or bias the plunger 149 away from the rear wall 169 of the housing 102.

Additionally, in the illustrated embodiment, the outer portion 187 of the indicator 126 includes a first outer recess or chamber 190 defined between an inner surface or wall of the outer portion 187 of the indicator 126 and the outer surface or wall 188 of the shuttle 125, the first outer recess 190 opening rearwardly. The first outer recess 190 can be dimensioned to receive the third stored energy device 146 (e.g., when a spring is employed as the third stored energy device 146). As such, the third stored energy device 146 can be positioned to drive or bias a forward or front end of the indicator 126 forward in the housing 102, away from the rear wall 169 of the housing 102. In some embodiments, as shown, the outer portion 187 of the indicator 126 can further include a second outer recess 191 dimensioned to receive at least a portion of the shuttle 125, the second outer recess 191 opening forwardly.

Furthermore, in some embodiments, as shown, the inner portion 185 of the indicator 126 can also include or define an inner recess or chamber 192 dimensioned to receive at least a portion of the cartridge 110. Particularly, the inner recess 192 can receive a closed end of the cartridge 110 (e.g., that includes the piston 148), for example, in a press-fit engagement. As shown, the cartridge 110 can be positioned in the inner recess 192 such that the piston 148 abuts a forward or front end of the plunger 149.

As shown in FIG. 17, the combined forces provided by the second stored energy device 144 and the third stored energy device 146 can complete the movement of the shuttle 125 to its second infusing position $S_2$ where the reservoir 111 of the cartridge 110 is placed into fluid communication with the fluid path 123. By way of example, as described above, the fluid path 123 can include or be coupled to the piercing element 175 (e.g., a hollow needle) that, by way of example only, can remain fixed with respect to the housing 102 and the shuttle 125. By way of further example, the cartridge 110 can be fitted with a cap 176 and a septum 177 that is accessible via the cap 176. In some embodiments, the cartridge 110 can include a glass cylinder, and the open, or openable, end 151 can be closed and sealed by the cap 176. The cap 176 can include a metallic cap, such as an aluminum cap, that can be crimped to the open end 151 of the cartridge 110 in a know manner. The cap 176 can hold the septum 177 that sealingly closes the otherwise open end 151 of the cartridge 110.

The septum 177 may be made of many different materials including those typically used with reservoirs (e.g., drug cartridges). The septum 177 may be made of a pierceable and resealable elastomeric seal or septum that is securely mounted, with or without being crimped, across the open end 151 of the cartridge 110. In some embodiments, the septum 177 (e.g., formed of an elastomer) may be crimped onto an end of the cartridge 110 with a malleable cap 176, e.g., formed of aluminum. Other similar septum materials and modes of securing it to the open end 151 of the cartridge 110 may be used. For example, a septum molded into the body of a cylinder may be used, such as the CZ series available from West Pharmaceutical Services, Inc, Lionville, Pa., a cap, such as a standard syringe luer cap, or a molded end thin enough to be pierced. Suitable materials are subject to piercing with sufficient piercing force and maintain a seal once pierced. As noted above, the septum 177 can be pierced during use and seal around the piercing element 175 with enough force to prevent leakage during pressurization and transfer of the active agent from the reservoir 111. Certain septum materials allow the septum 177 to reseal following withdrawal of the piercing element 175 after use. The present disclosure envisions unsealing or opening the otherwise closed septum 177 by a variety of approaches.

When the shuttle 125 is moved to its second position $S_2$, the piercing element 175 can pierce or puncture the septum 177, thereby placing the fluid path 123 (i.e., via the interior of the piercing element 175) in fluid communication with the reservoir 111 of the cartridge 110, as shown in FIG. 17. At this point, as further shown in FIG. 17, the open end 151 of the cartridge 110 (e.g., and the cap 176) abuts a base 178 of the piercing element 175, which defines the second position $S_2$ of the shuttle 125. As a result, the shuttle 125 and the cartridge 110 come to a stop within the housing 102. The third stored energy device 146, an end of which is positioned to engage an end of the indicator 126 can now transfer its remaining stored energy to moving the indicator 126 (i.e., the first indicator portion 126a), along with the plunger 149, to drive the piston 148 within the reservoir 111 and force the active agent into the fluid path 123, via the piercing element 175, to the hollow microneedles 108. FIG. 18 shows the indicator 126 beginning to be displayed through the window 124 of the housing 102 as the infusion process begins. The indicator 126 can be colored or otherwise conspicuous relative to the other components of the apparatus 100 to be clearly visible to a user.

In the illustrated embodiment, the first side 121 of the holder 106 and the second side 118 of the microneedle array 107 can be configured to be spaced a distance apart when the microneedle array 107 is coupled to the holder 106 to define a reservoir or manifold 180 therebetween (see FIGS. 14, 15, 17 and 22). Particularly, when the microneedle array 107 is coupled to the holder 106, the second side 118 of the microneedle array 107, or a portion thereof, can be spaced a distance from the first side (or base) 121 of the holder 106 to define the reservoir 180. As shown in FIGS. 14 and 15, the reservoir 180 can be configured to be closed on all sides to inhibit leakage. Additional sealing members can be employed as necessary. The fluid path 123 can include or be in fluid communication with the reservoir 180, and the reservoir 180 can be in fluid communication with the hollow microneedles 108 (i.e., via the second side 118 of the microneedle array 107). That is, in some embodiments, the substrate 109 can include one or more channels positioned to extend thereacross to provide fluid communication between the first side 116 and the second side 118 of the microneedle array 107. As a result, as the active agent is driven out of the reservoir 111 of the cartridge 110 and into the fluid path 123, the active agent is moved to the reservoir 180 that is positioned to deliver or feed the active agent to the plurality of hollow microneedles 108, to in turn deliver the active agent to the skin 50 via the microneedles 108. Other configurations of providing fluid communication between the piercing element 175 (e.g., the rest of the fluid path 123) and the microneedles 108 are possible, and the reservoir 180 is shown by way of example only.

Figure 19:
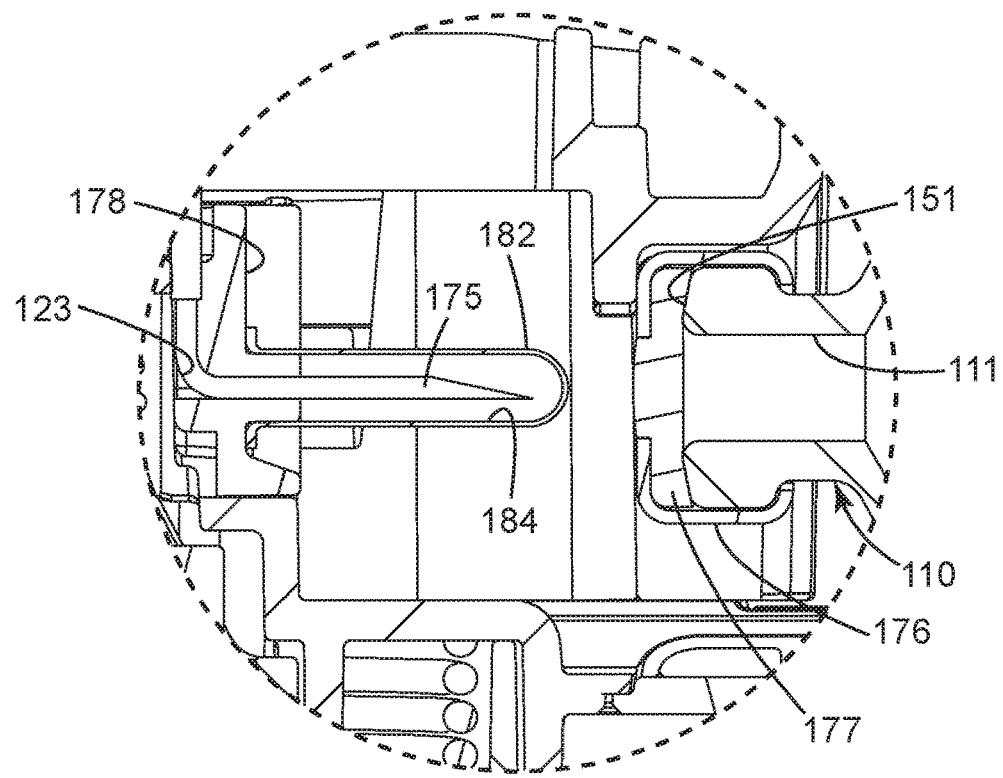
FIG. 19 is a close-up side cross-sectional view of the apparatus shown in FIG. 9, taken of the portion enclosed in the circle labeled "19" in FIG. 9.
Figure 20:
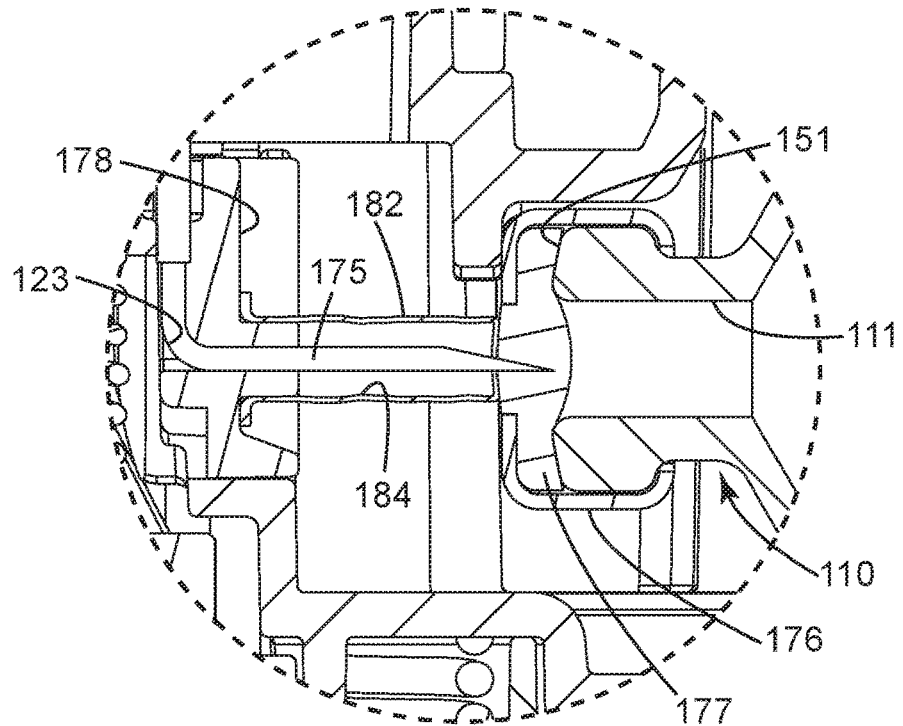
FIG. 20 is a close-up side cross-sectional view of the apparatus shown in FIG. 11, taken of the portion enclosed in the circle labeled "20" in FIG. 11.
Figure 21:
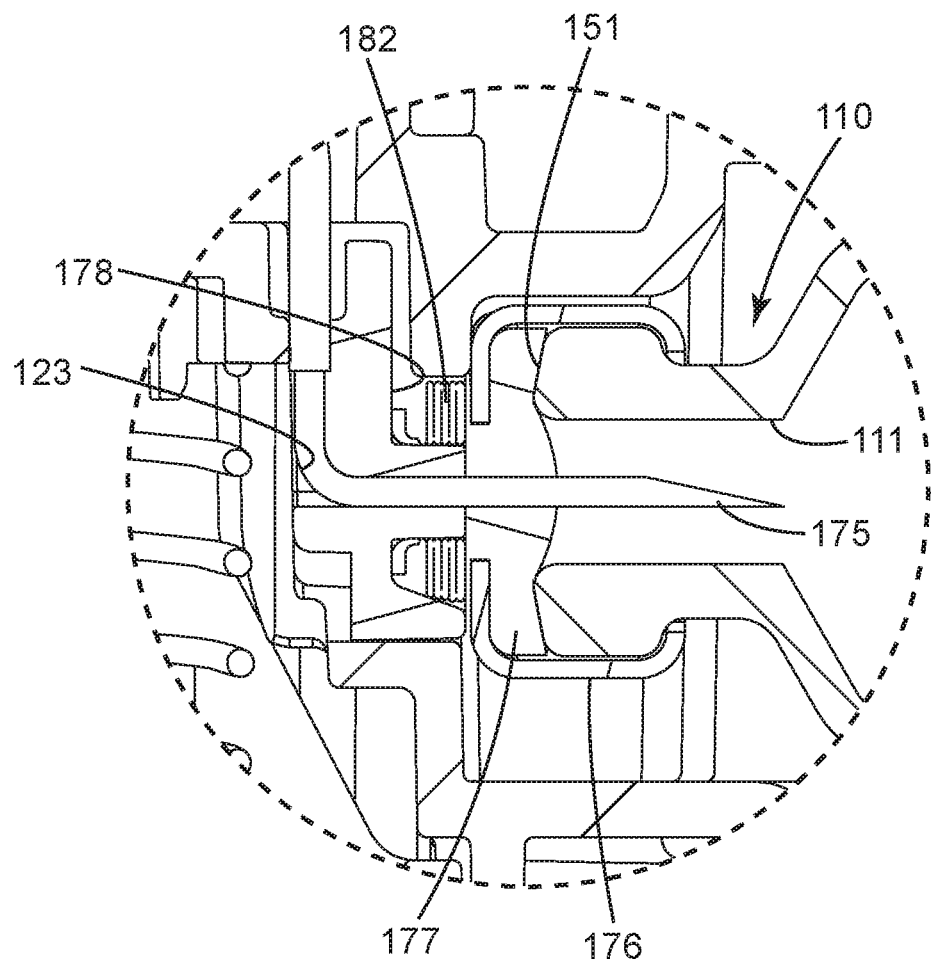
FIG. 21 is a close-up side cross-sectional view of the apparatus shown in FIG. 17, taken of the portion enclosed in the circle labeled "21" in FIG. 17.

FIGS. 7, 9, 11, 13, 16, 17, and 19-21 illustrate a sterility seal 182 positioned to enclose and maintain the sterility of the piercing element 175 prior to piercing the septum 177 and positioning the piercing element 175 in fluid communication with the reservoir 111 of the cartridge 110. Particularly, FIGS. 19-21 show close-up side cross-sectional views of the piercing element 175 and the sterility seal 182, and particularly, show close-up views of the piercing element 175 and the sterility seal 182 of FIGS. 9, 11 and 17, respectively, before the seal 182 is punctured, as the seal 182 is punctured, and after the seal 182 is punctured and collapsed.

As the shuttle 125 moves the cartridge 110 to the second position $S_2$, the septum 177 that is positioned over the open end 151 of the cartridge 110 contacts and deforms the seal 182 until the piercing element 175 pierces or punctures the seal 182 (see FIG. 20). As the shuttle 125 (and the cartridge 110) continues moving, the piercing element 175 continues moving through the seal 182 as it punctures the septum 177. That is, the seal 182 can be configured to deform and collapse toward the base 178 of the piercing element 175, and can be further configured to remain in a collapsed configuration after being pierced (e.g., incapable of returning to its original position or configuration), as shown in FIG. 21.

In some embodiments, the seal 182 can be formed of materials similar those described above with respect to the septum 177 that allow the seal 182 to be pierced during use and seal around the piercing element 175 with enough force to prevent leakage during pressurization and transfer of the active agent from the reservoir 111, or at least until the piercing element 175 pierces the septum 177 and the septum 177 can prevent leakage. In some embodiments, the seal 182 merely collapses around the piercing element 175 and does not seal around the piercing element 175.

As further shown in FIGS. 19-21, the sterility seal 182 can be configured to change from a first state (see FIG. 19) in which the sterility seal 182 defines a chamber (e.g., a sterile chamber) 184 configured to house the piercing element 175 to a second state (see FIG. 21) in which the sterility seal 182 has been pierced by the piercing element 175 and is collapsed, particularly, between the septum 177 (or the cap 176 or the open end 151 of the cartridge 110) and the base 178 of the piercing element 175. FIG. 20 illustrates a third state or condition that is intermediate of that shown in FIGS. 19 and 21, in which the seal 182 is punctured by the piercing element 175.

As mentioned above, the piston 148 and the plunger 149 can be movable together between a first, non-dispensing, position (e.g., as shown in FIG. 17) and a second, dispensed, position (e.g., as shown in FIG. 22), respectively. FIGS. 22 and 23 illustrate the apparatus 100 with the piston 148 and the plunger 149 in their respective second positions. That is, after fluid communication is established (see FIG. 17) between the fluid path 123 and the reservoir 111 of the cartridge 110, the shuttle 125 is maintained in its second position $S_2$, and the third stored energy device 146 continues to drive the indicator 126 in the housing 102, e.g., along the longitudinal axis L, which also drives the plunger 149, which in turns moves the piston 148 within the cartridge 110 to force the active agent into the fluid path 123. FIG. 23 illustrates what a user would see when infusion or delivery of the active agent is complete and the apparatus 100 can be removed from the skin 50.

In use, the cover 113 and release liner 152 can be removed. The skin-contact adhesive 150 on the base 133 of the actuator 104 (and/or on the base 112 of the housing 102) can be applied to the skin 50. An upper portion (e.g., the first portion 120) of the housing 102 of the apparatus 100 can be pressed toward the skin 50 to cause the actuator 104 to move from its first position $P_1$ (as shown in FIGS. 7 and 8, which illustrate a first condition of the apparatus 100) to its second position $P_2$ (as shown in FIGS. 9 and 10, which illustrate a second condition of the apparatus 100), e.g., against the bias of the biasing element 128.

Movement of the actuator 104 to its second position $P_2$ releases the shuttle 125 (i.e., by moving the shuttle stop 154) to allow the shuttle 125 to begin moving toward its second position $S_2$ (as shown in FIGS. 11 and 12, which illustrate a third condition of the apparatus 100), e.g., as a result of being driven by the second stored energy device 144 (as shown in FIG. 11). After the shuttle 125 is moved to a third position $S_3$ located between its first and second positions $S_1$ and $S_2$, the holder stop 160 on the shuttle 125 is no longer positioned to retain the microneedle array holder 106 in its retracted position $H_1$, such that the holder 106 is released, and the first stored energy device 138 can begin to provide forces to drive the microneedle array holder 106 toward its extended position $H_2$ (as shown in FIGS. 13-14, which illustrate a fourth condition of the apparatus 100). In the illustrated embodiment, FIGS. 13 and 14 show a dampened position of the holder 106, and the holder 106 can continue to its full extended position $H_2$ (and accordingly, the microneedle array 107 can continue to its extended position $M_2$), as shown in FIGS. 15 and 16, which illustrate a fifth condition of the apparatus 100. However, some embodiments do not employ the dampener 163 or the dampened position of the holder 106 illustrated in FIGS. 13 and 14. The shuttle 125 then continues to move toward its second position $S_2$ and the first indicator portion 126a and the second indicator portion 126b are allowed to separate (as shown in FIG. 16), at which point the third stored energy device 146 can provide, or assist in providing, forces to continue to move the shuttle 125 to the second position $S_2$.

When the shuttle 125 reaches its second position $S_2$ (as shown in FIG. 17, which illustrates a sixth condition of the apparatus 100), the reservoir 111 of the cartridge 110 of the infusion assembly 103 is placed into fluid communication with the fluid path 123, and particularly with the microneedles 108 in the injection assembly 101. Also, at this point, the indicator 126 (e.g., the first indicator portion 126a) can begin to move relative to the shuttle 125, which can drive the piston 148 in the reservoir 111 (e.g., with the plunger 149), and the progress of the piston 148 can be displayed to a user by the indicator 126, which can be visible through the window 124 in the housing 102 (as shown in FIG. 18). When the piston 148 and the plunger 149 (and the indicator 126) reach their respective second positions (as shown in FIGS. 22 and 23, which illustrate a seventh condition of the apparatus 100), infusion of the active agent is complete. This can be indicated to a user with the indicator 126, which can be visible through the window 124 of the housing 102, e.g., by showing the indicator 126 as filling up the window 124.

Figure 24:
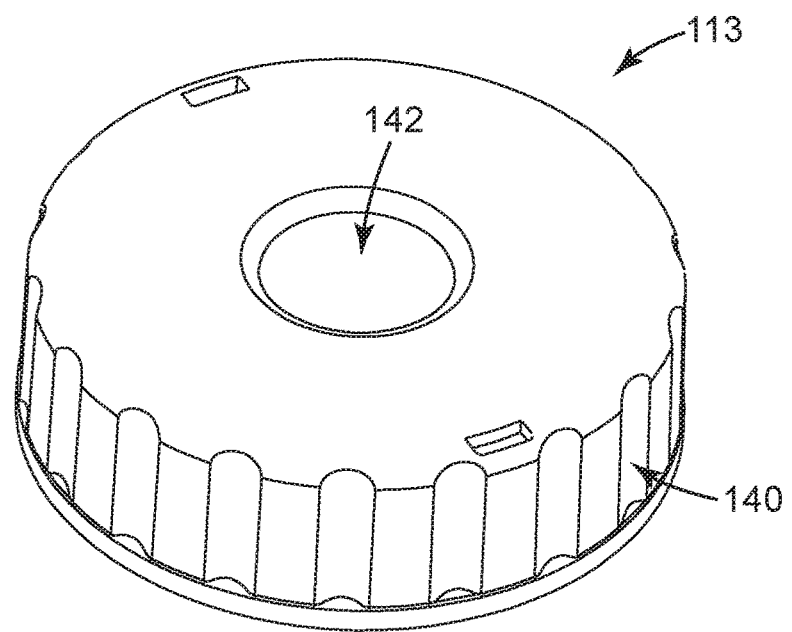
FIG. 24 is a top perspective view of the cover of FIGS. 1-6.
Figure 25:
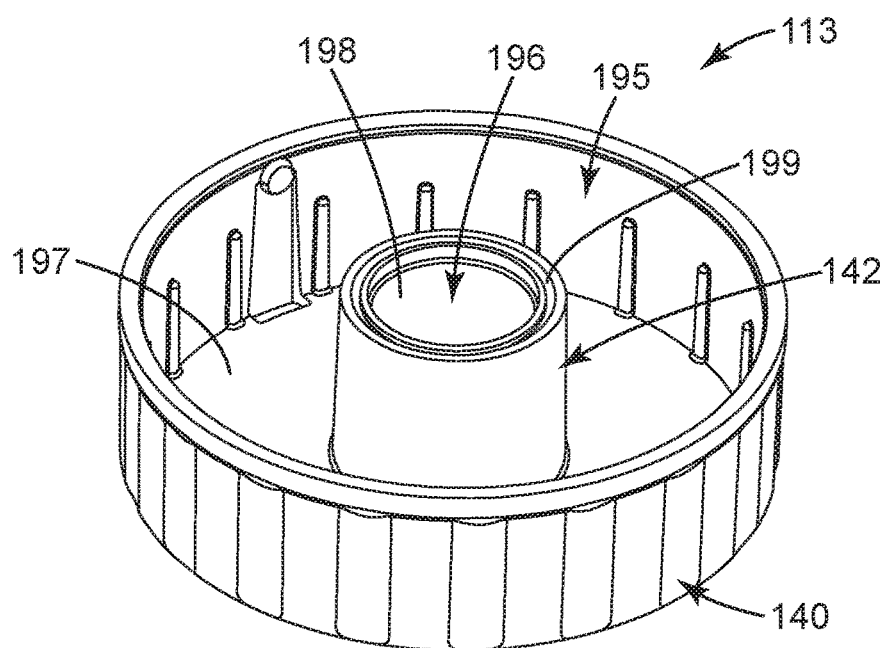
FIG. 25 is a bottom perspective view of the cover of FIGS. 1-6 and 24.

FIGS. 24 and 25 illustrate the cover 113 in greater detail. As mentioned above, the cover 113 can include (i) a first (e.g., outer) portion 140 configured to cover at least a portion of the base 112 of the housing 102 adjacent the opening 115, as well as the base 133 of the actuator 104; and (ii) a second (e.g., inner) portion 142 configured to be received in the cavity 114 of the housing 112 and further configured to cover the plurality of microneedles 108 on the microneedle array 107 when the microneedle array holder 106 is in the retracted position $H_1$. The second portion 142 can also be configured to be received in the cavity 134 of the actuator 104, e.g., in embodiments employing an inverted actuator 104 through which the microneedle array 107 is deployed. In addition, the first portion 140 can cover the base 133 of the actuator 104 adjacent the opening 135 in embodiments employing an inverted actuator 104 through which the microneedle array 107 is deployed.

As mentioned above, the base 133 of the actuator 104 and/or the base 112 of the housing 102 can include the skin-contact adhesive 150 and any optional release liners 152. In such embodiments, the cover 113 (i.e., the first portion 140 thereof) can be configured to cover at least the portion of the base 133 (and/or the base 112) including the skin-contact adhesive 150 and, optionally, any release liners 152 employed, particularly when the actuator 104 is in the first position $P_1$. However, in some embodiments, after the apparatus 100 has been used and removed from the skin 50, the cover 113 can be used to re-cover the actuator 104 and the base 112 of the housing 102, with the actuator 104 in its second position $P_2$.

In the illustrated embodiment, the first portion 140 and the second portion 142 of the cover 113 are integrally formed together. However, in some embodiments, the first and second portions 140 and 142 can be removably coupled together, which can allow the base 133 (and/or the base 112) to be covered and/or uncovered independently of the microneedles 108.

By way of example only, the second portion 142 is illustrated as being generally tubular in shape, such that the second portion 142 can extend through the opening 135 (and/or the opening 115) in the base 133 (and/or the base 112) and into the cavity 134 of the actuator 104 (and/or the cavity 114 of the housing 112).

As shown in FIG. 25, the first portion 140 can include or define a recess (or chamber or pocket) 195 (i.e., with a closed end 197) dimensioned to receive at least a portion of the base 133 of the actuator 104 and/or at least a portion of the base 112 of the housing 102. In embodiments in which the cover 113 covers the actuator 104, the closed end or base 197 of the recess 195 can be spaced a distance from the base 133 of the actuator 104 when the cover 113 is coupled to the apparatus 100, such that the actuator 104 is not undesirably or prematurely actuated 104 prior to use.

As further shown, the second portion 142 can include or define a recess (or chamber or pocket) 196 (i.e., with a closed end 198) dimensioned to receive the plurality of microneedles 108 protruding from the first major surface of the first side 116 of the microneedle array 107. The recess 196 (e.g., the closed end 198) in the second portion 142 can be at least partially defined by an inner surface, and the inner surface of the recess 196 and the first side 116 of the microneedle array 107 can together define a sterile chamber for housing the plurality of microneedles 108 after assembly of the apparatus 100 and prior to use. Such a sterile chamber can allow sterilizing agent(s) free access to the enclosed volume, while keeping contaminants from entering the chamber post-sterilization.

As further shown in FIG. 25, in some embodiments, the second portion 142 of the cover 113 can include at least one of a projection and a recess, and the first side 116 of the microneedle array 107 (and/or the first side 121 of the holder 106) can include at least one of a recess and a projection, respectively, dimensioned to receive the projection and/or project into the recess of the second portion 142 of the cover 113. Such an arrangement can allow the second portion 142 to matingly engage with the microneedle array 107 (and/or the holder 106) and to facilitate housing and protecting the microneedle array 107 with the second portion 142 of the cover 113.

As shown in FIGS. 3 and 25, in the illustrated embodiment, a microneedle-facing (e.g., an upwardly-facing) recess 199 is illustrated in the second portion 142 of the cover 113 by way of example. As shown, the first side 116 of the microneedle array 107 can include a cover-facing (e.g., a downwardly-facing) recess 139 that surrounds the plurality of microneedles 108. As shown in FIGS. 3, 4 and 6, a sealing member 136 can be employed that is dimensioned to be received in the recess 199 in the second portion 142 of the cover 113 and the recess 139 in the microneedle array 107 to seal or close the chamber configured to house the microneedles 108 and to provide additional spacing between the closed end 198 of the recess 196 of the second portion 142 of the cover 113 and the first side 116 of the microneedle array 107. This specific arrangement is shown by way of example only, but generally, the second portion 142 of the cover 113 can be configured to be coupled in some way to the first side 116 of the microneedle array 107 (and/or the holder 106) to enclose and protect the plurality of microneedles 108 prior to use, i.e., to maintain the sterility of the microneedles 108. In some embodiments, the sealing member 136 and/or a portion of the cover 113 can be permeable to sterilizing agent(s)) while inhibiting contaminants from entering the chamber after sterilization. In some embodiments, the second portion 142 can include or provide the sealing member 136. In such embodiments, the sealing member 136 may be integrally formed with the cover 113 and configured to be coupled to at least one of the first side 116 of the microneedle array 107 and the first side 121 of the microneedle array holder 106.

As mentioned above, the housing 102 can include a protrusion 119 that defines or includes the base 112. The actuator 104 (e.g., the outer portion 132 thereof) can extend outwardly (e.g., downwardly) from the protrusion, e.g., when the actuator 104 is in its first position $P_1$. The recess 195 in the first portion 140 of the cover 113 can be dimensioned to receive the protrusion of the housing 119 and/or at least a portion of the outer portion 132 of the actuator 104.

The cover 113 can be configured to be coupled to the housing 102 (e.g., the protrusion 119) and/or the actuator 104 by any of the coupling means described above. The cover 113 can also be configured to abut a portion of the housing 102 from which the protrusion 119 projects, which can facilitate inhibiting the cover 113 from pressing the actuator 104 when the cover 113 is coupled to the apparatus 100 to prevent premature actuation of the actuator 104.

While the embodiment of FIGS. 1-25 employs a specific configuration and arrangement of elements and stored energy devices to accomplish injection and infusion, it should be understood that variations to the specific structures and arrangements shown in the illustrated embodiment are within the spirit and scope of the present disclosure.

Figure 26:
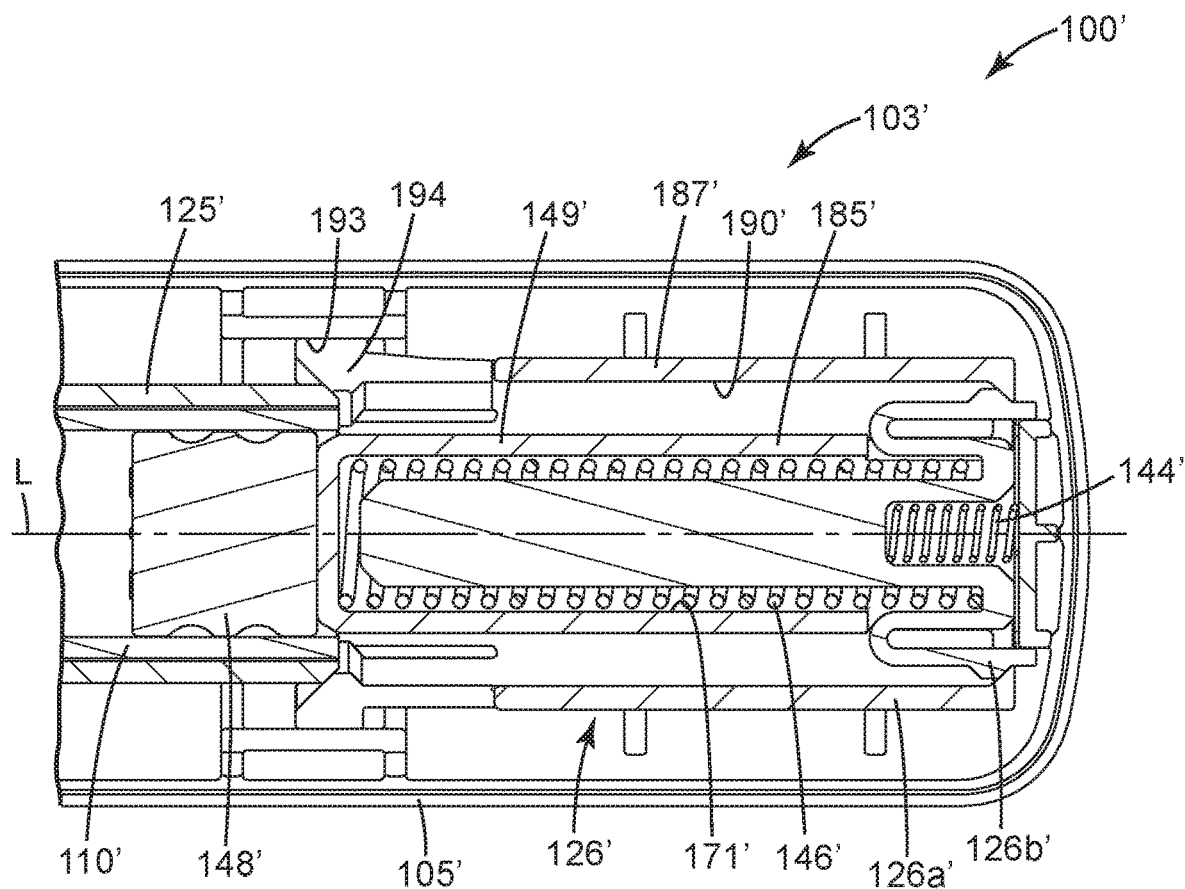
FIG. 26 is a top cross-sectional view of a portion of an infusion assembly according to another embodiment of the present disclosure.

For example, FIG. 26 illustrates an apparatus 100' according to another embodiment of the present disclosure, and particularly, a portion of an infusion assembly 103' according to another embodiment of the present disclosure. In some embodiments, as shown in FIG. 26, the third stored energy device 146' can be configured to directly (rather than indirectly) engage the plunger 149' and/or the piston 148', and the indicator 126' (e.g., the outer portion 187' thereof) can still include an outer recess 190' configured to receive at least a portion of the shuttle 125' and can ride along the outer surface of the shuttle 125' between the shuttle 125' and one or more retaining walls 105' of the housing 102' in order to be visible through a window of the housing 102' to indicate the progression of infusion.

For example, in such embodiments, the third stored energy device 146' can be located within the internal chamber 171' of the inner portion 185' of the indicator 126' that defines the plunger 149' (i.e., as opposed to being located between an outer surface of the shuttle 125 and the outer portion 187' of the indicator 126). A front end or wall of the plunger 149' can still contact the piston 148'. Furthermore, in such embodiments, the second stored energy device 144' can still initiate the movement of the shuttle 125' as well as the decoupling of first and second indicator portions 125a' and 125b'. Similar to the apparatus 100 of FIGS. 1-25, in the apparatus 100', the first indicator portion 126a' is located between the shuttle 125' and the second indicator portion 126b' (and provides coupling therebetween). Still further, the indicator 126' (or a portion thereof, particularly, the first indicator portion 126a') can travel with the shuttle 125' until the shuttle 125' reaches its second position, after which, the outer portion 187' can reach a longitudinal location along longitudinal axis L' that is beyond a retaining wall 193, allowing the walls forming the outer portion 187' of the indicator 126' to flex outwardly. At that point, the third stored energy device 146' can provide forces to overcome a latch or detent 194 coupling the indicator 126' (i.e., the first indicator portion 126a') and the shuttle 125', allowing the indicator 126' to begin to move along the longitudinal axis L', relative to the shuttle 125', allowing the shuttle 125' to ride inside the outer portion 187' (i.e., in the outer recess 190') to drive the piston 148' in the cartridge 110' to infuse an active agent.

Each embodiment shown in the figures is illustrated as a separate embodiment for clarity in illustrating a variety of features of the apparatuses of the present disclosure. However, it should be understood that any combination of elements and features of any of the embodiments illustrated in the figures and described herein can be employed in the apparatuses of the present disclosure.

The following descriptions of the application time, microneedles, skin-contact adhesive, release liners, and active agents can apply to any embodiment of the apparatuses of the present disclosure.

In some embodiments, the length of time that apparatuses of the present disclosure can remain on the skin 50 may be an extended time, however, apparatuses of the present disclosure are more likely to remain on the skin 50 for shorter durations of time. For example, in some embodiments, apparatuses of the present disclosure can remain on the skin for a treatment period of at least 1 second, in some embodiments, at least 5 seconds, in some embodiments, at least 10 seconds, in some embodiments, at least 15 seconds, and in some embodiments, at least 30 seconds. In some embodiments, the apparatus can remain on the skin for a period of time of no greater than 1 hour, in some embodiments, no greater than 30 minutes, in some embodiments, no greater than 20 minutes, in some embodiments, no greater than 10 minutes, and in some embodiments, no greater than 5 minutes. In some embodiments, the apparatuses can remain on the skin for a treatment period of from 1 second to 1 hour, in some embodiments, from 10 seconds to 10 minutes, and in some embodiments, from 30 seconds to 5 minutes.

In some embodiments, the apparatus 100 can be configured to deliver an active agent over an infusion period of at least 1 second, in some embodiments, at least 5 seconds, in some embodiments, at least 10 seconds, in some embodiments, at least 15 seconds, and in some embodiments, at least 30 seconds. In some embodiments, apparatuses of the present disclosure can include infusion periods of no greater than no greater than 1 hour, in some embodiments, no greater than 30 minutes, in some embodiments, no greater than 20 minutes, in some embodiments, no greater than 10 minutes, and in some embodiments, no greater than 5 minutes. In some embodiments, the apparatuses can remain on the skin for a treatment period of from 1 second to 1 hour, in some embodiments, from 10 seconds to 10 minutes, and in some embodiments, from 30 seconds to 5 minutes.

Skin-Contact Adhesive

In some embodiments, the skin-contact adhesive 150 can cover the entire base 133 of the actuator 104 (and/or the base 112 of the housing 102). Alternatively, in some embodiments, the skin-contact adhesive 150 can partially cover the base 133 (and/or the base 112), e.g., including intermittent application of the skin-contact adhesive 150 to create gaps (e.g., randomly, or in a pattern), and/or a complete ring of skin-contact adhesive 150 that has a width that is less than the width of the base 133 (and/or the base 112).

The skin-contact adhesive 150 is generally a pressure-sensitive adhesive, and particularly is a pressure-sensitive adhesive that is capable of securely but releasably adhering or bonding to skin (e.g., mammalian skin). The skin-contact adhesive 150 is also generally safe and non-toxic. Skin-contact adhesive layers will generally be selected according to the desired end use of the apparatus 100. In some embodiments, the apparatus 100 can include more than one skin-contact adhesive 150. Where the apparatus 100 comprises more than one skin-contact adhesive layer 150, each skin-contact adhesive layer 150 may be selected independently of each other with regard to material and thickness used. Examples of suitable adhesives include acrylates, silicones, polyisobutylenes, synthetic rubber, natural rubber, and copolymers and mixtures thereof. Acrylates and silicones can be preferred skin-contact adhesives 150. In general, the skin-contact adhesive 150 should cause little or no irritation or sensitization of the skin during the intended wear period.

In some embodiments, the skin-contact adhesive 150 can be an acrylate (or methacrylate) copolymer. Acrylates will typically have an inherent viscosity greater than about 0.2 dL/g and will comprise one or more polymerized primary monomers and optionally one or more polar comonomers. Primary monomers suitable for use include alkyl acrylates containing 4 to 12 carbon atoms in the alkyl group and alkyl methacrylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. In some embodiments, the alkyl acrylates can include isooctyl acrylate, 2-ethylhexyl acrylate, n-butyl acrylate, and cyclohexyl acrylate. Polar monomers suitable for use can include those having hydroxyl, amide, or carboxylic, sulfonic, or phosphonic acid functionality. Representative examples include acrylamide, methacrylamide, N-vinyl-2-pyrrolidone, 2-hydroxyethylacrylate, 2-hydroxyethylmethacrylate, hydroxypropylacrylate, acrylic acid, methacrylic acid, pyrrolidonyl ethyl acrylate, and alkoxyethyl acrylates, such as 2-carboxyethylacrylate. In some embodiments, the amount by weight of polar monomer will not exceed about 40% of the total weight of all monomers in order to avoid excessive firmness of the final PSA product. Typically, polar monomers can be incorporated to the extent of about 1% to about 20% by weight. In some embodiments, the polar monomer can be acrylamide.

In some embodiments, the acrylate copolymer can comprise the reaction product of primary and polar monomers and additional optional monomers which, when present, are included in the polymerization reaction in quantities that will not render the adhesive composition non-tacky. The optional additional monomers may be added, for example, to improve performance, reduce cost, or for other purposes. Examples of such optional monomers include vinyl esters, such as vinyl acetate, vinyl chloride, vinylidene chloride, styrene, and macromonomers copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference.

Silicone or polysiloxane pressure-sensitive adhesives include pressure-sensitive adhesives which are based on two major components: a polymer, or gum, and a tackifying resin. The polysiloxane adhesive can be prepared by cross-linking the gum, typically a high molecular weight polydiorganosiloxane, with the resin, to produce a three-dimensional silicate structure, via a condensation reaction in an appropriate organic solvent. The ratio of resin to polymer can be adjusted in order to modify the physical properties of polysiloxane adhesives. Use of capped (or amine-compatible) polysiloxanes can, in some embodiments, be preferred so as to increase drug stability and reduce degradation. Further details and examples of silicone pressure-sensitive adhesives which can be useful are described in the U.S. Pat. No. 4,591,622 (Blizzard et al.); U.S. Pat. No. 4,584,355 (Blizzard et al.); U.S. Pat. No. 4,585,836 (Homan et al.); and U.S. Pat. No. 4,655,767 (Woodard et al.). Suitable silicone pressure-sensitive adhesives are commercially available and include the silicone adhesives sold under the trademarks BIO-PSA® by Dow Corning Corporation, Medical Products, Midland, Mich.

Further description of suitable adhesives may be found in U.S. Pat. No. 5,656,286 (Miranda et al.), U.S. Pat. No. 5,223,261 (Nelson et al.), and U.S. Pat. No. 5,380,760 (Wendel et al.), the disclosures of which are incorporated herein by reference. In some embodiments, the thickness of the skin-contact adhesive 150 can be at least about 10 μm, in some embodiments, at least about 20 μm, and in some embodiments, at least about 40 μm. In some embodiments, the thickness of the skin-contact adhesive 150 can be less than about 2 mm (0.07874 inch), in some embodiments, less than about 1 mm (0.03937 inch), and in some embodiments, less than about 150 microns (5906 microinches).

In some embodiments, a medical grade adhesive can be preferred for the skin-contact adhesive 150. Such a medical grade skin-contact adhesive 150 is can have physical properties and characteristics to be capable of maintaining intimate contact with the skin 50 before, during, and after actuation of the apparatus 100. Securing the actuator 104 (or the housing 102) to the skin 50 can aid in keeping the microneedles 108 inserted into the skin 50.

Release Liners

Release liners, which can be used as at least a portion the release liner 152 (in addition to other release liners that are employed, e.g., to cover at least a portion of the base 112), are available from a variety of manufacturers in a wide variety of proprietary formulations. Those skilled in the art will normally test those liners in simulated use conditions against an adhesive of choice to arrive at a product with the desired release characteristics. Liners which can be suitable for use in apparatuses of the present disclosure can be made of kraft papers, polyethylene, polypropylene, polyester or composites of any of these materials. The liner material can be coated with release agents or low adhesion coatings, such as fluorochemicals or silicones. For example, U.S. Pat. No. 4,472,480 (Olson), the disclosure of which is hereby incorporated by reference, describes low surface energy perfluorochemical liners. The liners can be papers, polyolefin films, or polyester films coated with silicone release materials. Examples of commercially available silicone coated release papers are POLYSLIK® silicone release papers available from Loparex (Willowbrook, Ill.).

Active Agent

As mentioned above, in some embodiments, active ingredients or agents (e.g., drugs) can be delivered via the hollow microneedles 108. Any substance that can be formulated in a fluid and delivered via hypodermic injection may be used as the active agent, including any pharmaceutical, nutraceutical, cosmeceutical, diagnostic, and therapeutic agents (collectively referred to herein as "drug" for convenience). The present description envisions that even a gaseous fluid may be utilized.

Examples of drugs that can be incorporated into the apparatuses of the present disclosure are those capable of local or systemic effect when administered to the skin. Some examples include buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as $H_2$ antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl]methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatriptan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; anti-obesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, interferon-gamma, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, peptide therapeutic agents (natural, synthetic, or recombinant) can be delivered via the hollow microneedles 108. Examples of peptide therapeutic agents that can be incorporated into the apparatuses of the present disclosure include parathyroid hormone (PTH), parathyroid hormone related protein (PTHrP), calcitonin, lysozyme, insulin, insulinotropic analogs, glatiramer acetate, goserelin acetate, somatostatin, octreotide, leuprolide, vasopressin, desmopressin, thymosin alpha-1, atrial natriuretic peptide (ANP), endorphin, vascular endothelial growth factor (VEGF), fibroblast-growth factor (FGF), erythropoietin (EPO), bone morphogenetic proteins (BMPs), epidermal growth factor (EFG), granulocyte colony-stimulating factor (G-CSF), granulocyte macrophage colony stimulating factor (GM-CSF), insulin-like growth factor (IGF), platelet-derived growth factor (PDGF), growth hormone release hormone (GHRH), dornase alfa, tissue plasminogen activator (tPA), urokinase, ANP clearance inhibitors, lutenizing hormone releasing hormone (LHRH), melanocyte stimulating hormones (alpha & beta MSH), pituitary hormones (hGH), adrenocorticotropic hormone (ACTH), human chorionic gonadotropin (hCG), streptokinase, interleukins (e.g. IL-2, IL-4, IL-10, IL-12, IL-15, IL-18), protein C, protein S, angiotensin, angiogenin, endothelins, pentigetide, brain natriuretic peptide (BNP), neuropeptide Y, islet amyloid polypeptide (IAPP), vasoactive intestinal peptide (VIP), hirudin, glucagon, oxytocin, and derivatives of any of the foregoing peptide therapeutic agents.

In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Patent Application Publication No. 2004/0049150 (Dalton et al.), the disclosure of which is hereby incorporated by reference.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

Microneedles

Microneedle arrays useful for practicing the present disclosure can have a variety of configurations and features, such as those described in the following patents and patent applications, the disclosures of which are incorporated herein by reference. One embodiment for the microneedle arrays includes the structures disclosed in U.S. Patent Application Publication No. 2005/0261631 (Clarke et al.), which describes microneedles having a truncated tapered shape and a controlled aspect ratio. Another embodiment for the microneedle arrays includes the structures disclosed in U.S. Pat. No. 6,091,975 (Daddona et al.), which describes blade-like microprotrusions for piercing the skin. Still another embodiment for the microneedle arrays includes the structures disclosed in U.S. Pat. No. 6,312,612 (Sherman et al.), which describes tapered structures having a hollow central channel Yet still another embodiment for the microneedle arrays includes the structures disclosed in U.S. Pat. No. 6,379,324 (Gartstein et al.), which describes hollow microneedles having at least one longitudinal blade at the top surface of the tip of the microneedle. A further embodiment for the microneedle arrays includes the structures disclosed in U.S. Patent Application Publication Nos. US2012/0123387 (Gonzalez et al.) and US2011/0213335 (Burton et al.), which both describe hollow microneedles. A still further embodiment for the microneedle arrays includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of microneedles that can be employed in the microneedle arrays of the present disclosure are described in PCT Publication No. WO 2012/074576 (Duan et al.), which describes liquid crystalline polymer (LCP) microneedles; and PCT Publication No. WO 2012/122162 (Zhang et al.), which describes a variety of different types and compositions of microneedles that can be employed in the microneedles of the present disclosure.

In some embodiments, the microneedle material can be (or include) silicon, glass, or a metal such as stainless steel, titanium, or nickel titanium alloy. In some embodiments, the microneedle material can be (or include) a polymeric material, such as a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Particularly useful types of medical grade polymeric materials include polycarbonate and LCP.

In some embodiments, the microneedle material can be (or include) a biodegradable polymeric material, particularly, a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the microneedles can be a prepared from a dissolvable, degradable, or disintegradable material referred to herein as "dissolvable microneedles". A dissolvable, degradable, or disintegradable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In some embodiments, the microneedles can be made from (or include) a combination of two or more of any of the above mentioned materials. For example, the tip of a microneedle may be a dissolvable material, while the remainder of the microneedle is a medical grade polymeric material.

A microneedle or the plurality of microneedles in a microneedle array useful for practicing the present disclosure can have a variety of shapes that are capable of piercing the stratum corneum. In some embodiments, one or more of the plurality of microneedles can have a square pyramidal shape, triangular pyramidal shape, stepped pyramidal shape, conical shape, microblade shape, or the shape of a hypodermic needle. In some embodiments, one or more of the plurality of microneedles can have a square pyramidal shape. In some embodiments, one or more of the plurality of microneedles can have a triangular pyramidal shape. In some embodiments, one or more of the plurality of microneedles can have a stepped pyramidal shape. In some embodiments, one or more of the plurality of microneedles can have a conical shape. In some embodiments, one or more of the plurality of microneedles can have a microblade shape. In some embodiments, one or more of the plurality of microneedles can have the shape of a hypodermic needle. The shape can be symmetric or asymmetric. The shape can be truncated (for example, the plurality of microneedles can have a truncated pyramid shape or truncated cone shape). The plurality of microneedles in a microneedle array are preferably hollow microneedles (that is, the microneedles contain a hollow bore through the microneedle). The hollow bore can be from the base of the microneedle to the tip of the microneedle or the bore can be from the base of the microneedle to a position offset from the tip of the microneedle. In some embodiments, one or more of the plurality of hollow microneedles in a hollow microneedle array can have a conical shape, cylindrical shape, square pyramidal shape, triangular pyramidal shape, or the shape of a hypodermic needle.

In some embodiments, one or more of the plurality of hollow microneedles in a hollow microneedle array can have a conical shape. In some embodiments, one or more of the plurality of hollow microneedles in a hollow microneedle array can have a cylindrical shape. In some embodiments, one or more of the plurality of hollow microneedles in a hollow microneedle array can have a square pyramidal shape. In some embodiments, one or more of the plurality of hollow microneedles in a hollow microneedle array can have a triangular pyramidal shape. In some embodiments, one or more of the plurality of hollow microneedles in a hollow microneedle array can have the shape of a hypodermic needle. In a preferred embodiment, the plurality of hollow microneedles in a hollow microneedle array each have the shape of a conventional hypodermic needle.

Figure 27:
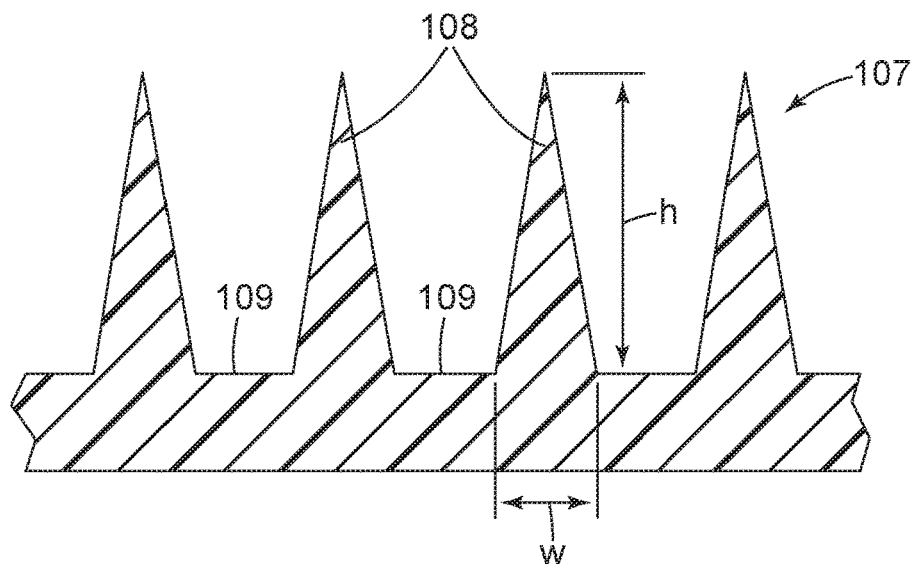
FIG. 27 is a close-up side cross-sectional view of an exemplary microneedle array that can be employed with the apparatus of FIGS. 1-25, the microneedle array shown with the microneedles pointing upwardly.

FIG. 27 shows a portion of the microneedle array 107 that includes four microneedles 108 (of which two are referenced in FIG. 27) positioned on a microneedle substrate 109. Each microneedle 108 has a height h, which is the length from the tip of the microneedle 108 to the microneedle base at substrate 109. Either the height of a single microneedle or the average height of all microneedles on the microneedle array can be referred to as the height of the microneedle, h. In some embodiments, each of the plurality of microneedles (or the average of all of the plurality of microneedles) has a height of about 100 to about 3000 micrometers, in some embodiments, about 100 to about 1500 micrometers, in some embodiments, about 100 to about 1200 micrometers, and, in some embodiments, about 100 to about 1000 micrometers.

In some embodiments, each of the plurality of microneedles (or the average of all of the plurality of microneedles) has a height of about 200 to about 1200 micrometers, about 200 to about 1000 micrometers, about 200 to about 750 micrometers, or about 200 to about 600 micrometers.

In some embodiments, each of the plurality of microneedles (or the average of all of the plurality of microneedles) has a height of about 250 to about 1500 micrometers, about 500 to about 1000 micrometers, or about 500 to about 750 micrometers.

In some embodiments, each of the plurality of microneedles (or the average of all of the plurality of microneedles) has a height of about 800 to about 1400 micrometers.

In some embodiments, each of the plurality of microneedles (or the average of all of the plurality of microneedles) has a height of about 500.

In some embodiments, each of the plurality of microneedles (or the average of all of the plurality of microneedles) has a height of less than about 3000 micrometers. In other embodiments, each of the plurality of microneedles (or the average of all of the plurality of microneedles) has a height of less than about 1500 micrometers. In still other embodiments, each of the plurality of microneedles (or the average of all of the plurality of microneedles) has a height of less than about 1200 micrometers. In yet still other embodiments, each of the plurality of microneedles (or the average of all of the plurality of microneedles) has a height of less than about 1000 micrometers. In further embodiments, each of the plurality of microneedles (or the average of all of the plurality of microneedles) has a height of less than about 750 micrometers. In still further embodiments, each of the plurality of microneedles (or the average of all of the plurality of microneedles) has a height of less than about 600 micrometers.

In some embodiments, each of the plurality of microneedles (or the average of all of the plurality of microneedles) has a height of at least about 100 micrometers. In other embodiments, each of the plurality of microneedles (or the average of all of the plurality of microneedles) has a height of at least about 200 micrometers. In still other embodiments, each of the plurality of microneedles (or the average of all of the plurality of microneedles) has a height of at least about 250 micrometers. In further embodiments, each of the plurality of microneedles (or the average of all of the plurality of microneedles) has a height of at least about 500 micrometers. In still further embodiments, each of the plurality of microneedles (or the average of all of the plurality of microneedles) has a height of at least about 800 micrometers.

In some embodiments employing hollow microneedles, each of the plurality of hollow microneedles (or the average of all of the plurality of hollow microneedles) has a height of about 100 to about 3000 micrometers, about 800 to about 1400 micrometers, or about 500 micrometers.

In some embodiments, each of the plurality of hollow microneedles (or the average of all of the plurality of hollow microneedles) has a height of about 900 to about 1000 micrometers. In other embodiments, each of the plurality of hollow microneedles (or the average of all of the plurality of hollow microneedles) has a height of about 900 to about 950 micrometers. In still other embodiments, each of the plurality of hollow microneedles (or the average of all of the plurality of hollow microneedles) has a height of about 900 micrometers.

A single microneedle or the plurality of microneedles in a microneedle array can also be characterized by their aspect ratio. The aspect ratio of a microneedle is the ratio of the height of the microneedle, h to the width (at the base of the microneedle), w (as shown in FIG. 27). The aspect ratio can be presented as h:w. In some embodiments, each of the plurality of microneedles (or the average of all the plurality of microneedles) has (have) an aspect ratio in the range of 2:1 to 5:1. In some of these embodiments, each of the plurality of microneedles (or the average of all of the plurality of microneedles) has (have) an aspect ratio of at least 3:1.

In some embodiments, the array of microneedles contains about 100 to about 1500 microneedles per $cm^2$ of the array of microneedles.

In some embodiments employing hollow microneedles, the array of hollow microneedles contains about 3 to about 30 hollow microneedles per array of hollow microneedles.

In some embodiments, the array of hollow microneedles contains about 10 to about 30 hollow microneedles per array of hollow microneedles.

In some embodiments, the array of hollow microneedles contains about 3 to about 20 hollow microneedles per array of hollow microneedles.

In some embodiments, the array of hollow microneedles contains about 13 to about 20 hollow microneedles per array of hollow microneedles.

In some embodiments, the array of hollow microneedles contains about 8 to about 18 hollow microneedles per array of hollow microneedles.

In some embodiments, the array of hollow microneedles contains about 18 hollow microneedles per array of hollow microneedles.

In some embodiments, the array of hollow microneedles contains about 12 hollow microneedles per array of hollow microneedles.

In some embodiments, each of the plurality of microneedles (or the average of all of the plurality of microneedles) in a microneedle array can penetrate into the skin to a depth of about 50 to about 1500 micrometers, about 50 to about 400 micrometers, or about 50 to about 250 micrometers.

In some embodiments, each of the plurality of microneedles (or the average of all of the plurality of microneedles) in a microneedle array can penetrate into the skin to a depth of about 100 to about 400 micrometers, or about 100 to about 300 micrometers.

In some embodiments, each of the plurality of microneedles (or the average of all of the plurality of microneedles) in a microneedle array can penetrate into the skin to a depth of about 150 to about 1500 micrometers, or about 800 to about 1500 micrometers.

In some embodiments, each of the plurality of microneedles (or the average of all of the plurality of microneedles) in a microneedle array can penetrate into the skin to a depth of about 400 to about 800 micrometers.

For all of the above embodiments, it will be appreciated that the depth of penetration (DOP) of each of the plurality of microneedles (or the average of all of the plurality of microneedles) in a microneedle array may not be the full length of the microneedles themselves.

In some embodiments, the microneedle array 107 according to the present disclosure can be in the form of a patch, which can include the microneedle array 107, a skin-contact adhesive, such as those described above, and optionally a backing. Whether on a patch or not, the microneedles 108 can be arranged in any desired pattern or arrangement. For example, the microneedles 108 can be arranged in uniformly spaced rows, which can be aligned or offset. In some embodiments, the microneedles 108 can be arranged in a polygonal pattern such as a triangle, square, rectangle, pentagon, hexagon, heptagon, octagon, or trapezoid. In other embodiments, the microneedles 108 can be arranged in a circular or oval pattern.

In some embodiments, the surface area of the substrate 109 covered with microneedles 108, can be about 0.1 $cm^2$ to about 20 $cm^2$. In some of these embodiments, the surface area of the substrate 109 covered with microneedles 108 is about 0.5 $cm^2$ to about 5 $cm^2$. In some other of these embodiments, the surface area of the substrate 109 covered with microneedles 108 is about 1 cm² to about 3 cm². In still other of these embodiments, the surface area of the substrate 109 covered with microneedles 108 is about 1 cm² to about 2 cm².

In some embodiments, the microneedles 108 of the present disclosure can be disposed over substantially the entire surface of the array 107 (e.g., of the substrate 109). In other embodiments, a portion of the substrate 109 may not be provided with microneedles 108 (that is, a portion of the substrate 109 is non-structured). In some of these embodiments, the non-structured surface has an area of more than about 1 percent and less than about 75 percent of the total area of the device surface that faces the skin surface 50. In another of these embodiments, the non-structured surface has an area of more than about 0.65 cm² (0.10 square inch) to less than about 6.5 cm² (1 square inch).

For hollow microneedles, a hollow channel or bore extends through the substrate 109 and microneedles 108. In some embodiments, the bore exits at a channel opening at or near the tip of the hollow microneedle. The channel preferably exits at an opening near the tip of the hollow microneedle. Most preferably, the channel or bore continues along a central axis of the microneedle, but exits similar to a hypodermic needle on a sloping side-wall of the microneedle to help prevent blockage of the channel by tissue upon insertion. In some embodiments, the diameter of the channel bore is about 10 to about 200 micrometers. In other embodiments, the diameter of the channel bore is about 10 to about 150 micrometers. In still other embodiments, the diameter of the channel bore is about 30 to about 60 micrometers.

In some embodiments of hollow microneedles, the average cross-sectional area of the channel bore is about 75 to about 32,000 micrometers. In other embodiments of hollow microneedles, the average cross-sectional area of the channel bore is about 75 to about 18,000 micrometers. In still other embodiments of hollow microneedles, the average cross-sectional area of the channel bore is about 700 to about 3,000 micrometers.

In some embodiments of hollow microneedle arrays, the average spacing between adjacent microneedles (as measured from microneedle tip to microneedle tip) is between about 0.7 mm and about 20 mm. In other embodiments of hollow microneedle arrays, the average spacing between adjacent microneedles is between about 0.7 mm and about 10 mm. In still other embodiments of hollow microneedle arrays, the average spacing between adjacent microneedles is between about 2 mm and about 20 mm. In still other embodiments of hollow microneedle arrays, the average spacing between adjacent microneedles is between about 2 mm and about 10 mm. In a preferred embodiment of hollow microneedle arrays, the average spacing between adjacent microneedles is between about 2 mm.

In some embodiments of hollow microneedle arrays, the average spacing between adjacent microneedles (as measured from microneedle tip to microneedle tip) is greater than about 0.7 mm. In other embodiments of hollow microneedle arrays, the average spacing between adjacent microneedles is greater than about 2 mm.

In some embodiments of hollow microneedle arrays, the average spacing between adjacent microneedles is less than about 20 mm. In other embodiments of hollow microneedle arrays, the average spacing between adjacent microneedles is less than about 10 mm.

The microneedle arrays can be manufactured in any suitable way such as by injection molding, compression molding, metal injection molding, stamping, photolithography, or extrusion. In one embodiment, hollow microneedle arrays can be made by thermocycled injection molding of a polymer such as medical grade polycarbonate or LCP, followed by laser drilling to form the channels of the microneedles.

The following embodiments are intended to be illustrative of the present disclosure and not limiting.

Embodiments

1. A microneedle injection and infusion apparatus comprising:
    a housing having a base and a cavity that extends through the base to define an opening in the base, wherein the base of the housing is configured to be positioned toward a skin surface;
    a microneedle array holder configured to hold a microneedle array and located in the housing, the microneedle array holder movable with respect to the opening in the base of the housing between
        a retracted position in which the microneedle array is recessed within the housing such that the microneedle array does not contact the skin surface when the apparatus is positioned on the skin surface and the microneedle array is coupled to the microneedle array holder, and
        extended position in which at least a portion of the microneedle array is positioned to contact the skin surface via the opening when the apparatus is positioned on the skin surface and the microneedle array is coupled to the microneedle array holder;
    a shuttle configured to hold and carry a cartridge, the cartridge defining a reservoir configured to contain an active agent, the shuttle being movable between a first position in which the reservoir of the cartridge is not in fluid communication with a fluid path and a second position in which the reservoir is in fluid communication with the fluid path; and
    an actuator movable between a first position and a second position, wherein movement of the actuator to the second position releases the shuttle from its first position and allows the shuttle to move toward its second position, and wherein movement of the shuttle toward its second position releases the microneedle array holder from the retracted position and allows the microneedle array holder to move to the extended position.

2. A method of using a microneedle injection apparatus, the method comprising:
    providing a microneedle injection apparatus comprising:
        a housing having a base and a cavity that extends through the base to define an opening in the base, wherein the base of the housing is configured to be positioned toward a skin surface;
        a microneedle array holder configured to hold a microneedle array and located in the housing, the microneedle array holder movable with respect to the opening in the base of the housing between
            a retracted position in which the microneedle array is recessed within the housing such that the microneedle array does not contact the skin surface when the apparatus is positioned on the skin surface and the microneedle array is coupled to the microneedle array holder, and
            an extended position in which at least a portion of the microneedle array is positioned to contact the skin surface via the opening when the apparatus is positioned on the skin surface and the microneedle array is coupled to the microneedle array holder;

a shuttle configured to hold and carry a cartridge, the cartridge defining a reservoir configured to contain an active agent, the shuttle being movable between a first position in which the reservoir is not in fluid communication with a fluid path and a second position in which the reservoir is in fluid communication with the fluid path; and an actuator movable between a first position and a second position;

moving the actuator to its second position to allow the shuttle to move toward its second position, wherein movement of the shuttle toward its second position allows the microneedle array holder to move to its extended position.

3. The method of embodiment 2, wherein the microneedle array holder is moved to its extended position prior to the shuttle being fully moved to its second position, such that the microneedle array holder is in its extended position before the shuttle is in its second position.

4. The method of embodiment 2 or 3, further comprising providing a delay between moving the microneedle array holder to its extended position and moving the shuttle to its second position.

5. The method of any of embodiments 2-4, wherein the microneedle array holder is moved to its extended position before the shuttle has completed movement to its second position.

6. The method of any of embodiments 2-5, wherein the microneedle array holder is in its extended position when the shuttle reaches its second position.

7. The apparatus of embodiment 1 or the method of any of embodiments 2-6, wherein the fluid path includes the microneedle array when the microneedle array is coupled to the microneedle array holder.

8. The apparatus of embodiment 1 or 7 or the method of any of embodiments 2-7, wherein the microneedle array includes a plurality of hollow microneedles, and wherein the fluid path includes the plurality of hollow microneedles.

9. The apparatus of any of embodiments 1, 7 and 8 or the method of any of embodiments 2-8, wherein the fluid path is configured to deliver the active agent to the microneedle array when the microneedle array is coupled to the microneedle array holder.

10. The apparatus of any of embodiments 1 and 7-9 or the method of any of embodiments 2-9, wherein the microneedle array includes a plurality of hollow microneedles, and wherein the fluid path is configured to deliver the active agent to the plurality of hollow microneedles when the microneedle array is coupled to the microneedle array holder.

11. The apparatus of any of embodiments 1 and 7-10 or the method of any of embodiments 2-10, wherein the fluid path is in fluid communication with the microneedle array when the microneedle array is coupled to the microneedle array holder.

12. The apparatus of any of embodiments 1 and 7-11 or the method of any of embodiments 2-11, wherein the microneedle array includes a plurality of hollow microneedles, and wherein the fluid path is in fluid communication with the plurality of hollow microneedles when the microneedle array is coupled to the microneedle array holder.

13. The apparatus of any of embodiments 1 and 7-12 or the method of any of embodiments 2-12, wherein the microneedle array includes a first side comprising a first major surface and a plurality of hollow microneedles that protrude from the first major surface.

14. The apparatus or method of embodiment 13, wherein the microneedle array includes a second side opposite the first side, wherein the plurality of hollow microneedles are in fluid communication with the second side, and wherein the microneedle array is configured to be coupled to a base of the microneedle array holder such that the second side of the microneedle array and the base of the microneedle array holder are spaced a distance apart to define a manifold for the plurality of hollow microneedles.

15. The apparatus of any of embodiments 1 and 7-14 or the method of any of embodiments 2-14, wherein the shuttle is biased in the second position, and wherein the microneedle array holder is biased in the extended position.

16. The apparatus of any of embodiments 1 and 7-15 or the method of any of embodiments 2-15, wherein the shuttle is held in its first position by the actuator when the actuator is in its first position.

17. The apparatus of any of embodiments 1 and 7-16 or the method of any of embodiments 2-16, wherein the microneedle array holder is held in the retracted position by the shuttle, when the shuttle is in its first position.

18. The apparatus of any of embodiments 1 and 7-17 or the method of any of embodiments 2-17, wherein at least a portion of the shuttle is configured to hold the actuator in the second position after the actuator has been moved to the second position.

19. The apparatus of any of embodiments 1 and 7-18 or the method of any of embodiments 2-18, wherein the actuator is held in its second position by the shuttle.

20. The apparatus of any of embodiments 1 and 7-19 or the method of any of embodiments 2-19, wherein the microneedle array holder is movable between the retracted position and the extended position along a first axis, wherein the shuttle is movable between the first position and the second position along a second axis, and wherein the first axis and the second axis are oriented at a non-zero angle with respect to one another.

21. The apparatus or method of embodiment 20, wherein the first axis and the second axis are oriented substantially perpendicularly with respect to one another.

22. The apparatus of any of embodiments 1 and 7-21 or the method of any of embodiments 2-21, wherein the actuator includes a shuttle stop movable between (i) a first position in which the shuttle stop is positioned to engage at least a portion of the shuttle to hold the shuttle in the first position, and (ii) a second position in which the shuttle stop is no longer positioned to engage the shuttle to hold the shuttle in the first position, such that when the shuttle stop is in the second position, the shuttle is free to move to the second position.

23. The apparatus or method of embodiment 22, wherein the shuttle is biased in the second position.

24. The apparatus or method of embodiment 22 or 23, further comprising a stored energy device configured to drive the shuttle toward the second position.

25. The apparatus or method of any of embodiments 22-24, wherein when the actuator is in the second position, the shuttle stop is positioned to hold the actuator in the second position.

26. The apparatus or method of any of embodiments 22-25, wherein when the actuator is in the second position, the shuttle stop is positioned to engage at least a portion of the shuttle to hold the actuator in the second position.

27. The apparatus or method of any of embodiments 22-26, wherein the actuator is held in the second position by an engagement between the shuttle stop and at least a portion of the shuttle.

28. The apparatus of any of embodiments 1 and 7-27 or the method of any of embodiments 2-27, wherein the shuttle includes a holder stop movable from (i) a first position in which the holder stop is positioned to engage with at least a portion of the microneedle array holder to hold the microneedle array holder in the retracted position to (ii) a second position in which the holder stop is no longer positioned to engage with the microneedle array holder to hold the microneedle array holder in the retracted position, such that when the holder stop is in the second position, the microneedle array holder is free to move to the extended position.

29. The apparatus or method of embodiment 28, wherein the microneedle array holder is biased in the extended position.

30. The apparatus or method of embodiment 28 or 29, further comprising a stored energy device configured to drive the microneedle array holder toward the extended position.

31. The apparatus of any of embodiments 1 and 7-30 or the method of any of embodiments 2-30, wherein at least a portion of the actuator is located on the base of the housing and is configured to be moved from the first position to the second position in response to the apparatus being pressed toward the skin surface.

32. The apparatus of any of embodiments 1 and 7-31 or the method of any of embodiments 2-31, wherein at least a portion of the actuator is located on a skin-facing portion of the apparatus and is configured to be moved from the first position to the second position in response to the apparatus being pressed toward a skin surface by pressing on a non-skin-facing portion of the apparatus.

33. The apparatus or method of embodiment 32, wherein the non-skin-facing portion of the apparatus is located in an off-axis position with respect to an actuation axis of the actuator.

34. The apparatus of any of embodiments 1 and 7-33 or the method of any of embodiments 2-33, wherein at least a portion of the actuator is located on a lower portion of the housing, and wherein the actuator is configured to be moved from the first position to the second position in response to the apparatus being pressed toward a skin surface by pressing on an upper portion of the housing.

35. The apparatus or method of embodiment 34, wherein the upper portion of the housing is located in an off-axis position with respect to an actuation axis of the actuator.

36. The apparatus of any of embodiments 1 and 7-35 or the method of any of embodiments 2-35, wherein the actuator is configured to be moved from the first position to the second position when a non-skin-facing portion of the housing is pressed toward a skin surface.

37. The apparatus or method of embodiment 36, wherein the non-skin-facing portion of the housing is not located directly opposite the actuator.

38. The apparatus or method of embodiment 36 or 37, wherein the non-skin-facing portion of the housing is located in an off-axis position with respect to an actuation axis of the actuator.

39. The apparatus of any of embodiments 1 and 7-38 or the method of any of embodiments 2-38, wherein the actuator is movable with respect to the base of the housing, and wherein when the actuator is in the first position, an outermost surface of the actuator extends beyond the base of the housing by a first distance, and when the actuator is in the second position, the outermost surface of the actuator
  does not extend beyond the base of the housing, or
  extends beyond the base of the housing by a second distance that is less than the first distance.

40. The apparatus of any of embodiments 1 and 7-39 or the method of any of embodiments 2-39, wherein the actuator is movable between the first position and the second position along a first actuation axis, wherein the microneedle array holder is movable between the retracted position and the extended position along a second actuation axis, and wherein the first actuation axis and the second actuation axis are substantially parallel with respect to one another.

41. The apparatus or method of embodiment 40, wherein at least a portion of the actuator extends beyond the base of the housing when the actuator is in the first position.

42. The apparatus or method of embodiment 40 or 41, wherein the first actuation axis and the second actuation axis are substantially aligned.

43. The apparatus or method of any of embodiments 40-42, wherein the shuttle is movable between the first position and the second position along a third axis, and wherein the third axis is oriented at a non-zero angle with respect to at least one of the first axis and the second axis.

44. The apparatus or method of any of embodiments 40-43, wherein the third axis is oriented substantially perpendicularly with respect to at least one of the first axis and the second axis.

45. The apparatus of any of embodiments 1 and 7-44 or the method of any of embodiments 2-44, wherein at least a portion of the housing is configured to be pressed using any portion of a hand.

46. The apparatus of any of embodiments 1 and 7-45 or the method of any of embodiments 2-45, wherein at least a portion of the actuator is movable with respect to the base of the housing into and out of the opening formed in the base of the housing.

47. The apparatus of any of embodiments 1 and 7-46 or the method of any of embodiments 2-46, wherein at least a portion of the actuator extends into the cavity of the housing.

48. The apparatus of any of embodiments 1 and 7-47 or the method of any of embodiments 2-47, wherein the actuator includes a base and a cavity that extends through the base of the actuator to form an opening in the base of the actuator, and wherein the microneedle array holder is movable in the cavity of the actuator when the microneedle array holder is moved between the retracted position and the extended position.

49. The apparatus or method of embodiment 48, wherein the actuator includes a base and an opening formed in the base, and wherein at least a portion of the microneedle array extends through the opening in the actuator and beyond the base of the actuator when the microneedle array holder is in the extended position.

50. The apparatus or method of embodiment 49, wherein the base of the actuator is configured to be coupled to the skin surface.

51. The apparatus or method of embodiment 49 or 50, wherein the base of the actuator includes a skin-contact adhesive.

52. The apparatus of any of embodiments 1 and 7-51 or the method of any of embodiments 2-51, wherein the actuator includes a skin-contact adhesive.

53. The apparatus of any of embodiments 1 and 7-52 or the method of any of embodiments 2-52, wherein, when the actuator is in the first position, at least a portion of the actuator protrudes from the opening in the base of the housing and defines a base configured to be coupled to the skin surface.

54. The apparatus or method of embodiment 53, wherein the first surface includes a skin-contact adhesive.

55. The apparatus of any of embodiments 1 and 7-54 or the method of any of embodiments 2-54, wherein at least a portion of the actuator is located in the cavity of the housing and positioned to at least partially surround the microneedle array, at least when the microneedle array holder is in the extended position.

56. The apparatus of any of embodiments 1 and 7-55 or the method of any of embodiments 2-55, wherein at least a portion of the actuator is located adjacent the opening in the base of the housing, and wherein at least a portion of the microneedle array extends beyond the actuator when the microneedle array holder is in the extended position.

57. The apparatus of any of embodiments 1 and 7-56 or the method of any of embodiments 2-56, wherein the actuator is biased in the first position.

58. The apparatus of embodiment any of embodiments 1 and 7-57 or the method of any of embodiments 2-57, further comprising a biasing element configured to bias the actuator in the first position, wherein the actuator is movable from the first position to the second position against the bias of the biasing element.

59. The apparatus of any of embodiments 1 and 7-58 or the method of any of embodiments 2-58, wherein the microneedle array holder is biased in the extended position.

60. The apparatus of any of embodiments 1 and 7-59 or the method of any of embodiments 2-59, wherein the shuttle is biased toward the second position, and wherein the shuttle is restrained from moving to the second position by the actuator, until the actuator is moved to the second position.

61. The apparatus of any of embodiments 1 and 7-60 or the method of any of embodiments 2-60, further comprising a stored energy device configured to drive the shuttle toward the second position.

62. The apparatus or method of embodiment 61, wherein the stored energy device is one of a plurality of stored energy devices that cooperate to drive the shuttle toward the second position.

63. The apparatus of any of embodiments 1 and 7-62 or the method of any of embodiments 2-62, further comprising an active agent and a piston located in the reservoir of the cartridge, the piston movable between a first position in which the active agent is not being forced out of the reservoir and moved into the fluid path and a second position in which the active agent is being forced out of the reservoir and moved into the fluid path.

64. The apparatus or method of embodiment 63, further comprising a stored energy device configured to drive the shuttle toward the second position, wherein the stored energy device is further configured to drive the piston toward its second position.

65. The apparatus or method of embodiment 63 or 64, further comprising a first stored energy device configured to initiate movement of the shuttle toward the second position and a second stored energy device configured to assist in moving the shuttle toward the second position and further configured to drive the piston toward its second position.

66. The apparatus or method of any of embodiments 63-65, wherein the piston is movable to the second position when the shuttle is in its second position.

67. The apparatus or method of any of embodiments 63-66, further comprising an indicator that is movable with the piston between the first position and the second position of the piston, wherein the indicator is visible from outside the housing to indicate the position of the piston with respect to the housing.

68. The apparatus or method of embodiment 67, wherein the indicator is movable with the shuttle from the first position of the shuttle to the second position of the shuttle, and wherein the indicator is further movable with the piston and with respect to the shuttle when the shuttle is in the second position.

69. The apparatus or method of embodiment 67 or 68, wherein the indicator is formed of at least two portions that are removably coupled together.

70. The apparatus or method of any of embodiments 67-69, wherein at least a portion of the indicator is movable with respect to the shuttle when the shuttle is in the second position.

71. The apparatus or method of any of embodiments 67-70, wherein at least a portion of the indicator is coupled to a plunger that is configured to abut the piston.

72. The apparatus or method of embodiment 71, wherein the plunger is positioned to drive the piston to its second position.

73. The apparatus of any of embodiments 1 and 7-72 or the method of any of embodiments 2-72, wherein the fluid path includes or is in fluid communication with a piercing element configured to provide fluid communication between the reservoir of the cartridge and the fluid path, and further comprising a deformable sterility seal positioned to enclose the piercing element and configured to be pierced by the piercing element.

74. The apparatus or method of embodiment 73, wherein the sterility seal is further configured to be changed from a first state in which the sterility seal defines a sterile chamber within which the piercing element is located to a second state in which the sterility seal has been pierced by the piercing element and the sterility seal is collapsed.

75. The apparatus of any of embodiments 1 and 7-74 or the method of any of embodiments 2-74, further comprising a dampener positioned to dampen movement of the microneedle array holder from the retracted position to the extended position.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A microneedle injection and infusion apparatus comprising:
a housing having a base and a cavity that extends through the base to define an opening in the base, wherein the base of the housing is configured to be positioned toward a skin surface;
a microneedle array holder configured to hold a microneedle array and located in the housing, the microneedle array holder movable with respect to the opening in the base of the housing between
a retracted position in which the microneedle array is recessed within the housing such that the microneedle array does not contact the skin surface when the apparatus is positioned on the skin surface and the microneedle array is coupled to the microneedle array holder, and an extended position in which at least a portion of the microneedle array is positioned to contact the skin surface via the opening when the apparatus is positioned on the skin surface and the microneedle array is coupled to the microneedle array holder;

a shuttle configured to hold and carry a cartridge, the cartridge defining a reservoir configured to contain an active agent, the shuttle being movable between a first position in which the reservoir of the cartridge is not in fluid communication with a fluid path and a second position in which the reservoir is in fluid communication with the fluid path; and an actuator movable between a first position and a second position, wherein movement of the actuator to the second position releases the shuttle from its first position and allows the shuttle to move toward its second position, and wherein movement of the shuttle toward its second position releases the microneedle array holder from the retracted position and allows the microneedle array holder to move to the extended position;

wherein at least a portion of the actuator is located on a lower portion of the housing, wherein the actuator is configured to be moved from the first position to the second position in response to the apparatus being pressed toward a skin surface by pressing on an upper portion of the housing, and wherein the upper portion of the housing is located in an off-axis position with respect to an actuation axis of the actuator.

2. The apparatus of claim 1, wherein the microneedle array includes a plurality of hollow microneedles, and wherein the fluid path is configured to deliver the active agent to the plurality of hollow microneedles when the microneedle array is coupled to the microneedle array holder.

3. The apparatus of claim 1, wherein the microneedle array includes a first side comprising a first major surface and a plurality of hollow microneedles that protrude from the first major surface, wherein the microneedle array includes a second side opposite the first side, wherein the plurality of hollow microneedles are in fluid communication with the second side, and wherein the microneedle array is configured to be coupled to a base of the microneedle array holder such that the second side of the microneedle array and the base of the microneedle array holder are spaced a distance apart to define a manifold for the plurality of hollow microneedles.

4. The apparatus of claim 1, wherein the shuttle is biased in the second position, and wherein the microneedle array holder is biased in the extended position.

5. The apparatus of claim 1, wherein the microneedle array holder is held in the retracted position by the shuttle, when the shuttle is in its first position.

6. The apparatus of claim 1, wherein at least a portion of the shuttle is configured to hold the actuator in the second position after the actuator has been moved to the second position.

7. The apparatus of claim 1, wherein the actuator is held in its second position by the shuttle.

8. The apparatus of claim 1, wherein the microneedle array holder is movable between the retracted position and the extended position along a first axis, wherein the shuttle is movable between the first position and the second position along a second axis, and wherein the first axis and the second axis are oriented at a non-zero angle with respect to one another.

9. The apparatus of claim 1, wherein the actuator includes a shuttle stop movable between (i) a first position in which the shuttle stop is positioned to engage at least a portion of the shuttle to hold the shuttle in the first position, and (ii) a second position in which the shuttle stop is no longer positioned to engage the shuttle to hold the shuttle in the first position, such that when the shuttle stop is in the second position, the shuttle is free to move to the second position, and further comprising a stored energy device configured to drive the shuttle toward the second position.

10. The apparatus of claim 1, wherein the shuttle includes a holder stop movable from (i) a first position in which the holder stop is positioned to engage with at least a portion of the microneedle array holder to hold the microneedle array holder in the retracted position to (ii) a second position in which the holder stop is no longer positioned to engage with the microneedle array holder to hold the microneedle array holder in the retracted position, such that when the holder stop is in the second position, the microneedle array holder is free to move to the extended position, and further comprising a stored energy device configured to drive the microneedle array holder toward the extended position.

11. The apparatus of claim 1, wherein the actuator is movable with respect to the base of the housing, and wherein
when the actuator is in the first position, an outermost surface of the actuator extends beyond the base of the housing by a first distance, and
when the actuator is in the second position, the outermost surface of the actuator does not extend beyond the base of the housing, or
extends beyond the base of the housing by a second distance that is less than the first distance.

12. The apparatus of claim 1, wherein the actuator is movable between the first position and the second position along a first actuation axis, wherein the microneedle array holder is movable between the retracted position and the extended position along a second actuation axis, and wherein the first actuation axis and the second actuation axis are substantially parallel with respect to one another.

13. The apparatus of claim 12, wherein at least a portion of the actuator extends beyond the base of the housing when the actuator is in the first position.

14. The apparatus of claim 1, wherein the shuttle is movable between the first position and the second position along a third axis, and wherein the third axis is oriented substantially perpendicularly with respect to at least one of the first actuation axis and the second actuation axis.

15. The apparatus of claim 1, wherein the actuator includes a base and an opening formed in the base, and wherein at least a portion of the microneedle array extends through the opening in the actuator and beyond the base of the actuator when the microneedle array holder is in the extended position, and wherein the base of the actuator is configured to be coupled to the skin surface.

16. The apparatus of claim 1, wherein, when the actuator is in the first position, at least a portion of the actuator protrudes from the opening in the base of the housing and defines a base of the actuator configured to be coupled to the skin surface, wherein the base of the actuator includes a skin-contact adhesive.

17. The apparatus of claim 1, wherein the shuttle is biased toward the second position, and wherein the shuttle is restrained from moving to the second position by the actuator, until the actuator is moved to the second position.

18. The apparatus of claim 1, further comprising a stored energy device configured to drive the shuttle toward the second position.

19. The apparatus of claim 1, further comprising the active agent and a piston located in the reservoir of the cartridge, the piston movable between a first position in which the active agent is not being forced out of the reservoir and moved into the fluid path and a second position in which the active agent is being forced out of the reservoir and moved into the fluid path.

20. The apparatus of claim 19, further comprising a first stored energy device configured to initiate movement of the shuttle toward the second position and a second stored energy device configured to assist in moving the shuttle toward the second position and further configured to drive the piston toward its second position.

21. The apparatus of claim 19, further comprising an indicator that is movable with the piston between the first position and the second position of the piston, wherein the indicator is visible from outside the housing to indicate the position of the piston with respect to the housing.

22. The apparatus of claim 21, wherein the indicator is movable with the shuttle from the first position of the shuttle to the second position of the shuttle, and wherein the indicator is further movable with the piston and with respect to the shuttle when the shuttle is in the second position.

23. The apparatus of claim 1, wherein the fluid path includes or is in fluid communication with a piercing element configured to provide fluid communication between the reservoir of the cartridge and the fluid path, and further comprising a deformable sterility seal positioned to enclose the piercing element and configured to be pierced by the piercing element, and wherein the sterility seal is further configured to be changed from a first state in which the sterility seal defines a sterile chamber within which the piercing element is located to a second state in which the sterility seal has been pierced by the piercing element and the sterility seal is collapsed.

24. A method of using a microneedle injection apparatus, the method comprising:
  providing a microneedle injection apparatus comprising:
    a housing having a base and a cavity that extends through the base to define an opening in the base, wherein the base of the housing is configured to be positioned toward a skin surface;
    a microneedle array holder configured to hold a microneedle array and located in the housing, the microneedle array holder movable with respect to the opening in the base of the housing between
      a retracted position in which the microneedle array is recessed within the housing such that the microneedle array does not contact the skin surface when the apparatus is positioned on the skin surface and the microneedle array is coupled to the microneedle array holder, and
      an extended position in which at least a portion of the microneedle array is positioned to contact the skin surface via the opening when the apparatus is positioned on the skin surface and the microneedle array is coupled to the microneedle array holder;
    a shuttle configured to hold and carry a cartridge, the cartridge defining a reservoir configured to contain an active agent, the shuttle being movable between a first position in which the reservoir is not in fluid communication with a fluid path and a second position in which the reservoir is in fluid communication with the fluid path; and
    an actuator movable between a first position and a second position;
  moving the actuator to its second position to allow the shuttle to move toward its second position, wherein movement of the shuttle toward its second position allows the microneedle array holder to move to its extended position;
  wherein at least a portion of the actuator is located on a lower portion of the housing, wherein the actuator is configured to be moved from the first position to the second position in response to the apparatus being pressed toward a skin surface by pressing on an upper portion of the housing, and wherein the upper portion of the housing is located in an off-axis position with respect to an actuation axis of the actuator.

\* \* \* \* \*